US011142572B2

(12) United States Patent
Westerman et al.

(10) Patent No.: US 11,142,572 B2
(45) Date of Patent: Oct. 12, 2021

(54) ANTIBODIES TO HUMAN ERYTHROFERRONE AND USES THEREOF

(71) Applicant: Intrinsic LifeSciences LLC, La Jolla, CA (US)

(72) Inventors: Mark Westerman, La Jolla, CA (US); Huiling Han, La Jolla, CA (US); Vaughn Ostland, La Jolla, CA (US)

(73) Assignee: INTRINSIC LIFESCIENCES LLC, La Jolla, CA (US)

( * ) Notice: Subject to any disclaimer, the term of this patent is extended or adjusted under 35 U.S.C. 154(b) by 0 days.

(21) Appl. No.: 16/797,253

(22) Filed: Feb. 21, 2020

(65) Prior Publication Data

US 2020/0231668 A1     Jul. 23, 2020

Related U.S. Application Data

(62) Division of application No. 15/920,244, filed on Mar. 13, 2018, now Pat. No. 10,604,567.

(60) Provisional application No. 62/470,853, filed on Mar. 13, 2017, provisional application No. 62/471,195, filed on Mar. 14, 2017.

(51) Int. Cl.
| | |
|---|---|
| *G01N 33/53* | (2006.01) |
| *G01N 33/541* | (2006.01) |
| *C07K 16/26* | (2006.01) |
| *C07K 17/00* | (2006.01) |
| *G01N 33/68* | (2006.01) |
| *G01N 33/74* | (2006.01) |

(52) U.S. Cl.
CPC .......... *C07K 16/26* (2013.01); *G01N 33/541* (2013.01); *G01N 33/6893* (2013.01); *G01N 33/74* (2013.01); *G01N 33/746* (2013.01); *C07K 2317/21* (2013.01); *C07K 2317/51* (2013.01); *C07K 2317/515* (2013.01); *C07K 2317/92* (2013.01); *C12Y 111/01007* (2013.01); *G01N 2800/22* (2013.01)

(58) Field of Classification Search
None
See application file for complete search history.

(56) References Cited

U.S. PATENT DOCUMENTS

| | | | |
|---|---|---|---|
| 5,639,641 A | 6/1997 | Pedersen et al. | |
| 2005/0025763 A1 | 2/2005 | Williams et al. | |
| 2009/0252734 A1 | 10/2009 | Kanayama et al. | |
| 2010/0254979 A1 | 10/2010 | Staunton et al. | |
| 2014/0294827 A1 | 10/2014 | Gastwirt et al. | |
| 2016/0122409 A1 | 5/2016 | Ganz et al. | |

FOREIGN PATENT DOCUMENTS

| | | |
|---|---|---|
| EP | 194158 A2 | 9/1986 |
| WO | 1991/018291 A1 | 11/1991 |
| WO | 2014/071015 | 5/2014 |
| WO | WO-2014071015 A1 * | 5/2014 ............ A61P 35/00 |
| WO | 2018/027184 A1 | 2/2018 |

OTHER PUBLICATIONS

Lawen, A. Is erythroferrone finally the long sought-after systemic erythroid regulator of iron? World J Biol Chem vol. 6(3): 78-82 (Aug. 26, 2015). (Year: 2015).*
Kim A et al. "New insights into iron regulation and erythropoiesis" Curr Opin Hematol, 22:199-205, 2015.
Kautz L et al. Erythroferrone contributes to recovery from anemia of inflammation: Blood 124:2569-2574, 2015.
Chen et al. "Increased hepcidin in transferrin-treated thalassemic mice correlates with increased liver BMP2 expression and decreased hepatocyte ERK activation," Iron Metab Disord 100:297-308, 2015.
Andrews NC (2008). Forging a field: the golden age of iron biology. Blood 112(2):219-30.
Casanovas G, et al. (2012) The murine growth differentiation factor 15 is not essential for systemic iron homeostasis in phlebotomized mice. Haematologica 98:444-47.
Coates TD, et al. (2016). Management of iron overload in hemoglobinopathies: what is the appropriate target iron level. Ann N Y Acad Sci 1368:95-106.
Ganz, T., Olbina, G., Girelli, D., Nemeth, E., and Westerman, M. (2008). Immunoassay for human serum hepcidin. Blood 112:4292-4297.
Gutschow P, Schmidt PJ, Han H, Ostland V, Bartnikas TB, Pettiglio MA, Herrera C, Butler JS, Nemeth E, Ganz T, Fleming MD, Westerman M. (2015). A competitive enzyme-linked immunosorbent assay specific for murine hepcidin-1: correlation with hepatic mRNA expression in established and novel models of dysregulated iron homeostasis. Haematologica 100(2):167-177.
Honda H, Kobayashi Y, Onuma S, Shibagaki K, Yuza T, Hirao K, Yamamoto T, Tomosugi N, Shibata T.(2016). Associations among Erythroferrone and Biomarkers of Erythropoiesis and Iron Metabolism, and Treatment with Long-Term Erythropoiesis-Stimulating Agents in Patients on Hemodialysis. PLoS One.11(3):e0151601.
Kautz, L, Jung, G, Valore, EV, Rivella, S, Nemeth, E, Ganz, T (2014). Identification of erythroferrone as an erythroid regulator of iron metabolism Nat. Genet. 46:678-684.
Kautz L, Jung G, Du X, Gabayan V, Chapman J, Nasoff M, Nemeth E, Ganz T.(2015). Erythroferrone contributes to hepcidin suppression and iron overload in a mouse model of β-thalassemia. Blood 126(17) 2031-2037.
Kearney SL, Nemeth E, Neufeld EJ, Thapa D, Ganz T, Weinstein DA, Cunningham MJ. (2007). Urinary hepcidin in congenital chronic anemias. Pediatr Blood Cancer 48(1):57-63.

(Continued)

*Primary Examiner* — Elizabeth C. Kemmerer
*Assistant Examiner* — Regina M DeBerry
(74) *Attorney, Agent, or Firm* — K&L Gates LLP; Louis C. Cullman; Michelle Glasky Bergman

(57) ABSTRACT

Disclosed herein are antibodies specific for erythroferrone and assays comprising the antibodies. Also disclosed are methods for using the assays for the diagnosis or monitoring of disease.

20 Claims, 13 Drawing Sheets

Specification includes a Sequence Listing.

(56) References Cited

OTHER PUBLICATIONS

Van der Weerd NC, Grooteman MP, Bots ML, van den Dorpel MA, den Hoedt CH, Mazairac AH, Nubé MJ, Penne EL, Gaillard CA, Wetzels JF, Wiegerinck ET, Swinkels DW, Blankestijn PJ, Ter Wee PM; Contrast Investigators.(2012). Hepcidin-25 in chronic hemodialysis patients is related to residual kidney function and not to treatment with erythropoiesis stimulating agents. PLoS One. 7(7):e39783.

Papanikolaou G, Tzilianos M, Christakis JI, Bogdanos D, Tsimirika K, MacFarlane J, Goldberg YP, Sakellaropoulos N, Ganz T, Nemeth E (2005). Hepcidin in iron overload disorders. Blood 105(10):4103-4105.

Santini V, Girelli D, Sanna A, Martinelli N, Duca L, Campostrini N, Cortelezzi A, Corbella M, Bosi A, Reda G, Olivieri O, Cappellini MD. (2011). Hepcidin levels and their determinants in different types of myelodysplastic syndromes. PLoS One 6(8):e23109.

Tanno T, Porayette P, Sripichai O, Noh SJ, Byrnes C, Bhupatiraju A, Lee YT, Goodnough JB, Harandi O, Ganz T, Paulson RF, Miller JL. (2009). Identification of TWSG1 as a second novel erythroid regulator of hepcidin expression in murine and human cells. Blood 114:181-86.

Tessitore N, Girelli D, Campostrini N, Bedogna V, Pietro Solera G, Castagna A, Melilli E, Mantovani W, De Matteis G, Olivieri O, Poli A, Lupo A. (2010). Hepcidin is not useful as a biomarker for iron needs in haemodialysis patients on maintenance erythropoiesis-stimulating agents. Nephrol Dial Transplant. 25(12):3996-4002.

Han et al. "A novel dual monoclonal antibody sandwich ELISA for human erythroferrone," American Society for Hematoloty 2016 Meeting, Dec. 3, 2016; In: Blood128(22):1272.

Li H, Condon F, Kessler D, Nandi V, Rebosa M, Westerman M, Shaz BH, Ginzburg Y. (2016). Evidence of relative iron deficiency in platelet- and plasma-pheresis donors correlates with donation frequency. J. Clin. Apher. 31:551-558, 2016.

* cited by examiner

FIG. 1

```
Human ERFE(SEQ ID NO:1)    1 MAPARRPAGARLLLVYAGLLAAAAGLGSPEPGAPSRSRARREPPPGNELPRGPGESRAG      60
Murine ERFE (SEQ ID NO:2)  1 MASTRRPVFARTLLACASLLAA---MGLGYPESAEPVGTHARP-QPPGAELPA-------P     50

Human ERFE(SEQ ID NO:1)   61 PAARPPEPTAERAHSVDPRDAWMLFVRQSDKGVNGKKRSRGKAKKLKFGLPGPPGPPGPQ    120
Murine ERFE (SEQ ID NO:2) 51 PANSPPEPTIAHAHSVDPRDAWMLFVKQSDKGINSKRRS--KARRLKLGLPGPPGPPGPQ    108

Human ERFE(SEQ ID NO:1)  121 GPPGPIIPPEALLKETQLLIKGAVRQRERAEPRTCGPAGPVAASIAPVSATAGEDDD     180
Murine ERFE (SEQ ID NO:2)109 GPPGPFTPSEVLLKEFQLLLKGAVRQRESH-LEHCIRDLITPASGSPSRVP-AAQELDSQ    166

Human ERFE(SEQ ID NO:1)  181 VVGVIALLAPLAPGPHAPRVEAATLQRLRRDALVERRALHELGVYYLPDAEGAFHRGP    240
Murine ERFE (SEQ ID NO:2)167 DPGALLALLAATLAQGPRAPRVEAAFHCRLRRDVQVDRRALHELGIYYLPEVEGAFHRGP    226

Human ERFE(SEQ ID NO:1)  241 GLNLTSGQYAPVAGFYALAATLHVALEFPRGPFPFPRDHLRLLICTQSRQQRNASLEA    300
Murine ERFE (SEQ ID NO:2)227 GLNLTSGQYIAPVAGFVALAATLHVALIEQPRKGFIRPRDRLRLLICIQSLQQHNASLET    286

Human ERFE(SEQ ID NO:1)  301 IMGLESSSELFTISVNGVLYLQMGQWTSVFLDNASGCSLTVRSGSHFSAVLLGV     354
Murine ERFE (SEQ ID NO:2)287 VMGLENSSELFTISVNGVLYLQAGHYTSVFLDNASGSSLIVRSGSHFSAILLGL        340
```

ANTIBODIES TO HUMAN ERYTHROFERRONE AND USES THEREOF

CROSS-REFERENCE TO RELATED APPLICATIONS

The present application is a divisional of U.S. patent application Ser. No. 15/920,244, filed Mar. 13, 2018, which claims the benefit of U.S. Provisional patent applications 62/470,853 filed Mar. 13, 2017 and 62/471,195 filed Mar. 14, 2017, the entire contents of which are each incorporated by reference herein.

FIELD

The present invention relates to antibodies to polypeptides which regulate iron metabolism and methods of using the antibodies.

BACKGROUND

Red blood cell production is by far the main consumer of iron in the body. The existence of hormones that regulate iron in response to the needs of red blood cell production was proposed more than 50 years ago.

Erythroferrone (ERFE) is a hormone produced by erythroblasts in the bone marrow in response to erythropoietin (EPO). Recent animal studies have shown that rather than being involved in regulation of baseline erythropoiesis, ERFE acts as a stress erythropoiesis-specific regulator of hepcidin expression. High hepcidin expression leads to inhibition of absorption of dietary iron and the sequestration of iron in macrophages and hepatocytes. By suppressing hepcidin expression in the liver, ERFE contributes to increased dietary iron absorption and recycling of stored iron necessary for recovery of blood mass after hemorrhage. In addition, ERFE was found to be involved in hepcidin regulation in inherited iron loading anemias, such as β-thalassemia. ERFE has potential as a clinical marker for assessing erythropoiesis in patients with blood disorders.

To date, there have been no reports of a human ERFE assay in development and/or validation.

SUMMARY

Disclosed herein are antibodies specific for human erythroferrone (ERFE) and assays for detecting the presence of, and/or measuring the amount of, an ERFE polypeptide in a sample.

In some embodiments, an erythroferrone (ERFE)-binding antibody, or ERFE-binding fragment thereof, is provided, comprising a heavy chain variable region (VH) and a light chain variable region (VL), wherein the VH comprises:
 (i) an amino acid sequence that shares at least 80% sequence identity with the amino acid sequence of SEQ ID NO:18,
 (ii) an amino acid sequence that shares at least 80% sequence identity with the amino acid sequence of SEQ ID NO:28,
 (iii) an amino acid sequence that shares at least 80% sequence identity with an amino acid sequence of SEQ ID NO:38,
 (iv) an amino acid sequence that shares at least 80% sequence identity with the amino acid sequence of SEQ ID NO:48, or
 (v) an amino acid sequence that shares at least 80% sequence identity with the amino acid sequence of SEQ ID NO:58, and and the VL comprises:
 (vi) an amino acid sequence that shares at least 80% sequence identity with the amino acid sequence of SEQ ID NO:23;
 (vii) an amino acid sequence that shares at least 80% sequence identity with the amino acid sequence of SEQ ID NO:33,
 (viii) an amino acid sequence that shares at least 80% sequence identity with the amino acid sequence of SEQ ID NO:43,
 (ix) an amino acid sequence that shares at least 80% sequence identity with the amino acid sequence of SEQ ID NO:53, or
 (x) an amino acid sequence that shares at least 80% sequence identity with the amino acid sequence of SEQ ID NO:63.

In some embodiments, an ERFE-binding antibody, or ERFE-binding fragment thereof, is provided, wherein the antibody comprises:
 (i) one, two, or all three heavy chain CDRs having the amino acid sequences of SEQ ID NOs:19-21.
 (ii) one, two, or all three light chain CDRs having the amino acid sequences of SEQ ID NOs:24-26;
 (iii) one, two, or all three heavy chain CDRs having the amino acid sequences of SEQ ID NOs:29-31;
 (iv) one, two, or all three light chain CDRs having the amino acid sequences of SEQ ID NOs:34-36;
 (v) one, two, or all three heavy chain CDRs having the amino acid sequences of SEQ ID NOs:39-41,
 (vi) one, two, or all three light chain CDRs having the amino acid sequences of SEQ ID NOs:44-46,
 (vii) one, two, or all three heavy chain CDRs having the amino acid sequences of SEQ ID NOs:49-51,
 (viii) one, two, or all three light chain CDRs having the amino acid sequences of SEQ ID NOs:54-56
 (ix) one, two, or all three heavy chain CDRs having the amino acid sequences of SEQ ID NOs:59-61, or
 (x) one, two, or all three light chain CDRs having the amino acid sequences of SEQ ID NOs:64-66.

In some embodiments, the ERFE-binding antibody, or ERFE-binding fragment thereof, comprises an amino acid sequence that shares at least 80% sequence identity with the VH of SEQ ID NO:18 and an amino acid sequence that shares at least 80% sequence identity with the VL of SEQ ID NO:23. In some embodiments, the VH has an amino acid sequence that shares at least 90% sequence identity with the amino acid sequence of SEQ ID NO:18. In some embodiments, the VL has an amino acid sequence that shares at least 90% sequence identity with the amino acid sequence of SEQ ID NO:23.

In some embodiments, the ERFE-binding antibody, or ERFE-binding fragment thereof, comprises one, two, or all three heavy chain CDRs having the amino acid sequences of SEQ ID NOs:19-21 and one, two, or all three light chain CDRs having the amino acid sequences of SEQ ID NOs: 24-26.

In some embodiments, the ERFE-binding antibody, or ERFE-binding fragment thereof, comprises an amino acid sequence that shares at least 80% sequence identity with the VH of SEQ ID NO:28 or an amino acid sequence that shares at least 80% sequence identity with the VL of SEQ ID NO:33. In some embodiments, the VH has an amino acid sequence that shares at least 90% sequence identity with the amino acid sequence of SEQ ID NO:28. In some embodiments, the VL has an amino acid sequence that shares at least 90% sequence identity with the amino acid sequence of SEQ ID NO:33.

In some embodiments, the ERFE-binding antibody, or ERFE-binding fragment thereof, comprises one, two, or all three heavy chain CDRs having the amino acid sequences of SEQ ID NOs:29-31 and one, two, or all three light chain CDRs having the amino acid sequences of SEQ ID NOs: 34-36.

In some embodiments, the ERFE-binding antibody, or ERFE-binding fragment thereof, comprises an amino acid sequence that shares at least 80% sequence identity with the VH of SEQ ID NO:38 and an amino acid sequence that shares at least 80% sequence identity with the VL of SEQ ID NO:43. In some embodiments, the VH has an amino acid sequence that shares at least 90% sequence identity with the amino acid sequence of SEQ ID NO:38. In some embodiments, the VL has an amino acid sequence that shares at least 90% sequence identity with the amino acid sequence of SEQ ID NO:43.

In some embodiments, the ERFE-binding antibody, or ERFE-binding fragment thereof, comprises one, two, or all three heavy chain CDRs having the amino acid sequences of SEQ ID NOs:39-41 and one, two, or all three light chain CDRs having the amino acid sequences of SEQ ID NOs: 44-46.

In some embodiments, the ERFE-binding antibody, or ERFE-binding fragment thereof, comprises an amino acid sequence that shares at least 80% sequence identity with the VH of SEQ ID NO:48 and an amino acid sequence that shares at least 80% sequence identity with the VL of SEQ ID NO:53. In some embodiments, the VH has an amino acid sequence that shares at least 90% sequence identity with the amino acid sequence of SEQ ID NO:48. In some embodiments, the VL has an amino acid sequence that shares at least 90% sequence identity with the amino acid sequence of SEQ ID NO:53.

In some embodiments, the ERFE-binding antibody, or ERFE-binding fragment thereof, comprises one, two, or all three heavy chain CDRs having the amino acid sequences of SEQ ID NOs:49-51 and one, two, or all three light chain CDRs having the amino acid sequences of SEQ ID NOs: 54-56.

In some embodiments, the ERFE-binding antibody, or ERFE-binding fragment thereof, comprises an amino acid sequence that shares at least 80% sequence identity with the VH of SEQ ID NO:58 or an amino acid sequence that shares at least 80% sequence identity with the VL of SEQ ID NO:63. In some embodiments, the VH has an amino acid sequence that shares at least 90% sequence identity with the amino acid sequence of SEQ ID NO:58. In some embodiments, the VL has an amino acid sequence that shares at least 90% sequence identity with the amino acid sequence of SEQ ID NO:63.

In some embodiments, the ERFE-binding antibody, or ERFE-binding fragment thereof, comprises one, two, or all three heavy chain CDRs having the amino acid sequences of SEQ ID NOs:59-61 and one, two, or all three light chain CDRs having the amino acid sequences of SEQ ID NOs: 64-66.

In some embodiments, the ERFE-binding antibody, or ERFE-binding fragment thereof, comprises a VH and a VL, wherein the VH comprises the amino acid sequence of SEQ ID NO:18, 28, 38, 48, or 58 and the VL comprises the amino acid sequence of SEQ ID NO:23, 33, 43, 53, or 63. In some embodiments, the ERFE-binding antibody, or ERFE-binding fragment thereof, comprises the VH of SEQ ID NO: 18, 28, 38, 48, or 58 or the VL of SEQ ID NO: 23, 33, 43, 53, or 63.

In some embodiments, the ERFE-binding antibody, or ERFE-binding fragment thereof, comprises a CDRH1 having the amino acid sequence of SEQ ID NO: 19, 29, 39, 49, or 59. In some embodiments, the ERFE-binding antibody, or ERFE-binding fragment thereof, comprises a CDRH2 having the amino acid sequence of SEQ ID NO: 20, 30, 40, 50, or 60. In some embodiments, the ERFE-binding antibody, or ERFE-binding fragment thereof, comprises a CDRH3 having the amino acid sequence of SEQ ID NO: 21, 31, 42, 52, or 62.

In some embodiments, the ERFE-binding antibody, or ERFE-binding fragment thereof, comprises a CDRL1 having the amino acid sequence of SEQ ID NO: 24, 34, 44, 54, or 64. In some embodiments, the ERFE-binding antibody, or ERFE-binding fragment thereof, comprises a CDRL2 having the amino acid sequence of SEQ ID NO: 25, 35, 45, 55, or 65. In some embodiments, the ERFE-binding antibody, or ERFE-binding fragment thereof, comprises a CDRL3 having the amino acid sequence of SEQ ID NO: 26, 36, 46, 56, or 66.

In some embodiments, the ERFE-binding antibody, or ERFE-binding fragment thereof, is a chimeric antibody, a humanized antibody, or an antibody fragment.

Also disclosed herein are assays for detecting the presence of and/or measuring the amount of an erythroferrone (ERFE) protein in a sample, comprising: contacting the sample with a first antibody to form a first antibody-ERFE complex; and then detecting the presence of and/or measuring the amount of second antibody bound to the first antibody-ERFE complex, wherein the first antibody and the second antibody are not the same, thus determining the presence, and or the amount, of an ERFE protein in the sample. In some embodiments, the first antibody is a capture antibody and the second antibody is a detection antibody. In some embodiments, the assay comprises an ELISA assay. In some embodiments, the sample is a serum sample. In some embodiments, the first antibody specifically recognizes an ERFE polypeptide comprising, consisting essentially of, or consisting of a sequence of at least one of SEQ ID NOs: 1 and/or 3-16.

In some embodiments of the assay disclosed herein, the first antibody is selected from monoclonal antibodies 9B12, 17A5, 17E5, 2D2, 4C1, 6H9, 7H4, 9C7, 14B2, and 14D9, or an ERFE-binding fragment thereof. In some embodiments, the first antibody is selected from an antibodies disclosed herein. In some embodiments, the first antibody is 4C1 or an ERFE-binding fragment thereof.

In some embodiments of the assay disclosed herein, the first antibody is coated on a solid support. In some embodiments, the solid support is an ELISA plate.

In some embodiments of the assay disclosed herein, the detecting step comprises contacting a first antibody-ERFE polypeptide complex with a second antibody, and wherein the second antibody is labeled. In some embodiments, the second antibody is a labeled detection monoclonal antibody selected from 9B12, 17A5, 17E5, 2D2, 4C1, 6H9, 7H4, 9C7, 14B2, and 14D9. In some embodiments, the second antibody is a labeled detection antibody disclosed herein. In some embodiments, the second antibody is 2D2. In some embodiments, the label is biotin. In some embodiments, the label is horseradish peroxidase Also disclosed herein are methods of assessing erythropoiesis in a subject with disorder associated with ERFE or myonectin, comprising subjecting a sample from the subject with the assay disclosed herein. In some embodiments, the disorder is a thalassemia. In some embodiments, the disorder is a cardiovascular disorder.

Also disclosed herein are methods of assessing erythropoiesis in a subject with a disorder, comprising detecting erythroferrone in a sample from a subject with an antibody disclosed herein.

Also disclosed herein is a kit for a sandwich immunoassay comprising a capture antibody and a detection antibody wherein:

i) the capture antibody is 17A5 and the detection antibody is 2D2, 4C1, or 7H4;

ii) the capture antibody is 2D2 and the detection antibody is 4C1, 7H4; 17A5, or 9B12;

iii) the capture antibody is 4C1 and the detection antibody is 2D2, 7H4, 17A5, or 9B12;

iv) the capture antibody is 7H4 and the detection antibody is 2D2, 4C1 17A5, or 9B12;

v) The capture antibody is 9B12 and the detection antibody is 2D2, 4C1, 17A5, or 7H4.

In some embodiments of the kit, the capture antibody and the detection antibody are different antibodies. In some embodiments, the capture antibody is associated with a solid support. In some embodiments, the detection antibody is associated with a label. In some embodiments, the label is biotin. In some embodiments, the label is horseradish peroxidase. In some embodiments, the kit further comprises streptavidin-horseradish peroxidase. In some embodiments, the kit further comprises a substrate. In some embodiments, the kit further comprises instructions for performing the assay.

BRIEF DESCRIPTION OF THE DRAWINGS

FIG. 1 depicts the alignment of mouse (SEQ ID NO:2) and human (SEQ ID NO:1) erythroferrone (ERFE) proteins. The highlighted sequence is SEQ ID NO:16.

FIG. 3A: 17E5; FIG. 3B: 17A5; FIG. 3C: 2D2; FIG. 3D: 4C1; FIG. 3E: 6H9; FIG. 3F: 7H4) and different concentrations of recombinant human ERFE (150, 75.00, 37.50, 18.75 ng/well; first, second, third, and fourth bars). Eight biotinylated detection antibodies were tested to identify the presence of different concentrations of ERFE captured by the six capture antibodies.

DETAILED DESCRIPTION

Figure 2B:
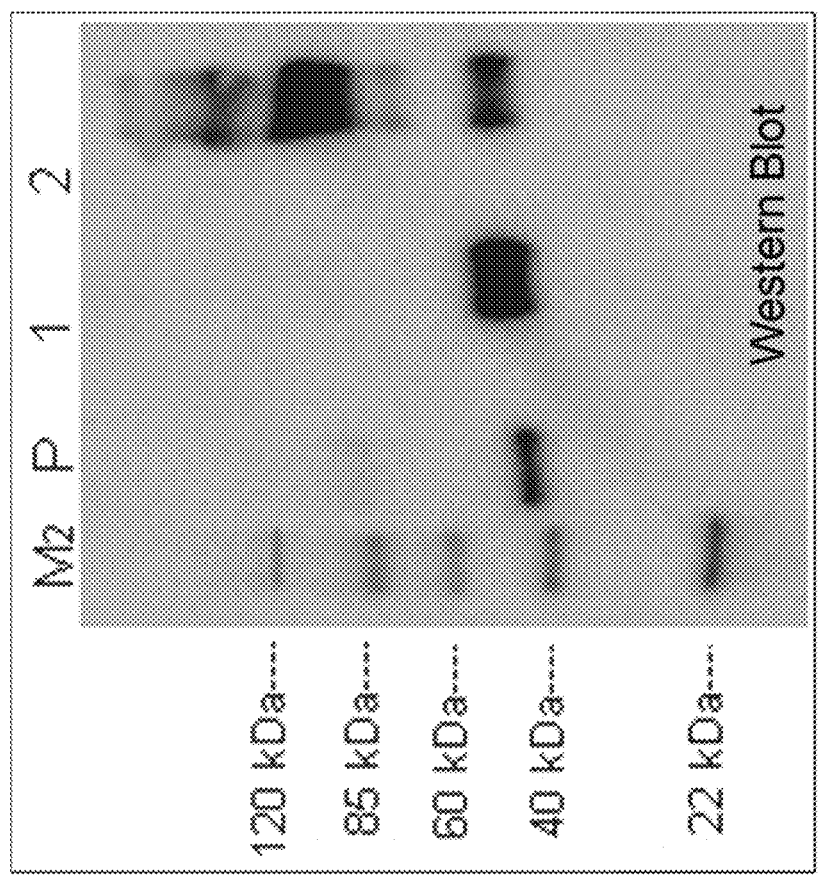
FIG. 2A-B depicts SDS-PAGE (FIG. 2A) and Western blot (FIG. 2B) of reduced (lane 1) and non-reduced (lane 2) human recombinant ERFE. Note the single dominant band of reduced ERFE compared to the multiple bands, particularly apparent on the western blot, suggesting a multimeric composition. Lane P denotes positive control antigen (western blot).

Disclosed herein are antibodies specific for erythroferrone (ERFE), methods of using the antibodies to detect ERFE, diagnose diseases associated with ERFE, and monitor the progression of diseases associated with ERFE.

Erythroferrone is the first identified "hormone" that mediates red cell production and the absorption and distribution of iron in subjects. Erythroferrone is made in the marrow of a subject and its production is greatly increased when the production of red blood cells is stimulated, e.g., after bleeding or during recovery from anemia. Erythroferrone regulates the supply of iron to meet the needs of red cell production in the marrow. Specifically, erythroferrone is found to act on the liver to suppress the production of the principal iron-regulatory protein, hepcidin. Thus, overproduction of erythroferrone may cause iron overload in diseases such as β-thalassemia and antagonizing erythroferrone could thus be used for the treatment of β-thalassemia.

Erythroferrone was discovered in the search for a factor that suppresses hepcidin expression. Hepcidin, a 25 amino acid peptide hormone synthesized by the liver, is the central regulator of iron homeostasis. Hepcidin acts by binding to the sole iron exporter ferroportin leading to its ubiquitination, internalization and degradation in lysosomes. When ferroportin disappears from the cell membranes, dietary absorption is inhibited and recycled iron is sequestered in macrophages, decreasing iron availability for erythropoiesis. In contrast, low hepcidin allows ferroportin to remain active on cells that export iron to plasma, making more iron available for hemoglobin synthesis. Iron, inflammation, or ER stress stimulates hepcidin production, whereas hypoxia, iron deficiency, and increased erythropoietic activity suppress it.

Hepcidin is suppressed after hemorrhage or erythropoietin (EPO) administration. Hepcidin is decreased in anemia caused by bleeding, hemolysis, or iron deficiency, or in hereditary anemias with ineffective erythropoiesis. The suppressive effect of erythropoiesis on hepcidin is particularly prominent in diseases with ineffective erythropoiesis where erythrocyte precursors massively expand but mostly undergo apoptosis at the erythroblast stage rather than mature into erythrocytes.

Erythroferrone is identical to myonectin (CTRP15), a protein expressed and secreted predominantly by skeletal muscle and involved in fatty acid metabolic processes and transport. Myonectin promotes lipid uptake into adipocytes and hepatocytes. Myonectin is a metabolic regulator secreted by skeletal muscle in response to changes in cellular energy state resulting from glucose or fatty acid fluxes and may be dysregulated in obese individuals. For example, expression and circulating levels of myonectin may be reduced in obese individuals.

The amino acid sequence of erythroferrone homologs is well conserved through vertebrate evolution so that mouse and human proteins are about 71% identical (FIG. 1) and the C-terminal half is about 44% identical to the zebrafish homolog. Domain analysis indicated that ERFE is a member of the TNFα superfamily with only a moderate similarity to known cytokines. TNFα and the RANK ligand (RANKL) are the closest relatives. CLUSTAL alignments of the C-terminal segment indicated that human members of the TNF family and human variants of ERFE differ in signal sequence.

Structural modeling of the entire protein using HHPredictB indicates that the N-terminal portion of the protein consists of a signal sequence followed by an open region with a collagen-like segment and the C-terminal portion is homologous to TNFα/RANKL. The similarities to TNFα are remarkable as, like EFRE, TNFα suppresses hepcidin mRNA in primary hepatocyte cultures. The similarity to TNFα predicts a tendency for ERFE to form multimers.

To facilitate the detection and characterization of ERFE, a series of antibodies directed against antigens in the human form of full-length erythroferrone and ERFE polypeptides were generated. In addition, antibodies against the internal and N-terminal epitopes of ERFE and/or ERFE proteins can be used in various assays and treatment methods according to the present disclosure. The term "protein" as used herein refers to a full length sequence and "polypeptide" refers to a fragment of a protein sequence.

In some embodiments, an ERFE protein comprises, consists essentially of, or consists of a sequence having about 70 to about 100%, about 80%, about 85%, about 90%, about 95%, about 96%, about 97%, about 98%, about 99%, or about 100% sequence identity to the entire sequence of human ERFE (MAPARRPAGARLLLVYAGL-LAAAAAGL GSPEPGAPSRSRARREPPPGNEL-PRGPGESRAGPAARPPEPTAER-
AHSVDPRDAWMLFVRQ
SDKGVNGKKRSRGKAKKLKFGLPGPPGPPGPQGPPG-PIIPPEALLKEFQLLLKGAVRQRERAE
PEPCTCGPAGPVAASLAPVSATAGEDDDDVVGDV-LALLAAPLAPGPRAPRVEAAFLCRLRRDA LVERRAL-HELGVYYLPDAEGAFRRGPGLNLT-
SGQYRAPVAGFYALAATLHVALGEPPRRGPPR PRDHLRLLICIQSRCQRNASLEAIMGLESS-
SELFTISVNGVLYLQMGQWTSVFLDNASGCSLTV RSGSHFSAVLLGV; SEQ ID NO: 1)

In some embodiments, an ERFE polypeptide comprises, consists essentially of, or consists of a sequence having about 70 to about 100%, about 80%, about 85%, about 90%, about 95%, about 96%, about 97%, about 98%, about 99%, or about 100% sequence identity to an ERFE fragment comprising GLPGPPGPPGPQGPPGP (SEQ ID NO:3), AHSVDPRDAWMLFV (SEQ ID NO:4), AHSVDPRDAWMLFVXQSDKGXN (SEQ ID NO:5), LLKEFQLLLKGAVRQRE (SEQ ID NO:6), GPRAPRVEAAF (SEQ ID NO:7), VXRRALHEL-GXYYLPX (SEQ ID NO:8), GLNLTSGQY (SEQ ID NO:9), APVAGFYALAATLHVAL (SEQ ID NO:10), XMGLEXSSELFTISVNGVLYLQ (SEQ ID NO: 11), SSELFTISVNGVLYLQ (SEQ ID NO: 12), TSVFLDNASG (SEQ ID NO: 13), SLTVRSGSHFSA (SEQ ID NO:14), SLTVRSGSHFSAXLLGX (SEQ ID NO:15), or EFQLLLKGAVRQRERAE-
PEPCTCGPAGPVAASLAPVSATAGEDDDD VVGDV-LALLAAPLAPGPRAPRVEAAFLCRLRRDALVERRAL-HELGVYYLPDAEGAFRRGPGLN
LTSGQYRAPVAGFYALAATLHVALGEPPRRGPPR-PRDHLRLLICIQSRCQRNASLEAIMGLESS
SELFTISVNGVLYLQMGQWTSVFLD-
NASGCSLTVRSGSHFSAVLLGV (SEQ ID NO: 16), wherein X is any amino acid.

In some embodiments disclosed herein the anti-ERFE antibody is a monoclonal antibody, a chimeric antibody, a humanized antibody, or an ERFE-binding fragment thereof. As disclosed herein, the anti-ERFE antibodies bind to a full length human ERFE protein (SEQ ID NO: 1) and/or a polypeptide of one of SEQ ID Nos. 3-16. In some embodiments, the anti-ERFE antibody does not preferentially bind to murine ERFE (SEQ ID NO:2) over human ERFE.

In some embodiments, the anti-ERFE antibodies disclosed herein recognize an epitope disclosed in one or more of SEQ ID Nos. 1 and 3-16. In some embodiments, the epitope is a conformational epitope that results from the three-dimensional tertiary structure of the protein. In some embodiments, the epitope is composed of non-contiguous amino acids. In some embodiments, the epitope comprises a glycosylated portion of the antigen.

The term "antibody" is herein used in the broadest sense and encompasses various antibody structures including, but not limited to, monoclonal antibodies, polyclonal antibodies, multispecific antibodies (e.g., bispecific antibodies), and antibody fragments so long as they exhibit the desired antigen-binding activity. An antibody broadly refers to any immunoglobulin (Ig) molecule comprised of heavy (H) chains and light (L) chains, or any functional fragment, mutant, variant, or derivation thereof, which retains the essential epitope-binding features of an Ig molecule. Such mutant, variant, or derivative antibody formats are known in the art, non-limiting embodiments of which are discussed below. An antibody is said to be "capable of binding" a molecule if it is capable of specifically reacting with the molecule. As used herein, the term "fragment", when referring to an antibody should be read to mean an antigen-binding fragment, such as an ERFE-binding antibody fragment.

The term "monoclonal antibody," as used herein, refers to an antibody obtained from identical immune cells that are clones of a unique parent cell and expressed from a particular, single encoding sequence (neglecting such variation as may arise in the expression system or cell). Typically monoclonal antibodies are monovalent in that they bind to the same epitope. The modifier "monoclonal" indicates the character of the antibody as being obtained from a clonal source and is not to be construed as requiring production of the antibody by any particular method. Monoclonal antibodies can be from any mammalian species such as, but not limited, human, mouse, rat, chicken, rabbit, camelids, etc.

An "antigen-binding portion" or "antigen-binding fragment" of an antibody (or simply "antibody portion" or "antibody fragment") refers to a molecule other than an intact antibody that comprises a portion of an intact antibody that binds the antigen to which the intact antibody binds (e.g., one or more fragments of an antibody that retain the ability to specifically bind to an antigen). Examples of antibody fragments include, but are not limited to, Fv, Fab, Fab', Fab'-SH, F(ab')$_2$, diabodies, linear antibodies, single-chain antibody molecules (e.g. scFv), heavy chain only antibodies (HCAb), and multispecific antibodies formed from antibody fragments. Papain digestion of intact antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. However these terms may also be applied to genetically encoded fragments of the same or similar nature, in addition to those fragments produced by proteolytic digestion. It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv). Such single chain antibodies are also intended to be encompassed within the term "antigen-binding portion" of an antibody. Other forms of single chain antibodies, such as diabodies are also encompassed.

The term "chimeric" antibody refers to an antibody in which a portion of the heavy and/or light chain is derived from a particular source or species, and at least one other portion of the heavy and/or light chain, including the remainder thereof, is derived from a different source or species. In certain embodiments, the CDRs are derived from a murine sequences and the framework regions are derived from human sequences.

The "class" of an antibody refers to the type of constant domain or constant region possessed by its heavy chain. There are five major classes of antibodies in humans: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent and/or bispecific. Diabodies are described more fully in, for example, EP 404,097; WO 1993/01161; Hudson et al., Nat. Med. 9: 129-134 (2003); and Hollinger et al., Proc. Natl. Acad. Sci. USA 90: 6444-6448 (1993). Triabodies and tetrabodies are also described in Hudson et al., Nat. Med. 9: 129-134 (2003).

The term "epitope" or "antigenic determinant" includes any protein or polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The "Fab" fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions.

"Framework" or "FR" refers to variable domain residues other than complementarity determining region (CDR) residues. The FR of a variable domain generally consists of four FR domains: FR1, FR2, FR3, and FR4. Accordingly, the CDR and FR sequences generally appear in the following sequence in either VH or VL sequences: FR1-CD1-FR2-CDR2-FR3-CDR3-FR4.

The terms "full length antibody," "intact antibody," and "whole antibody" are used herein interchangeably to refer to an antibody having a structure substantially similar to a native antibody structure or having heavy chains that contain an Fc region as defined herein.

"Fv" refers to the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

A "human antibody" is one which possesses an amino acid sequence encoded by a human genome or derived therefrom. The human antibodies of the disclosure may include amino acid residues not encoded by human germline immunoglobulin sequences (e.g., mutations introduced by random or site-specific mutagenesis in vitro or by somatic mutation in vivo), for example in the CDRs. However, the term "human antibody", as used herein, is not intended to include antibodies in which CDR sequences derived from the germline of another mammalian species, such as a mouse, have been grafted onto human framework sequences.

A "humanized" antibody refers to an antibody comprising heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which non-human CDR sequences are introduced into framework human VH and VL sequences to replace the corresponding human CDR sequences. A humanized antibody may thus comprise amino acid residues from non-human CDRs and amino acid residues from human FRs. In certain embodiments, a humanized antibody will comprise at least one, and typically two, variable domains, in which all or substantially all of the CDRs correspond to those of a non-human antibody (i.e., donor antibody), and all or substantially all of the FRs correspond to those of a human immunoglobulin consensus sequence. A humanized antibody optionally may comprise at least a portion of an antibody constant region derived from a human antibody. A "humanized form" of an antibody, e.g., a non-human antibody, refers to an antibody that has undergone humanization. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain. The humanized antibody can be selected from any class of immunoglobulins, including IgY, IgM, IgG, IgD, IgA, and IgE, and any isotype, including without limitation $IgA_1$, $IgA_2$, $IgG_1$, $IgG_2$, $IgG_3$, and $IgG_4$. The humanized antibody may comprise sequences from more than one class or isotype, and particular constant domains may be selected to optimize desired effector functions using techniques well-known in the art. The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a particular embodiment, such mutations, however, will not be extensive. Usually, at least 50, 55, 60, 65, 70, 75 or 80%, particularly at least 85%, more particularly at least 90%, and in particular at least 95% of the humanized antibody residues will correspond to those of the parental FR and CDR sequences.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having human heavy and light chain variable regions in which one or more of the human CDRs has been replaced with murine CDR sequences.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions termed complementarity determining regions (CDRs). (See, e.g., Kindt et al. Kuby Immunology, 6th ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively.

In certain embodiments, the anti-ERFE antibody is one of 9B12 (ATCC Accession Number PTA-123882), 17A5 (ATCC Accession Number PTA-123883), 2D2 (ATCC Accession Number PTA-123879), 4C1 (ATCC Accession Number PTA-123880), and 7H4 (ATCC Accession Number PTA-123881), or an antibody or antibody fragment that contains one or more CDRs from one of these antibodies.

An anti-ERFE antibody disclosed herein comprises 2D2, or a fragment thereof. In some embodiments, the anti-ERFE antibody, or fragment thereof, comprises a VH and a VL, wherein the VH comprises the amino acid sequence of SEQ ID NO:18 and the VL comprises the amino acid sequence of SEQ ID NO:23. In some embodiments, the anti-ERFE antibody, or fragment thereof, comprises one of SEQ ID NO:18 or SEQ ID NO:23. In some embodiments, the VH has an amino acid sequence that shares at least 90% sequence identity with the amino acid sequence of SEQ ID NO:18. In some embodiments, the VL has an amino acid sequence that shares at least 90% sequence identity with the amino acid sequence of SEQ ID NO:23. In some embodiments, the anti-ERFE antibody, or fragment thereof, comprises one, two, or all three heavy chain CDRs having the amino acid sequences of SEQ ID NOs:19-21. In some embodiments, the anti-ERFE antibody, or fragment thereof, comprises one, two, or all three light chain CDRs having the amino acid sequences of SEQ ID NOs:24-26. In some embodiments, the antibody is a chimeric antibody, a humanized antibody, or an antibody fragment disclosed herein.

An anti-ERFE antibody disclosed herein comprises 4C1, or a fragment thereof. In some embodiments, the anti-ERFE antibody, or fragment thereof, comprises a VH and a VL, wherein the VH comprises the amino acid sequence of SEQ ID NO:28 and the VL comprises the amino acid sequence of SEQ ID NO:33. In some embodiments, the anti-ERFE antibody, or fragment thereof, comprises one of SEQ ID NO:28 or SEQ ID NO:33. In some embodiments, the VH has an amino acid sequence that shares at least 90% sequence identity with the amino acid sequence of SEQ ID NO:28. In some embodiments, the VL has an amino acid sequence that shares at least 90% sequence identity with the amino acid sequence of SEQ ID NO:33. In some embodiments, the anti-ERFE antibody, or fragment thereof, comprises one, two, or all three heavy chain CDRs having the amino acid sequences of SEQ ID NOs:29-31. In some embodiments, the anti-ERFE antibody, or fragment thereof, comprises one, two, or all three light chain CDRs having the amino acid sequences of SEQ ID NOs:34-36. In some embodiments, the antibody is a chimeric antibody, a humanized antibody, or an antibody fragment disclosed herein.

An anti-ERFE antibody disclosed herein comprises 7H4, or a fragment thereof. In some embodiments, the anti-ERFE antibody, or fragment thereof, comprises a VH and a VL, wherein the VH comprises the amino acid sequence of SEQ ID NO:38 and the VL comprises the amino acid sequence of SEQ ID NO:43. In some embodiments, the anti-ERFE antibody, or fragment thereof, comprises one of SEQ ID NO:38 or SEQ ID NO:43. In some embodiments, the VH has an amino acid sequence that shares at least 90% sequence identity with the amino acid sequence of SEQ ID NO:38. In some embodiments, the VL has an amino acid sequence that shares at least 90% sequence identity with the amino acid sequence of SEQ ID NO:43. In some embodiments, the anti-ERFE antibody, or fragment thereof, comprises one, two, or all three heavy chain CDRs having the amino acid sequences of SEQ ID NOs:39-41. In some embodiments, the anti-ERFE antibody, or fragment thereof, comprises one, two, or all three light chain CDRs having the amino acid sequences of SEQ ID NOs:44-46. In some embodiments, the antibody is a chimeric antibody, a humanized antibody, or an antibody fragment disclosed herein.

An anti-ERFE antibody disclosed herein comprises 9B12, or a fragment thereof. In some embodiments, the anti-ERFE antibody, or fragment thereof, comprises a VH and a VL, wherein the VH comprises the amino acid sequence of SEQ ID NO:48 and the VL comprises the amino acid sequence of SEQ ID NO:53. In some embodiments, the anti-ERFE antibody, or fragment thereof, comprises one of SEQ ID NO:48 or SEQ ID NO:53. In some embodiments, the VH has an amino acid sequence that shares at least 90% sequence identity with the amino acid sequence of SEQ ID NO:48. In some embodiments, the VL has an amino acid sequence that shares at least 90% sequence identity with the amino acid sequence of SEQ ID NO:53. In some embodiments, the anti-ERFE antibody, or fragment thereof, comprises one, two, or all three heavy chain CDRs having the amino acid sequences of SEQ ID NOs:49-51. In some embodiments, the anti-ERFE antibody, or fragment thereof, comprises one, two, or all three light chain CDRs having the amino acid sequences of SEQ ID NOs:54-56. In some embodiments, the antibody is a chimeric antibody, a humanized antibody, or an antibody fragment disclosed herein.

An anti-ERFE antibody disclosed herein comprises 17A5, or a fragment thereof. In some embodiments, the anti-ERFE antibody, or fragment thereof, comprises a VH and a VL, wherein the VH comprises the amino acid sequence of SEQ ID NO:58 and the VL comprises the amino acid sequence of SEQ ID NO:63. In some embodiments, the anti-ERFE antibody, or fragment thereof, comprises one of SEQ ID NO:58 or SEQ ID NO:63. In some embodiments, the VH has an amino acid sequence that shares at least 90% sequence identity with the amino acid sequence of SEQ ID NO:58. In some embodiments, the VL has an amino acid sequence that shares at least 90% sequence identity with the amino acid sequence of SEQ ID NO:63. In some embodiments, the anti-ERFE antibody, or fragment thereof, comprises one, two, or all three heavy chain CDRs having the amino acid sequences of SEQ ID NOs:59-61. In some embodiments, the anti-ERFE antibody, or fragment thereof, comprises one, two, or all three light chain CDRs having the amino acid sequences of SEQ ID NOs:64-66. In some embodiments, the antibody is a chimeric antibody, a humanized antibody, or an antibody fragment disclosed herein.

In some embodiments, the anti-ERFE antibody, or fragment thereof, has a CDRH1 comprising one of SEQ ID NOs: 19, 29, 39, 49, or 59. In some embodiments, the anti-ERFE antibody, or fragment thereof, has a CDRH2 comprising one of SEQ ID NOs: 20, 30, 40, 50, or 60. In some embodiments, the anti-ERFE antibody, or fragment thereof, has a CDRH3 comprising one of SEQ ID NOs: 21, 31, 42, 52, or 62.

In some embodiments, the anti-ERFE antibody, or fragment thereof, has a CDRL1 comprising one of SEQ ID NOs: 24, 34, 44, 54, or 64. In some embodiments, the anti-ERFE antibody, or fragment thereof, has a CDRL2 comprising one of SEQ ID NOs: 25, 35, 45, 55, or 65. In some embodiments, the anti-ERFE antibody, or fragment thereof, has a CDRL3 comprising one of SEQ ID NOs: 26, 36, 46, 56, or 66.

In some embodiments, anti-ERFE antibodies, or fragments thereof, with improved properties are provided. For example, anti-ERFE antibodies or fragments thereof, having improved affinity for ERFE are prepared by affinity maturation of an antibody or fragment of the disclosed herein.

While the CDRs are important for epitope recognition, they are not essential to the antibodies and fragments thereof disclosed herein. Accordingly, antibodies and fragments are provided which have improved properties produced by, for example, affinity maturation of an antibody disclosed herein.

Diverse antibodies and antibody fragments, as well as antibody mimics may be readily produced by mutation, deletion and/or insertion within the variable and constant region sequences that flank a particular set of CDRs. Thus, for example, different classes of antibodies are possible for a given set of CDRs by substitution of different heavy chains, whereby, for example, $IgG_{1-4}$, IgM, $IgA_{1-2}$, IgD, IgE antibody types and isotypes may be produced. Similarly, artificial antibodies within the scope of the present disclosure may be produced by embedding a given set of CDRs within an entirely synthetic framework.

Humanized antibodies, or antibodies adapted for non-rejection by other mammals, may be produced using several technologies such as resurfacing and CDR grafting. In the resurfacing technology, molecular modeling, statistical analysis and mutagenesis are combined to adjust the non-CDR surfaces of variable regions to resemble the surfaces of known antibodies of the target host. Strategies and methods for the resurfacing of antibodies, and other methods for reducing immunogenicity of antibodies within a different host, are disclosed in U.S. Pat. No. 5,639,641, which is hereby incorporated by reference in its entirety. In the CDR grafting technology, the murine heavy and light chain CDRs are grafted into a fully human framework sequence.

The present disclosure also encompasses functional equivalents of the antibodies described in this specification. Functional equivalents have binding characteristics that are comparable to those of the antibodies, and include, for example, chimerized, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424, which are incorporated in their respective entireties by reference. Functional equivalents include polypeptides with amino acid sequences substantially the same as the amino acid sequence of the variable or hypervariable regions of the antibodies of the invention. "Substantially the same" as applied to an amino acid sequence is defined herein as a sequence with at least about 90%, and more preferably at least about 95% sequence identity to another amino acid sequence, as determined by the FASTA search method in accordance with Pearson and Lipman, Proc. Natl. Acad. Sci. USA 85, 2444-2448 (1988). Functional equivalents include chimeric antibodies, single-chain antibody fragments, and other antibody fragments which maintain binding affinity for ERFE.

Also within the scope of the present disclosure are amino acid sequence variants of the anti-ERFE antibodies are prepared by introducing appropriate nucleotide changes into the antibody DNA, or by peptide synthesis. Such variants include, for example, deletions from, and/or insertions into and/or substitutions of, residues within the amino acid sequences of the antibodies of the examples herein. Any combination of deletion, insertion, and substitution is made to arrive at the final construct, provided that the final construct possesses the desired characteristics. The amino acid changes also may alter post-translational processes of the humanized or variant antibodies, such as changing the number or position of glycosylation sites.

A useful method for identification of certain residues or regions of the antibodies that are preferred locations for mutagenesis is called "alanine scanning mutagenesis". A residue or group of target residues are identified (e.g., charged residues such as Arg, Asp, His, Lys, and Glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-ERFE antibody with an N-terminal methionyl residue or the antibody fused to an epitope tag. Other insertional variants of the antibody molecules include the fusion to the N- or C-terminus of the antibody of an enzyme or a polypeptide which increases the serum half-life of the antibody.

Another type of variant is an amino acid substitution variant. These variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |

TABLE 1-continued

| Original Residue | Exemplary Substitutions | Preferred Substitutions |
|---|---|---|
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Hydrophobic: Norleucine, Met, Ala, Val, Leu, Ile;
(2) Neutral hydrophilic: Cys, Ser, Thr;
(3) Acidic: Asp, Glu;
(4) Basic: Asn, Gin, His, Lys, Arg;
(5) Residues that influence chain orientation: Gly, Pro; and
(6) Aromatic: Trp, Tyr, Phe.

Non-conservative substitutions will entail exchanging a member of one of these classes for another class.

Any cysteine residue not involved in maintaining the proper conformation of the anti-ERFE antibodies also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene IIII product of M13 packaged within each particle. The phage-displayed variants are then screened for their biological activity (e.g., binding affinity) as herein disclosed. In order to identify candidate hypervariable region sites for modification, alanine scanning mutagenesis can be performed to identified hypervariable region residues contributing significantly to antigen binding. Alternatively, or in addition, it may be beneficial to analyze a crystal structure of the antigen-antibody complex to identify contact points between the antibody and human ERFE. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-ERFE antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an anti-ERFE antibody.

Other modifications of the anti-ERFE antibodies are contemplated. For example, it may be desirable to modify the antibodies with respect to effector function, so as to enhance the effectiveness of the antibody in treating disease, for example. For example cysteine residue(s) may be introduced in the Fc region, thereby allowing interchain disulfide bond formation in this region.

The antibodies disclosed herein may be produced by recombinant means. Thus, disclosed herein are nucleic acids encoding the antibodies, expression vectors containing nucleic acids encoding the antibodies, and cells comprising the nucleic acid encoding the antibodies. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the antibody sequences are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or $E. coli$ cells, and the antibody is recovered from the cells (supernatant or cells after lysis).

Accordingly, certain embodiments disclosed herein include a method for the preparation of an anti-ERFE antibody, comprising the steps of a) transforming a host cell with at least one expression vector comprising nucleic acid molecules encoding the antibody; b) culturing the host cell under conditions that allow synthesis of the antibody molecule; and c) recovering said antibody molecule from the culture.

The antibodies are suitably separated from the culture medium by conventional immunoglobulin purification procedures such as, for example, protein A-Sepharose, hydroxyapatite chromatography, gel electrophoresis, dialysis, or affinity chromatography.

As used herein, the expressions "cell," "cell line," and "cell culture" are used interchangeably and all such designations include progeny. Thus, the words "transformants" and "transformed cells" include the primary subject cell and cultures derived therefrom without regard for the number of passages. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection can be carried out e.g. by the calcium phosphate precipitation method. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The term "host cell" as used herein denotes any kind of cellular system which can be engineered to generate the antibodies disclosed herein. In one embodiment HEK293 cells and CHO cells are used as host cells.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Similarly, in some instances an intron may be present between nucleic acid sequences that are operably linked. Linking is accomplished by ligation at convenient restriction sites. If such sites do not exist, then synthetic oligonucleotide adaptors or linkers are used in accordance with conventional practice.

Also disclosed herein are isolated nucleic acids encoding the anti-ERFE antibodies, vectors and host cells comprising the nucleic acids, and recombinant techniques for the production of the antibodies.

For recombinant production of the antibodies, the nucleic acid encoding it may be isolated and inserted into a replicable vector for further cloning (amplification of the DNA) or for expression. In some embodiments, the antibody may be produced by homologous recombination, e.g. as described in U.S. Pat. No. 5,204,244, specifically incorporated herein by reference for all it discloses regarding antibody production. DNA encoding the antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615, specifically incorporated herein by reference for all it discloses regarding protein expression.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *S. typhimurium, Serratia*, e.g., *S. marcescans*, and *Shigella*, as well as *Bacilli* such as *B. subtilis* and *B. licheniformis, Pseudomonas* such as *P. aeruginosa*, and *Streptomyces*. One exemplary *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-ERFE antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; Yarrowia* (EP 402,226); *Pichia pastoris* (EP 183,070); *Candida; Trichoderma reesia* (EP 244,234); *Neurospora crassa; Schwanniomyces* such as *S. occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-ERFE antibodies are derived from multicellular organisms, including invertebrate cells such as plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *B. mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transformed with the above-described expression vectors for anti-ERFE antibody production and cultured in conventional nutrient media modified as appropriate for inducing promoters, selecting transformants, or amplifying the genes encoding the desired sequences.

The host cells used to produce the anti-ERFE antibodies may be cultured in a variety of media. Commercially available media such as Ham's F10, Minimal Essential Medium (MEM), RPMI-1640, and Dulbecco's Modified Eagle's Medium (DMEM) are suitable for culturing the host cells. In addition, U.S. Pat. Nos. 4,767,704; 4,657,866; 4,927,762; 4,560,655; or U.S. Pat. No. 5,122,469; WO 90/03430; WO 87/00195; or US Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMY-CIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration.

The antibody composition prepared from the cells can be purified using, for example, hydroxyapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains. Protein G is recommended for all mouse isotypes and for human γ3. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

In some embodiments, disclosed herein are assays for detecting the presence of, and/or measuring the amount of, an ERFE protein or polypeptide in a sample which comprises contacting the sample with an antibody raised against an ERFE protein or polypeptide according to the present disclosure and then detecting the presence of, and/or measuring the amount of, bound antibodies.

As used herein, the term "sample" refers to anything which may contain ERFE for which an ERFE assay is desired. The sample may be a biological sample, such as a biological fluid or a biological tissue. Examples of biological fluids include blood, serum, plasma, saliva, sputum, ocular lens fluid, sweat, urine, milk, ascites fluid, mucous, synovial fluid, peritoneal fluid, transdermal exudates, pharyngeal exudates, bronchioalveolar lavage, tracheal aspirations, cerebrospinal fluid, semen, cervical mucus, vaginal or urethral secretions, amniotic fluid, and the like. Biological tissues comprise an aggregate of cells, usually of a particular kind together with their intercellular substance that form one of the structural materials of a human or animal, including connective, epithelium, muscle, and nerve tissues. The sample can be used as obtained directly from the source or following a pretreatment so as to modify its character.

In some embodiments, the assay is an immunoassay. An exemplary, non-limiting immunoassay is an enzyme-linked immunosorbant assay (ELISA). In other embodiments, the immunoassay is an immunohistochemical assay. Immunoassays measure substances, such as analytes, proteins, etc., using the specificity of an antibody to the substance.

In one embodiment, the ELISA is a sandwich ELISA. In such an assay, a capture antibody specific for the substance is associated with a solid support, such as a microtiter plate. A liquid containing the substance (or suspected of containing the substance, or a sample in need of determining not to include the substance) is allowed to bind to the capture antibody. Then a detection antibody, also specific for the substance, is added to allow detection of substance bound to the capture antibody.

In some embodiments, the assay is an immunohistochemical assay. Immunohistochemistry involves the process of selectively imaging antigens (proteins) in a tissue section by exploiting the principle of antibodies binding specifically to antigens in biological tissues. Visualizing an antibody-antigen interaction can be accomplished in a number of ways. In the most common instance, a detection antibody is used which allows the detection of the substance to which the antibody is bound.

In some embodiments, the detection antibody is a labeled antibody. The label can include a radioactive label, an enzyme label, a colorimetric label, a fluorescent label, a chemiluminescent label, or other labels known to persons of skill in the art. In some embodiments, the label is biotin. If the label is biotin, a secondary detection agent, comprising avidin, or streptavidin, is required conjugated to an enzyme, a radioisotope, a colorimetric agent, or other agent. In one embodiment, the secondary detection agent is streptavidin-horseradish peroxidase.

In some embodiments, the label is an enzymatic label such as a peroxidase (e.g., horseradish peroxidase), a galactosidase (e.g., β-D-galactosidase), or a phosphatase (e.g., alkaline phosphatase). For enzymatic labels, a substrate is needed which is cleaved by the enzyme to produce a color, fluorescence, or luminescence, which is measured spectrophotometrically. Exemplary colorimetric substrates for peroxidase include, but are not limited to, 3,3',5,5'-tetramethylbenzidine (TMB), 3,3',4,4' diaminobenzidine (DAB), 4-chloro-1-naphthol (4CN), 2,2'-azino-di [3-ethylbenzthiazoline] sulfonate (ABTS), and o-phenylenediamine (OPD). In some embodiments, when the assay is an ELISA, the substrate is TMB which produces a blue color which is measured at a wavelength of 650 nm. The reaction can be halted by addition of acid or another stop reagent. Using a sulfuric acid stop solution turns TMB yellow and the color can then be read at 450 nm. Exemplary colorimetric substrates for phosphatase include, but are not limited to, 5-bromo-4-chloro-3-indolyl-phosphate/nitroblue tetrazolium (BCIP/NBT) and p-nitrophenylphosphate (p-NPP). Exemplary colorimetric substrates for galactosidase include, but are not limited to, 5-dodecanoylaminofluorescein di-β-D-galactopyranoside (C12FDG), 9H-(1,3-dichloro-9,9-dimethylacridin-2-one-7-yl), and β-D-galactopyranoside (DDAO galactoside). Exemplary fluorescent substrates include, but are not limited to, 4-methylumbelliferyl phosphate (4-MUP; for phosphatase), and 4-methylumbelliferyl galactoside (MUG; for galactosidase), fluorescein di-β-D-galactopyranoside (FDG; for galactosidase), hydroxyphenylacetic acid (HPA; for peroxidase), and 3-p-hydroxyphenyl-propionic acid (HPPA; for peroxidase). Exemplary luminescent substrates include, but are not limited to, luminol, polyphenols (e.g., pyrogallol, pupurogallin, gallic acid, and umbelliferone) and acridine esters, and luciferin for peroxidase; 3-(2'-spiroadamantane)-4-methyl-4-(3'-phosphoryloxyphenyl-1, 2-dioxetane, disodium salt) (AMPPD) for phosphatase; and (3-(2'-spiroadamantane)-4-methoxy-4-(3'-β-D-galactopyranosyloxyphenyl-1,2-dioxetane (AMPGD) for galactosidase.

In some embodiments, the label is horseradish peroxidase and the substrate is TMB.

In some embodiments, the label is a colorimetric label, a fluorescent label, or a luminescent label. An exemplary colorimetric label includes, but is not limited to, nanoparticulate gold. Exemplary fluorescent labels include, but are not limited to, ethidium bromide, fluorescein and its derivatives, rhodamine and its derivatives, green fluorescent protein, Texas Red, Cascade Blue, Oregon Green, Marina Blue, an atto label, a CF™ dye, an Alexa Fluor, and a cyanine dye. Exemplary luminescent labels include, but are not limited to, luciferin and firefly luciferase.

Antibodies suitable for use as the capture and detection antibodies can be monoclonal or polyclonal and can be derived from many species. Exemplary species of antibodies include, human, rabbit, mouse, rat, camelids, llama, chicken, etc. In some embodiments, the capture and detection antibodies are both mouse monoclonal antibodies. In other embodiments, the capture and detection antibodies are rabbit monoclonal or polyclonal antibodies. Also within the scope of the present disclosure are assays in which the capture and detection antibodies are of different species, or that one is a polyclonal antibody and one is a monoclonal antibody.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

Also disclosed are methods of using the antibodies to diagnose or monitor a hepcidin-related disorder, a disease of iron homeostasis, a disorder associated with ERFE, and/or a disorder associated with myonectin.

As used herein, a "hepcidin-related disorder" refers to a condition caused by or associated with an abnormal level of hepcidin (e.g., hepcidin excess or hepcidin deficiency relative to the degree of anemia or iron stored) which disrupts iron homeostasis. A disruption in iron homeostasis can in turn result in secondary diseases such as anemia. Acute or chronic inflammatory conditions can result in up-regulation of hepcidin expression, which can result in decreased circulating iron levels, which can cause anemia or worsen existing anemia. Exemplary hepcidin-related inflammatory diseases include anemia of cancer, anemia of chronic disease, anemia of inflammation, chemotherapy-induced anemia, chronic kidney disease (stage I, II, III, IV or V), end stage renal disease, chronic renal failure congestive heart failure, cancer, rheumatoid arthritis, systemic lupus erythematosus, Crohn's disease, H. pylori infection or other bacterial infections, hepatitis C, HIV, and other viral illnesses, arteriosclerosis, atherosclerosis, cirrhosis of the liver, pancreatitis, sepsis, vasculitis, iron-deficiency, hypochromic microcytic anemia, sickle cell disease, and conditions with hepcidin excess.

As used herein, the phrase "disease (or disorder) of iron homeostasis" refers to a condition in which a subject's iron levels require modulation. It includes hepcidin-related disorders; conditions not associated with elevated levels of hepcidin that nevertheless would benefit from inhibition of hepcidin activity, such as a disruption in iron homeostasis not caused by hepcidin; diseases where aberrant iron absorption, recycling, metabolism or excretion causes a disruption in normal iron blood levels or tissue distribution; diseases where iron dysregulation is a consequence of another disease or condition, such as inflammation, cancer or chemotherapy; diseases or disorders resulting from abnormal iron blood levels or tissue distribution; and diseases or disorders that can be treated by modulating iron levels or distribution. Non-limiting examples of such diseases or disorders of iron homeostasis, hepcidin-related disorders and inflammatory conditions which can result in hepcidin excess include African iron overload, iron refractory iron deficiency anemia (IRIDA), alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, acute kidney injury (AKI), cardiopulmonary bypass-associated AKI, drug or toxin associated AKI, cirrhosis of liver, classic hemochromatosis, collagen-induced arthritis (CIA), conditions with hepcidin excess (elevated hepcidin), congenital dyserythropoietic anemia, congestive heart failure, Crohn's disease, Celiac disease, inflammatory bowel disease (IBD), diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, Gracile syndrome, H. pylori infection or other bacterial infections, hereditary hemochromatosis, acquired hemochromatosis, hemochromatosis resulting from mutations in transferrin receptor 2, hemoglobinopathies, hepatitis, hepatitis (Brock), hepatitis C, hepatocellular carcinoma, HIV or other viral illnesses, Huntingon's disease, hyperferritinemia, hypochromic microcytic anemia, hypo ferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease.

Non-inflammatory conditions which are implicated in a disruption of iron regulation include, but are not limited to, vitamin B6 deficiency, vitamin B12 deficiency, folate deficiency, pellagra, funicular myelosis, pseudoencephalitis, Parkinson's disease, Alzheimer's disease, coronary heart disease, osteopenia and osteoporosis, hemoglobinopathies and disorders of red cell metabolism, and peripheral occlusive arterial disease.

As used herein, the phrase "disease (or disorder) associated with ERFE" refers to a condition caused by or associated with an abnormal level of ERFE (e.g., ERFE excess or ERFE deficiency). Exemplary diseases associated with ERFE include, but are not limited to, thalassemias, sickle cell disease, diseases or disorders of iron hemostasis, and hepcidin-related disorders.

Thalassemias are inherited blood disorders characterized by abnormal hemoglobin production. Symptoms depend on the type and can vary from none to severe. There are two main types, alpha thalassemia and beta thalassemia. The severity of alpha and beta thalassemia depends on how many of the four genes for alpha globin or two genes for beta globin are missing. Mutated alleles are called β+ when partial function is conserved (either the protein has a reduced function, or it functions normally but is produced in reduced quantity) or β0, when no functioning protein is produced.

As used herein, the phrase "disease (or disorder) associated with myonectin" refers to a condition caused by or associated with an abnormal level of myonectin (e.g., myonectin excess or myonectin deficiency). Exemplary diseases associated with myonectin include, but are not limited to, diseases or disorders of iron hemostasis, hepcidin-related disorders, cardiovascular diseases or disorders, diabetes, obesity, and insulin resistance.

As used herein, the term "subject" or "patient" or "individual" refers to mammals and includes, without limitation, domestic animals (e.g., cows, sheep, cats, dogs, and horses), primates (e.g., humans and non-human primates such as monkeys), rabbits, and rodents (e.g., mice and rats). In certain embodiments, the subject is human.

EMBODIMENTS

Embodiment 1

An erythroferrone (ERFE)-binding antibody, or ERFE-binding fragment thereof, comprising a heavy chain variable region (VH) and a light chain variable region (VL), wherein the VH comprises:
(i) an amino acid sequence that shares at least 80% sequence identity with the amino acid sequence of SEQ ID NO:18,
(ii) an amino acid sequence that shares at least 80% sequence identity with the amino acid sequence of SEQ ID NO:28,
(iii) an amino acid sequence that shares at least 80% sequence identity with an amino acid sequence of SEQ ID NO:38,
(iv) an amino acid sequence that shares at least 80% sequence identity with the amino acid sequence of SEQ ID NO:48, or
(v) an amino acid sequence that shares at least 80% sequence identity with the amino acid sequence of SEQ ID NO:58, and and the VL comprises:
(vi) an amino acid sequence that shares at least 80% sequence identity with the amino acid sequence of SEQ ID NO:23;
(vii) an amino acid sequence that shares at least 80% sequence identity with the amino acid sequence of SEQ ID NO:33,
(viii) an amino acid sequence that shares at least 80% sequence identity with the amino acid sequence of SEQ ID NO:43,
(ix) an amino acid sequence that shares at least 80% sequence identity with the amino acid sequence of SEQ ID NO:53, or
(x) an amino acid sequence that shares at least 80% sequence identity with the amino acid sequence of SEQ ID NO:63.

Embodiment 2

An ERFE-binding antibody, or ERFE-binding fragment thereof, wherein the antibody comprises:
(i) one, two, or all three heavy chain CDRs having the amino acid sequences of SEQ ID NOs:19-21.
(ii) one, two, or all three light chain CDRs having the amino acid sequences of SEQ ID NOs:24-26;
(iii) one, two, or all three heavy chain CDRs having the amino acid sequences of SEQ ID NOs:29-31;
(iv) one, two, or all three light chain CDRs having the amino acid sequences of SEQ ID NOs:34-36;
(v) one, two, or all three heavy chain CDRs having the amino acid sequences of SEQ ID NOs:39-41,
(vi) one, two, or all three light chain CDRs having the amino acid sequences of SEQ ID NOs:44-46,
(vii) one, two, or all three heavy chain CDRs having the amino acid sequences of SEQ ID NOs:49-51,
(viii) one, two, or all three light chain CDRs having the amino acid sequences of SEQ ID NOs:54-56
(ix) one, two, or all three heavy chain CDRs having the amino acid sequences of SEQ ID NOs:59-61, or
(x) one, two, or all three light chain CDRs having the amino acid sequences of SEQ ID NOs:64-66.

Embodiment 3

The ERFE-binding antibody, or ERFE-binding fragment thereof, of Embodiment 1, comprising an amino acid sequence that shares at least 80% sequence identity with the VH of SEQ ID NO:18 and an amino acid sequence that shares at least 80% sequence identity with the VL of SEQ ID NO:23.

Embodiment 4

The ERFE-binding antibody, or ERFE-binding fragment thereof, of Embodiment 1 or Embodiment 3, wherein the VH has an amino acid sequence that shares at least 90% sequence identity with the amino acid sequence of SEQ ID NO:18.

Embodiment 5

The ERFE-binding antibody, or ERFE-binding fragment thereof, of Embodiment 1 or Embodiment 3, wherein the VL has an amino acid sequence that shares at least 90% sequence identity with the amino acid sequence of SEQ ID NO:23.

Embodiment 6

The ERFE-binding antibody, or ERFE-binding fragment thereof, of Embodiment 2, wherein the antibody comprises one, two, or all three heavy chain CDRs having the amino acid sequences of SEQ ID NOs:19-21 and one, two, or all three light chain CDRs having the amino acid sequences of SEQ ID NOs:24-26.

Embodiment 7

An ERFE-binding antibody, or ERFE-binding fragment thereof, of Embodiment 1, comprising an amino acid sequence that shares at least 80% sequence identity with the VH of SEQ ID NO:28 or an amino acid sequence that shares at least 80% sequence identity with the VL of SEQ ID NO:33.

Embodiment 8

The ERFE-binding antibody, or ERFE-binding fragment thereof, of Embodiment 1 or Embodiment 7, wherein the VH has an amino acid sequence that shares at least 90% sequence identity with the amino acid sequence of SEQ ID NO:28.

Embodiment 9

The ERFE-binding antibody, or ERFE-binding fragment thereof, of Embodiment 1 or Embodiment 7, wherein the VL has an amino acid sequence that shares at least 90% sequence identity with the amino acid sequence of SEQ ID NO:33.

Embodiment 10

The ERFE-binding antibody, or ERFE-binding fragment thereof, of Embodiment 2, wherein the antibody comprises one, two, or all three heavy chain CDRs having the amino acid sequences of SEQ ID NOs:29-31 and one, two, or all three light chain CDRs having the amino acid sequences of SEQ ID NOs:34-36.

Embodiment 11

The ERFE-binding antibody, or ERFE-binding fragment thereof, of Embodiment 1, comprising an amino acid sequence that shares at least 80% sequence identity with the VH of SEQ ID NO:38 and an amino acid sequence that shares at least 80% sequence identity with the VL of SEQ ID NO:43.

Embodiment 12

The ERFE-binding antibody, or ERFE-binding fragment thereof, of Embodiment 1 or Embodiment 11, wherein the VH has an amino acid sequence that shares at least 90% sequence identity with the amino acid sequence of SEQ ID NO:38.

Embodiment 13

The ERFE-binding antibody, or ERFE-binding fragment thereof, of Embodiment 1 or Embodiment 11, wherein the VL has an amino acid sequence that shares at least 90% sequence identity with the amino acid sequence of SEQ ID NO:43.

Embodiment 14

The ERFE-binding antibody, or ERFE-binding fragment thereof, of Embodiment 2, wherein the antibody comprises one, two, or all three heavy chain CDRs having the amino acid sequences of SEQ ID NOs:39-41 and one, two, or all three light chain CDRs having the amino acid sequences of SEQ ID NOs:44-46.

Embodiment 15

The ERFE-binding antibody, or ERFE-binding fragment thereof, of Embodiment 1, comprising an amino acid sequence that shares at least 80% sequence identity with the VH of SEQ ID NO:48 and an amino acid sequence that shares at least 80% sequence identity with the VL of SEQ ID NO:53.

Embodiment 16

The ERFE-binding antibody, or ERFE-binding fragment thereof, of Embodiment 1 or Embodiment 15, wherein the VH has an amino acid sequence that shares at least 90% sequence identity with the amino acid sequence of SEQ ID NO:48.

Embodiment 17

The ERFE-binding antibody, or ERFE-binding fragment thereof, of Embodiment 1 or Embodiment 15, wherein the VL has an amino acid sequence that shares at least 90% sequence identity with the amino acid sequence of SEQ ID NO:53.

Embodiment 18

The ERFE-binding antibody, or ERFE-binding fragment thereof, of Embodiment 2, wherein the antibody comprises one, two, or all three heavy chain CDRs having the amino acid sequences of SEQ ID NOs:49-51 and one, two, or all three light chain CDRs having the amino acid sequences of SEQ ID NOs:54-56.

Embodiment 19

The ERFE-binding antibody, or ERFE-binding fragment thereof, of Embodiment 1, comprising an amino acid sequence that shares at least 80% sequence identity with the VH of SEQ ID NO:58 or an amino acid sequence that shares at least 80% sequence identity with the VL of SEQ ID NO:63.

Embodiment 20

The ERFE-binding antibody, or ERFE-binding fragment thereof, of Embodiment 1 or Embodiment 19, wherein the VH has an amino acid sequence that shares at least 90% sequence identity with the amino acid sequence of SEQ ID NO:58.

Embodiment 21

The ERFE-binding antibody, or ERFE-binding fragment thereof, of Embodiment 1 or Embodiment 19, wherein the VL has an amino acid sequence that shares at least 90% sequence identity with the amino acid sequence of SEQ ID NO:63.

Embodiment 22

The ERFE-binding antibody, or ERFE-binding fragment thereof, of Embodiment 2, wherein the antibody comprises one, two, or all three heavy chain CDRs having the amino acid sequences of SEQ ID NOs:59-61 and one, two, or all three light chain CDRs having the amino acid sequences of SEQ ID NOs:64-66.

Embodiment 23

An ERFE-binding antibody, or ERFE-binding fragment thereof, comprising a VH and a VL, wherein the VH comprises the amino acid sequence of SEQ ID NO:18, 28, 38, 48, or 58 and the VL comprises the amino acid sequence of SEQ ID NO:23, 33, 43, 53, or 63.

Embodiment 24

An ERFE-binding antibody, or ERFE-binding fragment thereof, comprising the VH of SEQ ID NO: 18, 28, 38, 48, or 58 or the VL of SEQ ID NO: 23, 33, 43, 53, or 63.

Embodiment 25

An ERFE-binding antibody, or ERFE-binding fragment thereof, comprising a CDRH1 having the amino acid sequence of SEQ ID NO: 19, 29, 39, 49, or 59.

Embodiment 26

An ERFE-binding antibody, or ERFE-binding fragment thereof, comprising a CDRH2 having the amino acid sequence of SEQ ID NO: 20, 30, 40, 50, or 60.

Embodiment 27

An ERFE-binding antibody, or ERFE-binding fragment thereof, comprising a CDRH3 having the amino acid sequence of SEQ ID NO: 21, 31, 42, 52, or 62.

Embodiment 28

An ERFE-binding antibody, or ERFE-binding fragment thereof, comprising a CDRL1 having the amino acid sequence of SEQ ID NO: 24, 34, 44, 54, or 64.

Embodiment 29

An ERFE-binding antibody, or ERFE-binding fragment thereof, comprising a CDRL2 having the amino acid sequence of SEQ ID NO: 25, 35, 45, 55, or 65.

Embodiment 30

An ERFE-binding antibody, or ERFE-binding fragment thereof, comprising a CDRL3 having the amino acid sequence of SEQ ID NO: 26, 36, 46, 56, or 66.

Embodiment 31

The ERFE-binding antibody, or ERFE-binding fragment thereof, of one of Embodiments 1-30, wherein the antibody is a chimeric antibody, a humanized antibody, or an antibody fragment.

Embodiment 32

An assay for detecting the presence of and/or measuring the amount of an erythroferrone (ERFE) protein in a sample, comprising: contacting the sample with a first antibody to form a first antibody-ERFE complex; and then detecting the presence of and/or measuring the amount of second antibody bound to the first antibody-ERFE complex, wherein the first antibody and the second antibody are not the same, thus determining the presence, and or the amount, of an ERFE protein in the sample.

Embodiment 33

The assay of Embodiment 32, wherein the assay comprises an ELISA assay.

Embodiment 34

The assay of Embodiment 32, wherein the sample is a serum sample.

Embodiment 35

The assay of Embodiment 32, wherein the first and second antibodies specifically recognize an ERFE polypeptide comprising, consisting essentially of, or consisting of a sequence of at least one of SEQ ID Nos: 1 and/or 3-16.

Embodiment 36

The assay of Embodiment 32, wherein the first antibody is selected from monoclonal antibodies 9B12, 17A5, 17E5, 2D2, 4C1, 6H9, 7H4, 9C7, 14B2, and 14D9, or an ERFE-binding fragment thereof.

Embodiment 37

The assay of Embodiment 32, wherein the first antibody is selected from the antibodies of any one of Embodiments 1-31.

Embodiment 38

The assay of Embodiment 32, wherein the first antibody is 4C1 or an ERFE-binding fragment thereof.

Embodiment 39

The assay of any one of Embodiments 32-38, wherein the first antibody is coated on a solid support.

Embodiment 40

The assay of Embodiment 39, wherein the solid support is an ELISA plate.

Embodiment 41

The assay of Embodiment 32, wherein the detecting step comprises contacting a first antibody-ERFE polypeptide complex with a second antibody, and wherein the second antibody is labeled.

Embodiment 42

The assay of Embodiment 41, wherein the second antibody is a labeled detection monoclonal antibody selected from 9B12, 17A5, 17E5, 2D2, 4C1, 6H9, 7H4, 9C7, 14B2, and 14D9

Embodiment 43

The assay of Embodiment 41, wherein the second antibody is a labeled detection antibody selected from the antibodies of any one of Embodiments 1-39.

Embodiment 44

The assay of Embodiment 41, wherein the second antibody is 2D2.

Embodiment 45

The assay of Embodiment 41, wherein the label is biotin.

Embodiment 46

The assay of Embodiment 41, wherein the label is horseradish peroxidase

Embodiment 47

A method of assessing erythropoiesis in a subject with disorder associated with ERFE or myonectin, comprising subjecting a sample from the subject with the assay of any one of Embodiments 32-46.

Embodiment 48

The method of Embodiment 47, wherein the disorder is a thalassemia.

Embodiment 49

The method of Embodiment 47, wherein the disorder is a cardiovascular disorder.

Embodiment 50

A method of assessing erythropoiesis in a subject with a disorder, comprising detecting erythroferrone in a sample from a subject with an antibody according to any one of Embodiments 1-31.

Embodiment 51

A kit for a sandwich immunoassay comprising a capture antibody and a detection antibody wherein:
i) the capture antibody is 17A5 and the detection antibody is 2D2, 4C1, or 7H4;
ii) the capture antibody is 2D2 and the detection antibody is 4C1, 7H4, 17A5, or 9B12;
iii) the capture antibody is 4C1 and the detection antibody is 2D2, 7H4, 17A5, or 9B12;
iv) the capture antibody is 7H4 and the detection antibody is 2D2, 4C1 17A5, or 9B12;
v) the capture antibody is 9B12 and the detection antibody is 2D2, 4C1, 17A5, or 7H4; or vii) the capture and detection antibodies are individually antibodies according to any one of Embodiments 14-44, wherein the capture and detection antibodies are not the same.

Embodiment 52

The kit of Embodiment 51, wherein the capture antibody and the detection antibody are different antibodies.

Embodiment 53

The kit of Embodiment 51 or 52, wherein the capture antibody is associated with a solid support.

Embodiment 54

The kit of any one of Embodiments 51-53, wherein the detection antibody is associated with a label.

Embodiment 55

The kit of Embodiment 54, wherein the label is biotin.

Embodiment 56

The kit of Embodiment 54, wherein the label is horseradish peroxidase.

Embodiment 57

The kit of Embodiment 55, further comprising streptavidin-horseradish peroxidase.

Embodiment 58

The kit of any one of Embodiments 51-57, further comprising a substrate.

Embodiment 59

The kit of any one of Embodiments 51-58, further comprising instructions for performing the assay.

EXAMPLES

Example 1. Monoclonal Sandwich ELISA for Serum Erythroferrone for Clinical Assessment of Ineffective Erythropoiesis The hallmark of β-thalassemia and other common genetic and acquired iron-loading anemias is ineffective erythropoiesis (IE; impaired blood production) that leads to debilitating anemia in the presence of iron overload. Recently discovered, erythroferrone (ERFE) is a hormone produced in developing red blood cells (RBCs) and has been shown to be a negative regulator of hepcidin, the master hormone regulating plasma iron levels, and to be highly elevated in β-thalassemia patients.

ERFE Antigen Production and Purification.

Cultured HEK cells were transiently transfected with cloned ERFE containing a FLAG-tag. Transfected HEK cells were expanded under permissive conditions for ERFE expression and media supernatants were collected and pooled for purification in an anti-FLAG column. While the antigen was recognized by anti-ERFE mAbs, the yield was low. A high-efficiency HEK cell line and a GenScript proprietary cloning vector (Piscataway, N.J.) for ERFE increased production efficiency yielded purified ERFE at ~5 mg/L.

Plasmon Resonance Evaluation of ERFE mAbs.

The specificity, affinity, and kinetics of antibody binding to ERFE antigen is then determined. This approach enables selection of high-affinity mAbs for ERFE and the selection of the optimal pair of capture and detection mAbs for an ERFE sandwich ELISA. Initial screen of all monoclonal antibody candidates is performed using ELISA with ERFE-coated 96-well plates. Because epitope accessibility or its conformation may change upon immobilization on plastic, ERFE antigen is immobilized on ELISA plates at different concentrations. Hybridoma supernatants having high titers on either plate are selected based on this assay. For surface plasmon resonance analysis, highly purified antibodies are coated on Biacore sensor chips. To ensure capturing antibodies in an oriented manner, Fc-specific chips (protein A/G sensor chip CM5) are used. Expressed and purified ERFE antigen is injected at a range of concentrations (nM to mM), and binding interactions studied under a range of buffer conditions. As a control, BSA or non-specific antibodies are immobilized onto the reference surface under the same conditions to correct for instrument and buffer artifacts.

Dissociation (koff) and association (kon) rate constants, and other binding parameters are obtained using the BIAevaluation version 3.2 software provided by the manufacturer.

This experiment is also performed in the reverse configuration, in which the chip was coated with ERFE antigen and mAb solution is injected. ERFE antigens are immobilized on the chip via —$NH_2$ or —COOH groups, and a related protein is used as a control. Finally, the ability of pairs of antibodies to interact with ERFE is tested using promising candidate pairs identified. One antibody was anchored on an Fc-Chip, ERFE added, and a second antibody floated over the chip. Antibody pairs yielding the highest affinity interactions are selected. Controls include experiments where ERFE is substituted with other related or unrelated proteins.

Monoclonal Antibody Production.

Nine ERFE-specific mouse monoclonal hybridomas were identified by limited dilution and have confirmed ability to secrete a suitable quantity of ERFE-specific IgG antibody (~1 μg IgG/ml TC media). Multiple aliquots of each of the antibodies were expanded and stored on in liquid nitrogen.

A subset of the anti-ERFE antibodies were identified following screening of suitable mAb pairs by sandwich ELISA. Selected hybridomas were assessed for mAb production efficiency in tissue culture flasks and 10-100 ml hollow fiber bioreactors to determine whether these production conditions affect assay performance.

For in vitro growth studies, mAbs 2D2 and 4C1 were grown in serum free media using two FiberCell Systems hollow fiber bioreactors (Frederick, Md.) housed in a humidified, temperature controlled $CO_2$ tissue culture incubator. Flow rates were adjusted to 25-50 ml/min to achieve high milligram quantities of antibody in 30 days. mAbs in bioreactor media harvested daily were pooled and affinity purified on 5 ml Protein G columns and desalted against PBS using a HiPrep 26/10 desalting column (GE Healthcare, Uppsala, Sweden). 96-well EIA plates were coated overnight with the purified capture antibodies. These capture mAbs were each tested with each detection mAb labeled with biotin in small quantities, for simultaneous binding activity by ELISA.

Scaling bioreactor production was also assessed to determine whether hybridoma media composition and production methods conditions influence the antigen antibody interaction of the anti-ERFE mAbs. Technical metrics of mAbs produced by different methods or scales were compared. Antibody production conditions may have nominal effects on assay performance.

Development of Methods and Materials for Production of ERFE mAb Coated Microtiter Plates.

All best performing antibodies were affinity purified and underwent checkerboard optimization to determine the optimal antibody concentrations and conditions for passive adsorption of the mAbs to the 96-well microtiter plates. The microtiter plates were desiccated overnight using a temperature- and humidity-controlled incubator, individual plates were heat-sealed in a mylar pouch containing a 1 gram molecular sieve desiccant packet and stored at 4° C.

A research sandwich ELISA for ERFE using proprietary reagents has been developed. Plates were coated and blocked by passive adsorption of the mAbs using a high pH carbonate coating buffer. Several additional 96-well microtiter plate formats from different manufacturers were tested to determine the optimal concentrations and dilutions of the ERFE capture mAb that yielded the greatest signal to noise ratio with the least well-to-well variation in antibody binding (CV less than 5%).

Automation and Validation of a Clinical Assay for ERFE.

The existing ERFE mAb-based sandwich ELISA is a baseline ERFE ELISA from which the clinical assay will be validated. Clinical Laboratory Improvement Amendments (CLIA) and College of American Pathologists (CAP) guidelines are used to develop the assay on a fully integrated Beckman FX platform. The Beckman Platform is equipped with a DTX-880 detector, BioTek plate washer, and Cytomat 2C15 incubator and plate/tip hotel. Currently the sandwich ELISA has an excellent lower limit of detection (LLOD) and lower limit of quantitation (LLOQ) of 0.1 and 0.15 ng/ml, respectively. Automation will increase the dynamic range of the research ERFE sandwich ELISA and allow consistent measurement of ERFE in the low pg/ml or low ng/ml range. The inter-/intra-assay coefficients of variation (CVs) are improved, as well as improving the signal-to-noise ratio. Changes in sensitivity of the ERFE test was readily apparent by lower LLOD/LLOQ metrics in the automated Beckman FX ERFE test.

Assay development began with a standard curve prepared from ERFE antigen with a final concentration ranging from 0-50 ng/ml, from 0-40 ng/ml, from 0-30 ng/ml, from 0-20 ng/ml, or from 0-10 ng/ml. Since one desired feature of a mAb-based diagnostic device was to improve the lower limit of detection, studies were undertaken to ensure that samples were sufficiently diluted to fall within the linear range of detection. Assay selectivity was examined by the addition of known concentrations of ERFE in serum obtained from a panel of patients with diseases of ineffective erythropoiesis.

A panel of 292 first-time blood donors' serum samples from healthy human volunteers (equal distribution of males and females with normal laboratory levels of hemoglobin, ferritin, serum transferrin receptor and C-reactive protein) was utilized to establish the reference range of the automated FX ERFE test. Intra-assay precision was tested by measuring serum samples in replicate (n=6) on the same day and the coefficient of variation (CV) determined. Inter-assay reproducibility was determined by performing the assay on three different days with at least two operators and calculating the mean and median CV. Intra-batch and inter-batch assay variability was examined by repeating the experiments with plates manufactured from the same and different batches of reagents to ensure adherence to strict quality control standards required for assay validation studies.

Example 2. Production of Recombinant Human Erythroferrone Antigen

Figure 2A:
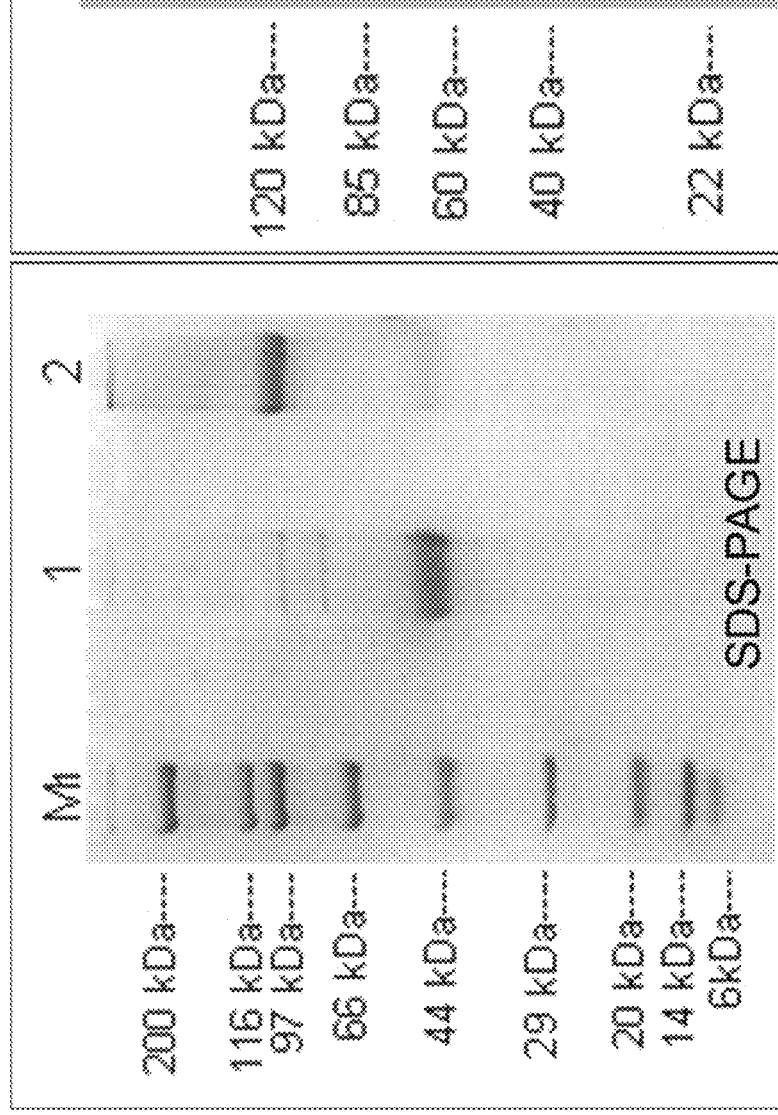
Figure 3A:
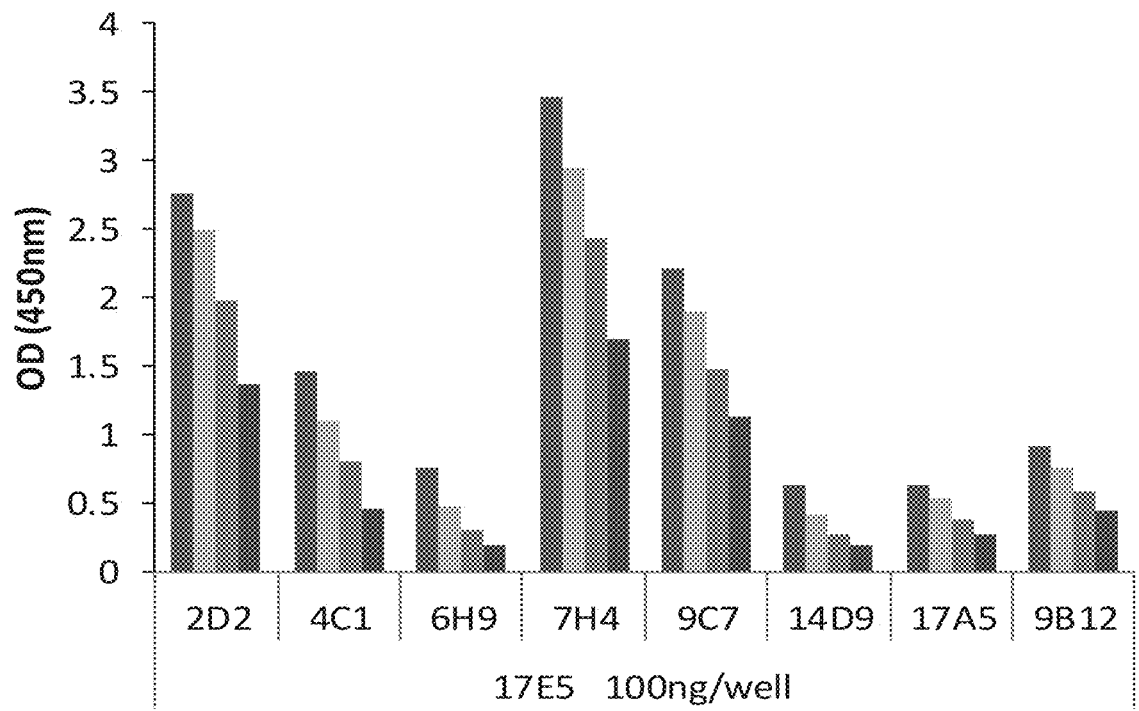
FIG. 3A-F depicts pair-wise screening with six monoclonal antibodies as the capture antibody (coated at 100 ng/well)
Figure 3B:
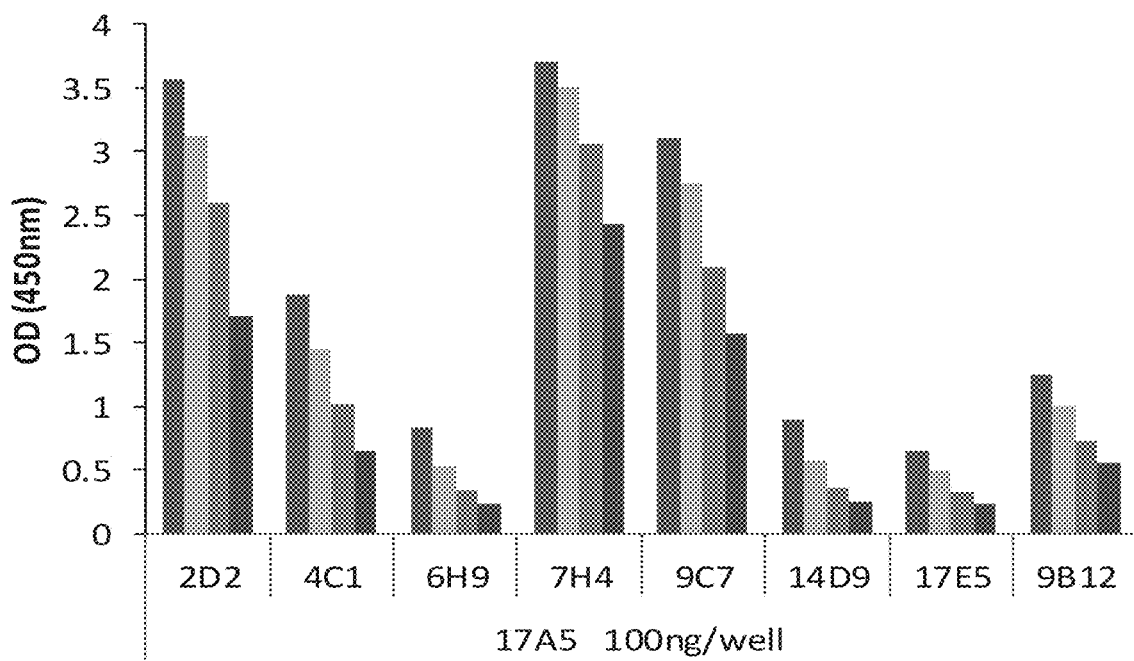
Figure 3C:
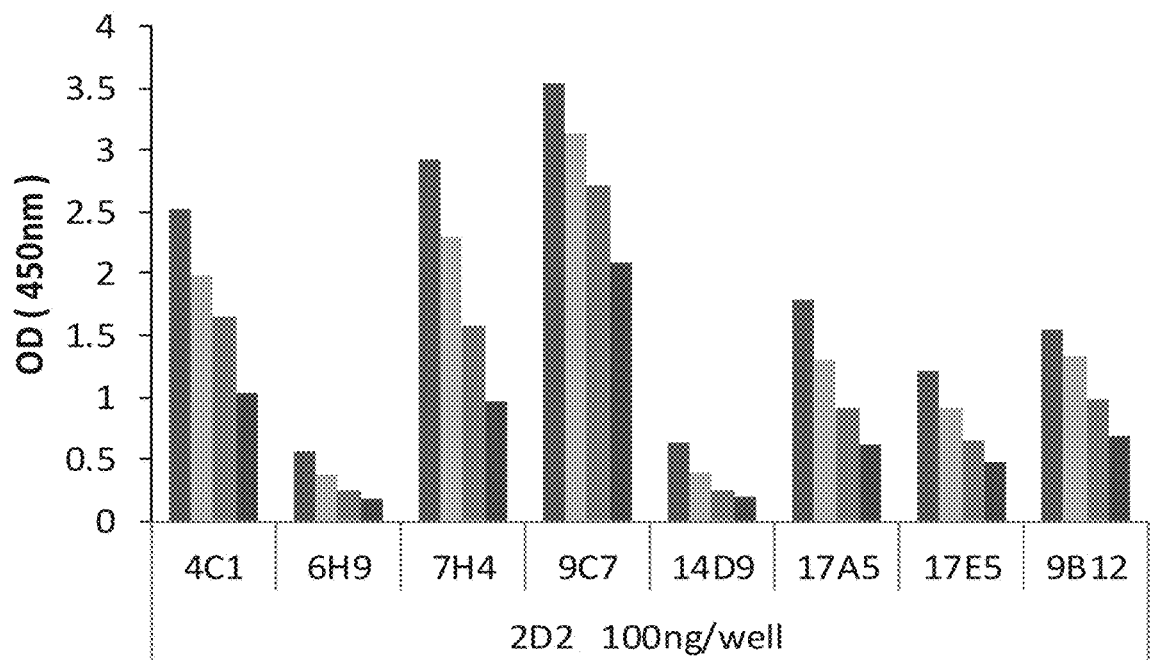
Figure 3D:
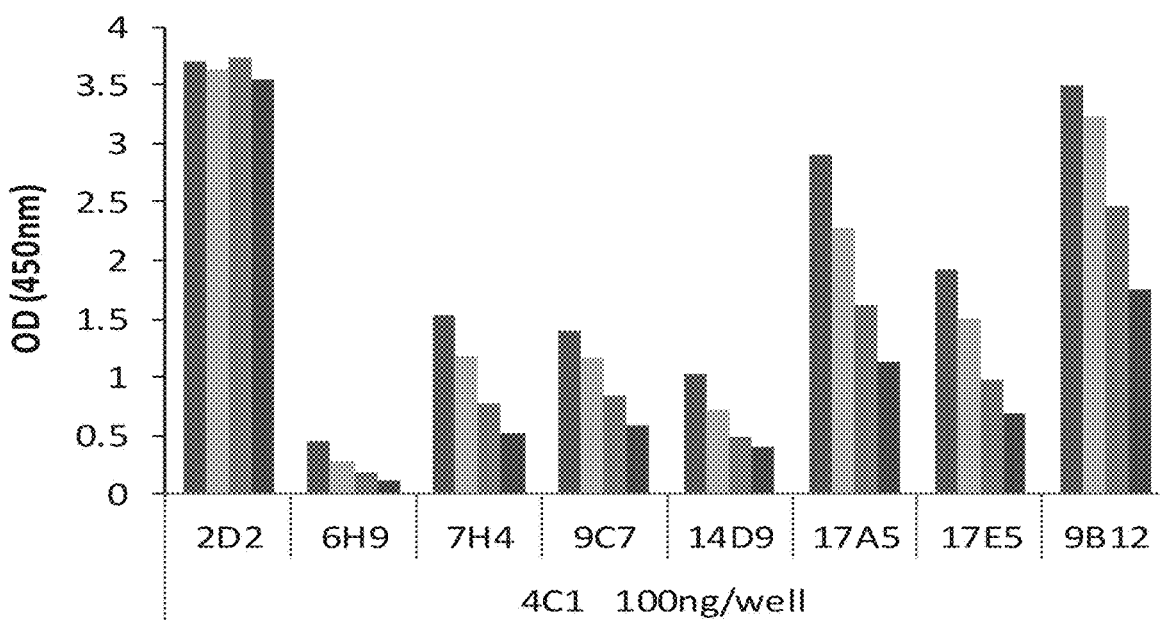
Figure 3E:
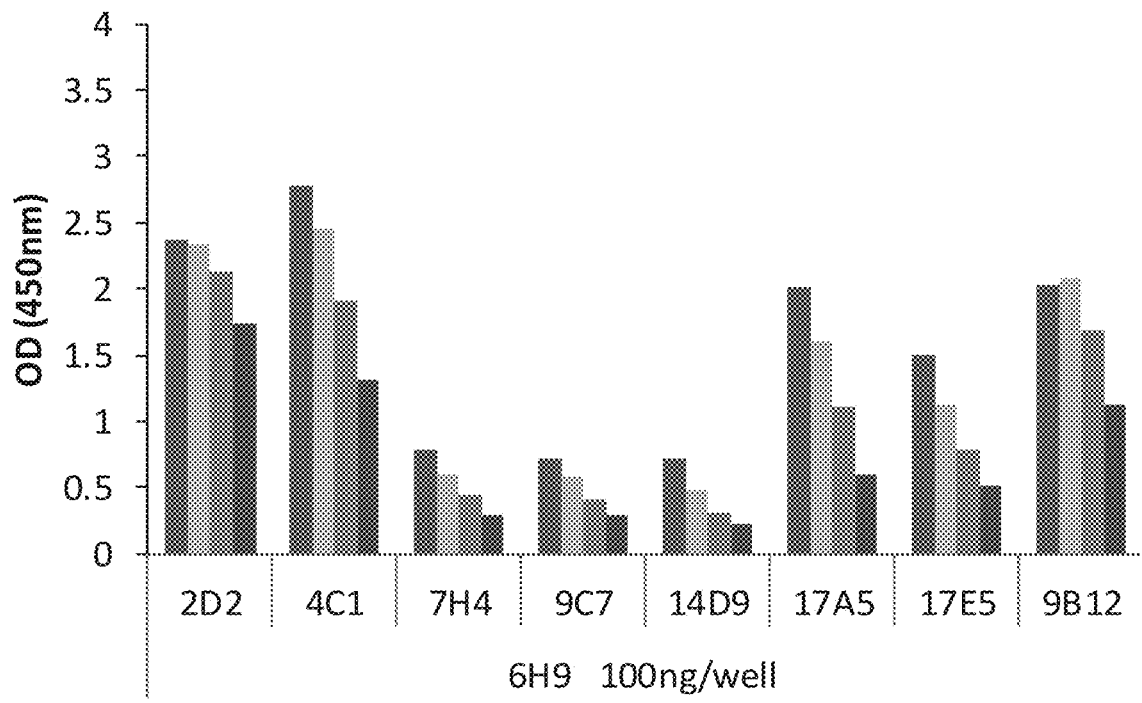
Figure 3F:
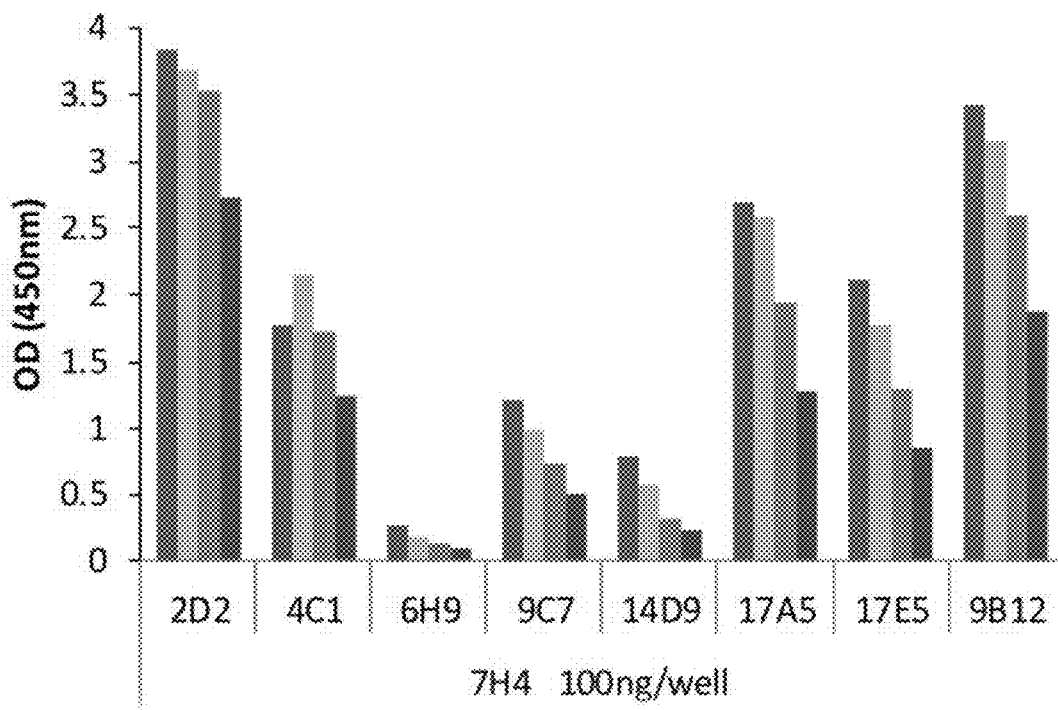

Following discovery of human ERFE, development of monoclonal antibodies necessary for a prototype sandwich ELISA were developed. HEK293F cells were transfected with either human ERFE or flag-tagged ERFE, cultured for 72 hours at 37° C. in a 5% $CO_2$ atmosphere, the supernatant harvested and antigen purified by anti-human ERFE polyclonal antibody immobilized to protein-G agarose beads or anti-Flag M2 affinity chromatography, respectively. Antigen activity and purity was confirmed by ELISA, SDS-PAGE electrophoresis and western blot, the protein concentration determined using a bicinchoninic protein assay (BCA, Thermo Scientific, Rockford, Ill.) and aliquots frozen at −80° C. Preliminary studies demonstrated a poor yield, ranging from 0.2-0.3 mg of recombinant ERFE antigen per liter of tissue culture supernatant. While the antigen was recognized by anti-ERFE mAbs, the yield was low. A high-efficiency HEK cell line and a GenScript proprietary cloning vector (Piscataway, N.J.) containing human ERFE or flag-tagged ERFE were used for ERFE production. The GenScript expression reagents and methods yielded purified ERFE at ~5 mg/L. This expression effort yielded 1 mg of total protein with ~70% purity (FIG. 2).

Example 3. Monoclonal Antibody and Hybridoma Production

Female BALB/c mice (n=5 animals, 6-8 weeks old) were immunized by repeated injection of recombinant human erythroferrone (ERFE) at multiple subcutaneous sites. Serum titer was monitored at 4 week intervals and each mouse that responded strongly to immunization was selected, and fusion was performed using a pool of lymph nodes and spleen. A total of 4 fusions were performed; twelve 96-well plates were seeded for each fusion, plates were incubated at 37° C. in a 5% $CO_2$ atmosphere for 4 days yielding approximately 4,600 viable hybridoma colonies available to screen.

Hybridomas that secreted human ERFE-specific antibody were identified by coating 96-well microplates with recombinant antigen, adding 100 μl of hybridoma tissue culture supernatant to each well and the presence of ERFE-specific antibody was detected by the addition of horseradish peroxidase-labelled goat anti-mouse IgG H+L chain antibody. After addition of TMB (3,3',5,5'-tetramethylbenzidine), the reaction was developed for 15 min, stopped with 0.5N $H_2SO_4$ and the absorbance (450 nm) measured. A total of 10 human ERFE-specific IgG hybridomas were identified (0.022% hit rate; 9B12, 17A5, 17E5, 2D2, 4C1, 6H9, 7H4, 9C7, 14B2, and 14D9); isotype analysis demonstrated that nine of the ERFE-specific hybridomas were $IgG_1$ (9B12, 17A5, 17E5, 4C1, 6H9, 7H4, 9C7, 14B2, and 14D9) and 1 was $IgG_{2a}$ (2D2). All hybridomas were subcloned by limiting dilution, their isotype reconfirmed, and multiple aliquots of each were frozen in liquid nitrogen.

The identified hybridomas were deposited in the patent depository of the American Type Culture Collection with the following accession numbers:

| | |
|---|---|
| 9B12 | PTA-123882 |
| 17A5 | PTA-123883 |
| 2D2 | PTA-123879 |
| 4C1 | PTA-123880 |
| 7H4 | PTA-123881 |

The antibodies from hybridomas 9B12, 17A5, 2D2, 4C1, and 7H4 were then sequenced. Total RNA was isolated from the hybridoma cells using TRIzol® reagent according to the manufacturer's instructions. Total RNA was then reverse-transcribed into cDNA using either isotype-specific antisense primers or universal primers using the PrimeScript™ 1st Strand cDNA Synthesis Kit. Antibody fragments of $V_H$, $V_L$, $C_H$ and $C_L$ were amplified according by rapid amplification of cDNA ends (RACE) using GenScript. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned and the consensus sequence was provided in Table 2.

TABLE 2

| SEQ ID NO. | Description | Amino Acid Sequence |
|---|---|---|
| 17 | 2D2 Heavy chain | MEWSWIFLFLLSGTAGVLSEVQLQQFGPELVKPGGSVKISCKA SGYTFTDYNMDWVKQSHGKSLEWIGDFNPNYDSSTYNQKFKGK ATLTVDKSSSTAYMELRSLTSEDTAVYYCARGMILYYGNSGSM DYWGQGTSVTVSSAKTTAPSVYPLAPVCGDTTGSSVTLGCLVK GYFPEPVTLTWNSGSLSSGVHTFPAVLQSDLYTLSSSVTVTSS TWPSQSITCNVAHPASSTKVDKKIEPRGPTIKPCPPCKCPAPN LLGGPSVFIFPPKIKDVLMISLSPIVTCVVVDVSEDDPDVQIS WFVNNVEVHTAQTQTHREDYNSTLRVVSALPIQHQDWMSGKEF KCKVNNKDLPAPIERTISKPKGSVRAPQVYVLPPPEEEMTKKQ VTLTCMVTDFMPEDIYVEWTNNGKTELNYKNTEPVLDSDGSYF MYSKLRVEKKNWVERNSYSCSVVHEGLHNHHTTKSFSRTPGK |
| 18 | 2D2 VH | EVQLQQFGPELVKPGGSVKISCKASGYTFTDYNMDWVKQSHGK SLEWIGDFNPNYDSSTYNQKFKGKATLTVDKSSSTAYMELRSL TSEDTAVYYCARGMILYYGNSGSMDYWGQGTSVTVSS |
| 19 | 2D2 CDRH1 | DYNMD |
| 20 | 2D2 CDRH2 | DFNPNYDSSTYNQKFKG |
| 21 | 2D2 CDRH3 | GMILYYGNSGSMDY |
| 22 | 2D2 Light chain | MKFPSQLLLFLLFRITGIMCDIQMTQSSSYLSVSLGGRVTITC KASDHINNWLAWYQQKPGNAPRLLISGATSLETGVPSRFSGSG SGKDYTLTIISLQTEDVATYYCQQYWNTPRTFGGGTKLEIKRA DAAPTVSIFPPSSEQLTSGGASVVCFLNNFYPKDINVKWKIDG SERQNGVLNSWIDQDSKDSTYSMSSTLTLIKDEYERHNSYTCE ATHKTSTSPIVKSFNRNEC |
| 23 | 2D2 VL | MKFPSQLLLFLLFRITGIMCDIQMTQSSSYLSVSLGGRVTITC KASDHINNWLAWYQQKPGNAPRLLISGATSLETGVPSRFSGSG SGKDYTLTIISLQTEDVATYYCQQYWNTPRTFGGGTKLEIK |
| 24 | 2D2 CDRL1 | KASDHINNWLA |
| 25 | 2D2 CDRL2 | GATSLET |

TABLE 2 -continued

| SEQ ID NO. | Description | Amino Acid Sequence |
|---|---|---|
| 26 | 2D2 CDRL3 | QQYWNTPRT |
| 27 | 4C1 Heavy chain | MAVLGLLFCLVTFPSCVLSQVQLKQSGPGLVQPSQSLSITCTV SGFSLTTYSIHWVRQSPGKGLEWLGVIWSGGSIDYNAAFISRL TITKDNSKSQVFFKMNSLQVNDTAIYYCARNVLTYYRYDVEAM DYWGQGTSVTVSSAKTTPPSVYPLAPGSAAQTNSMVTLGCLVK GYFPEPVTVTWNSGSLSSGVHTFPAVLQSDLYTLSSSVTVPSS TWPSETVICNVAHPASSTKVDKKIVPRDCGCKPCICTVPEVSS VFIFPPKPKDVLTITLTPKVTCVVVDISKDDPEVQFSWFVDDV EVHTAQTQPREEQFNSTFRSVSELPIMHQDWLNGKEFKCRVNS AAFPAPIEKTISKTKGRPKAPQVYTIPPPKEQMAKDKVSLTCM ITDFFPEDITVEWQWNGQPAENYKNTQPIMDTDGSYFVYSKLN VQKSNWEAGNTFTCSVLHEGLHNHHTEKSLSHSPGK |
| 28 | 4C1 VH | QVQLKQSGPGLVQPSQSLSITCTVSGFSLTTYSIHWVRQSPGK GLEWLGVIWSGGIDYNAAFISRLTITKDNSKSQVFFKMNSLQ VNDTAIYYCARNVLTYYRYDVEAMDYWGQGTSVTVSS |
| 29 | 4C1 CDRH1 | TYSIH |
| 30 | 4C1 CDRH2 | VIWSGGSIDYNAAFIS |
| 31 | 4C1 CDRH3 | NVLTYYRYDVEAMDY |
| 32 | 4C1 Light chain | MMSSAQFLGLLLLCFQGTRCDIQMTQTTSSLSASLGDRVTISC SASQGISNFLNWYQQKPDGTVKLLIYYTSNLHSGVPSRFSGSG SGTDYSLTVSNLEPEDIATYYCQQYSELPFTFGSGTKLVIKRA DAAPTVSIFPPSSEQLTSGGASVVCFLNNFYPKDINVKWKIDG SERQNGVLNSWIDQDSKDSTYSMSSTLTLIKDEYERHNSYTCE ATHKTSTSPIVKSFNRNEC |
| 33 | 4C1 VL | DIQMTQTTSSLSASLGDRVTISCSASQGISNFLNWYQQKPDGT VKLLIYYTSNLHSGVPSRFSGSGSGTDYSLTVSNLEPEDIATY YCQQYSELPFTFGSGTKLVIKRADAAPT |
| 34 | 4C1 CDRL1 | SASQGISNFLN |
| 35 | 4C1 CDRL2 | YTSNLHS |
| 36 | 4C1 CDRL3 | QQYSELPFT |
| 37 | 7H4 Heavy chain | MECNWILPFILSVTSGVYSEVQLQQSGTVVARPGASVKMSCKA SGYTFTTYWMHWVKQWPGQGLEWIGAIYPGNSDTTYNQKFKGK AKLTAVTSTSTAYMELSSLTNEDSAVYYCTREDFYNGYDAEFA YWGQGTLVTVSAAKTTPPSVYPLAPGSAAQTNSMVTLGCLVKG YFPEPVTVTWNSGSLSSGVHTFPAVLQSDLYTLSSSVTVPSST WPSETVTCNVAHPASSTKVDKKIVPRDCGCKPCICTVPEVSSV FIFPPKPKDVLTITLTPKVTCVVVDISKDDPEVQFSWFVDDVE VHTAQTQPREEQFNSTFRSVSELPIMHQDWLNGKEFKCRVNSA AFPAPIEKTISKTKGRPKAPQVYTIPPPKEQMAKDKVSLTCMI TDFFPEDITVEWQWNGQPAENYKNTQPIMDTDGSYFVYSKLNV QKSNWEAGNTFTCSVLHEGLHNHHTEKSLSHSPGK |
| 38 | 7H4 VH | EVQLQQSGTVVARPGASVKMSCKASGYTFTTYWMHWVKQWPGQ GLEWIGAIYPGNSDTTYNQKFKGKAKLTAVTSTSTAYMELSSL TNEDSAVYYCTREDFYNGYDAEFAYWGQGTLVTVSA |
| 39 | 7H4 CDRH1 | TYWMH |
| 40 | 7H4 CDRH2 | AIYPGNSDTTYNQKFKGKA |
| 41 | 7H4 CDRH3 | EDFYNGYDAEFAY |
| 42 | 7H4 Light chain | MMSSAQFLGLLLLCFQGTRCDIQMTQTTSSLSASLGDRVTISC RASQDISNYLSWYQQKPDGTVKLLIYSTSKLHPGVPPRFSGSG SGTDYSLTISNLEQEDIATYFCQQGSTLLRTFGGGTKLEIKRA DAAPTVSIFPPSSEQLTSGGASVVCFLNNFYPKDINVKWKIDG SERQNGVLNSWIDQDSKDSTYSMSSTLTLIKDEYERHNSYTCE ATHKTSTSPIVKSFNRNEC |
| 43 | 7H4 VL | DIQMTQTTSSLSASLGDRVTISCRASQDISNYLSWYQQKPDGT VKLLIYSTSKLHPGVPPRFSGSGSGTDYSLTISNLEQEDIATY FCQQGSTLLRTFGGGTKLEIKRADAAPT |
| 44 | 7H4 CDRL1 | RASQDISNYLS |

TABLE 2-continued

| SEQ ID NO. | Description | Amino Acid Sequence |
|---|---|---|
| 45 | 7H4 CDRL2 | STSKLHP |
| 46 | 7H4 CDRL3 | QQGSTLLRT |
| 47 | 9B12 Heavy chain | MGWSRIFLFLLSIIAGVHCQVQLQQSGPELVKPGASVRISCKASGYTFTSYYIHWVKQRPGQGLEWIAWIYPGNVNTEYNEKFKGKATLTADESSSTAYMQLSSLTSEDSAVFFCAREGITTNALDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDCGCKPCICTVPEVSSVFIFPPKPKDVLTITLTPKVTCVVVDISKDDPEVQFSWFVDDVEVHTAQTQPREEQFNSTFRSVSELPIMHQDWLNGKEFKCRVNSAAFPAPIEKTISKTKGRPKAPQVYTIPPPKEQMAKDKVSLTCMITDFFPEDITVEWQWNGQPAENYKNTQPIMDTDGSYFVYSKLNVQKSNWEAGNTFTCSVLHEGLHNHHTEKSLSHSPGK |
| 48 | 9B12 VH | QVQLQQSGPELVKPGASVRISCKASGYTFTSYYIHWVKQRPGQGLEWIAWIYPGNVNTEYNEKFKGKATLTADESSSTAYMQLSSLTSEDSAVFFCAREGITTNALDYWGQGTSV |
| 49 | 9B12 CDRH1 | SYYIH |
| 50 | 9B12 CDRH2 | WIYPGNVNTEYNEKFKG |
| 51 | 9B12 CDRH3 | EGITTNALDY |
| 52 | 9B12 Light chain | MMSSAQFLGLLLFCFQGTRCDIQMTQTTSSLSASLGDRVTISCRASQDISNYLNWYQQKPDGTVKLLIYYTSRLYSGVPSRFSGNGSGSDYSLTISNLEQEDIATYFCQQGHTLWTFGGGTKLEIKRADAAPTVSIFPPSSEQLTSGGASVVCFLNNFYPKDINVKWKIDGSERQNGVLNSWIDQDSKDSTYSMSSTLTLIKDEYERHNSYTCEATHKTSTSPIVKSFNRNEC |
| 53 | 9B12 VL | DIQMTQTTSSLSASLGDRVTISCRASQDISNYLNWYQQKPDGTVKLLIYYTSRLYSGVPSRFSGNGSGSDYSLTISNLEQEDIATYFCQQGHTLWTFGGGTKLEIK |
| 54 | 9B12 CDRL1 | RASQDISNYLN |
| 55 | 9B12 CDRL2 | YTSRLYS |
| 56 | 9B12 CDRL3 | QQGHTLWT |
| 57 | 17A5 Heavy chain | MGWSSIILFLVATATGVHSQVQLQQPGSVLVRPGASVKLSCKASGYTFTSYWMHWAKQRPGQGLEWIGEIHPKSGDTNHNEKFKGKATLTVDTSSNTAYVDLSSLTSEDSAVYYCAREGITTVGFDLWGAGTTVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDCGCKPCICTVPEVSSVFIFPPKPKDVLTITLTPKVTCVVVDISKDDPEVQFSWFVDDVEVHTAQTQPREEQFNSTFRSVSELPIMHQDWLNGKEFKCRVNSAAFPAPIEKTISKTKGRPKAPQVYTIPPPKEQMAKDKVSLTCMITDFFPEDITVEWQWNGQPAENYKNTQPIMDTDGSYFVYSKLNVQKSNWEAGNTFTCSVLHEGLHNHHTEKSLSHSPGK |
| 58 | 17A5 VH | QVQLQQPGSVLVRPGASVKLSCKASGYTFTSYWMHWAKQRPGQGLEWIGEIHPKSGDTNHNEKFKGKATLTVDTSSNTAYVDLSSLTSEDSAVYYCAREGITTVGFDLWGAGTTVTVSS |
| 59 | 17A5 CDRH1 | SYWMH |
| 60 | 17A5 CDRH2 | EIHPKSGDTNHNEKFKG |
| 61 | 17A5 CDRH3 | EGITTVGFDL |
| 62 | 17A5 Light chain | MDFQVQIFSFLLISASVIISRGQIVLIQSPAIMSASPGQKVILTCSASSSVSYMNWVQQKSGTSPKRWIYDTSKLASGVPARFSGSGSGTSYSLTISSVEAEDAATYYCQQWSSHPYTFGGGTKLEIKRADAAPTVSIFPPSSEQLTSGGASVVCFLNNFYPKDINVKWKIDGSERQNGVLNSWIDQDSKDSTYSMSSTLTLIKDEYERHNSYTCEATHKTSTSPIVKSFNRNEC |
| 63 | 17A5 VL | QIVLTQSPAIMSASPGQKVTLTCSASSSVSYMNWVQQKSGTSPKRWIYDTSKLASGVPARFSGSGSGTSYSLTISSVEAEDAATYYCQQWSSHPYTFGGGTKLEIK |
| 64 | 17A5 CDRL1 | SASSSVSYMN |

TABLE 2 -continued

| SEQ ID NO. | Description | Amino Acid Sequence |
|---|---|---|
| 65 | 17A5 CDRL2 | DTSKLAS |
| 66 | 17A5 CDRL3 | QQWSSHPYT |

Studies were initiated to identify the best performing antibody pairs for development of a monoclonal antibody sandwich ELISA specific for human ERFE. Based on binding characteristics of the biotinylated mAbs to captured ERFE, 9 clones were resuscitated from liquid nitrogen, seeded into 6-well tissue culture plates, grown to confluency using DMEM containing 10% fetal calf serum and gradually acclimated to serum free medium over several expansions. Following acclimation, each murine hybridoma was expanded into T75 then T150 tissue culture flasks to produce approximately 1 liter of culture supernatant. Monoclonal antibody (mAb) was purified from the supernatant using a 1 ml HiTrap™ Protein G column (GE Healthcare, Uppsala, Sweden) and aliquots stored at −20° C. Each mAb was labelled with biotin using EZ-Link Sulfo-NHS-LC-Biotinylation chemistry (Thermo Scientific, Rockford, Ill.). ELISA plates were coated overnight with 100 ng/well of unlabeled capture mAb, recombinant human FLAG-ERFE (150, 75, 37.5, 18.75 ng/well) was incubated for 60 min, washed to remove unbound antigen and biotinylated mAb (150 ng/well) was added to each well and incubated for an additional hour. Antibody binding was detected with the addition of streptavidin-HRP followed TMB, the reaction was developed for 15 min, signal was halted and absorbance was measured at 450 nm. Nine different antibodies were tested as capture antibodies and eight biotinylated antibodies were tested as detection antibodies. Seventy-two different combinations were tested. Preliminary analysis has demonstrated that multiple antibody pairs can capture and detect recombinant human ERFE from the nine mAbs selected for pair wise comparison (FIG. 3A-F).

Figure 4A:
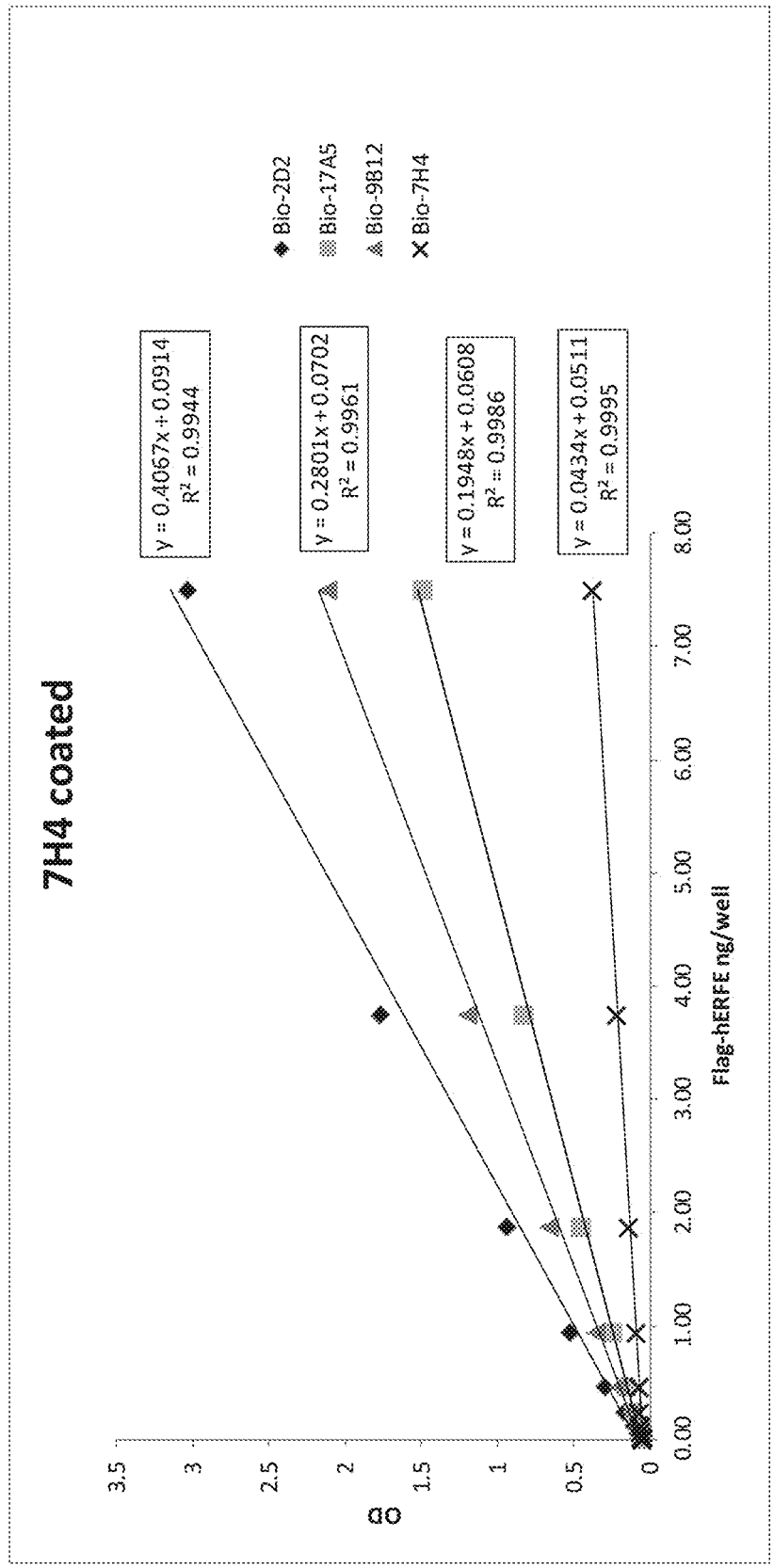
FIG. 4A-C depicts an anti-hERFE sandwich ELISA assay conducted with three different coating antibodies (7H4 [FIG. 4A], 17A5 [FIG. 4B], and 4C1 [FIG. 4C]) and four different biotinylated detection antibodies (2D2, 17A5, 9B12, and 4C1). Regardless of the capture antibody used, some detection antibodies gave a greater slope over the range of ERFE concentrations tested, despite the excellent correlation coefficients for all detection antibodies.
Figure 4B:
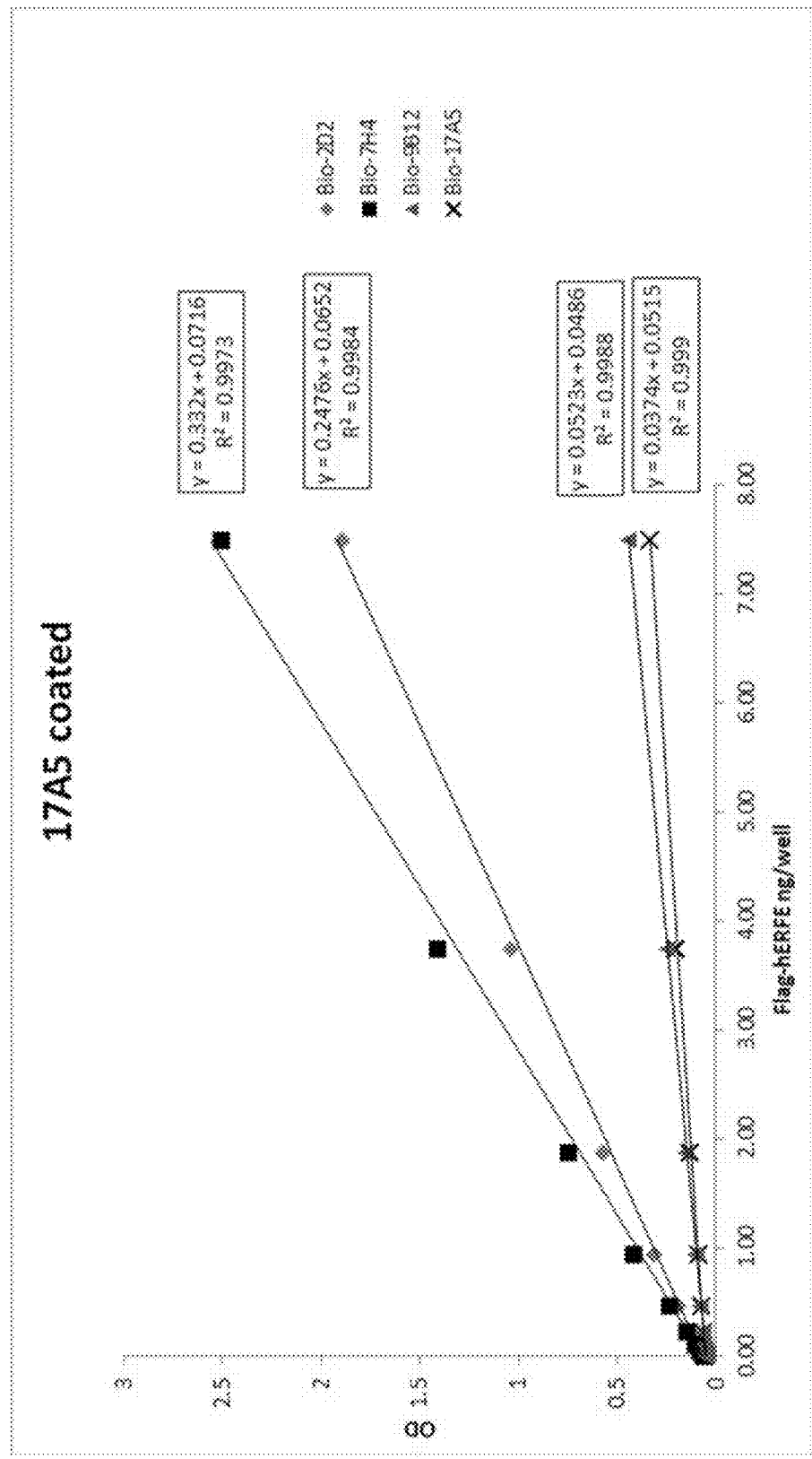
Figure 4C:
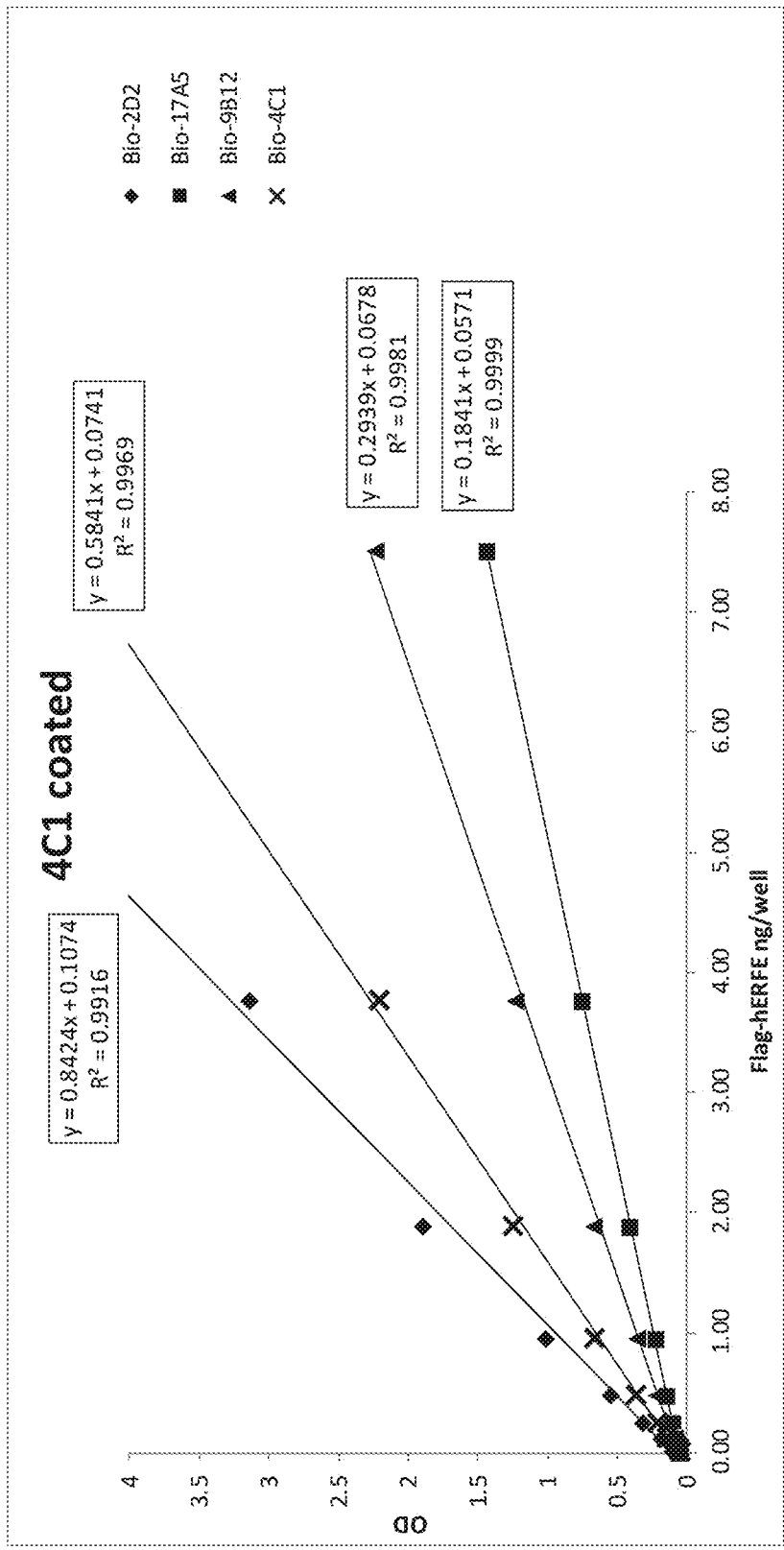

Additional anti-ERFE sandwich assay experiments were conducted with three different coating antibodies, 7H4, 17A5, and 4C1, and four different biotinylated detection antibodies 2D2, 17A5, 9B12, and 4C1 (FIG. 4A-C). As depicted in FIG. 4, regardless of the capture antibody tested, the regression equation generated with each detection antibody displayed a distinct slope indicating that each detection antibody possesses a different binding affinity for ERFE captured by the coating antibody. This characteristic is important for sandwich ELISA development because greater binding affinity results in a more sensitive assay. Furthermore, a greater slope is desired because antigen detection is optimal over the ERFE concentrations tested, despite the fact that the correlation coefficients for each regression equation were considered excellent (R2 values ranged from 0.9944 to 0.9999). Taken together, this approach empirically identified candidate antibody pairs to be considered for further assay development.

Example 4. Monoclonal Sandwich ELISA

Figure 5A:
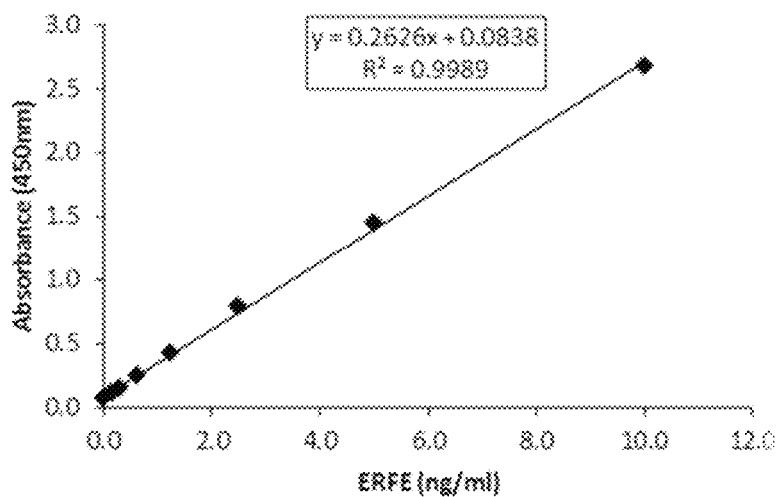
FIG. 5A-B depicts an eight-point standard curve generated using a prototype monoclonal sandwich ELISA (mAb 4C1 as capture antibody and mAb 2D2 as detection antibody), depicted graphically in a linear (FIG. 5A) and logarithmic (FIG. 5B) plot. Note the excellent distinction between the points in the lower aspect of the standard curve (FIG. 5B), giving optimum resolution of ERFE concentration measured in serum.
Figure 5B:
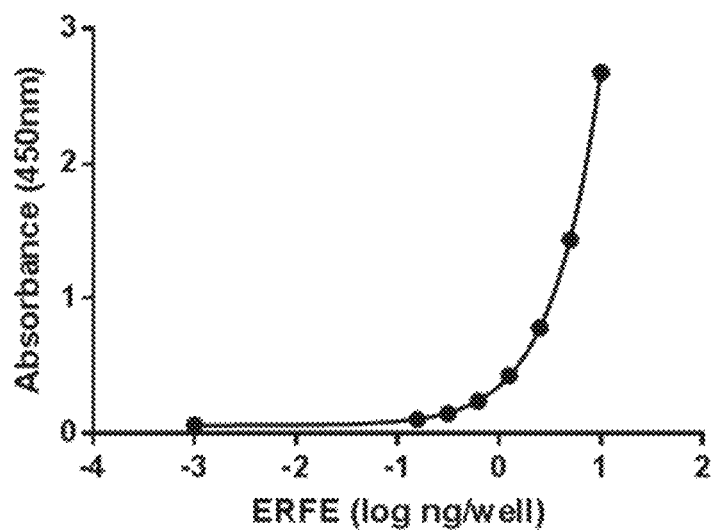

After querying all possible combinations of capture and detection antibodies for binding activity, mAbs 4C1 and 2D2 were selected as the capture and detection antibody, respectively, for further assay optimization. Preliminary 'checkerboard' studies with mAb 4C1 desiccated onto 96-well ELISA plates, identified optimal concentrations of capture antibody, and ERFE antigen for an 8-point standard curve, and streptavidin-HRP to quantify binding and detection of ERFE in serum. The standard curve was constructed with eight ERFE concentrations (10.0, 5.0, 2.5, 1.25, 0.63, 0.31, 0.16, 0.00 ng/ml) and produced a maximum absorbance ranging from 2.0-2.2 with background signal less than 0.05 absorbance units (FIG. 5). This prototype sandwich ELISA has a lower limit of detection (LLOD) and lower limit of quantitation (LLOQ) of 0.15 and 0.17 ng/ml, respectively.

Further, the assay was evaluated with two versions of flag-hERFE in the sandwich assay with 7H4 as capture antibody and biotinylated 2D2 as detection antibody which provided similar results further validating the assay.

Using this prototype assay studies were performed to determine the reference range of human ERFE by testing serum from 110 healthy first-time blood donors with normal iron status (determined by assessment of ferritin, plasma iron, and transferrin saturation). As expected in healthy individuals, serum ERFE was low (mean 0.83 ng/ml), and ranged from 0.15 to 3.94 ng/ml (5 and 95% confidence intervals, Table 3).

TABLE 3

| Donors with Normal Iron Status | Serum ERFE (ng/ml) | | |
|---|---|---|---|
| | Mean | 5% | 95% |
| All | 0.83 | 0.15 | 3.94 |
| Female | 0.63 | 0.15 | 2.18 |
| Male | 1.08 | 0.15 | 6.10 |

Figure 9:
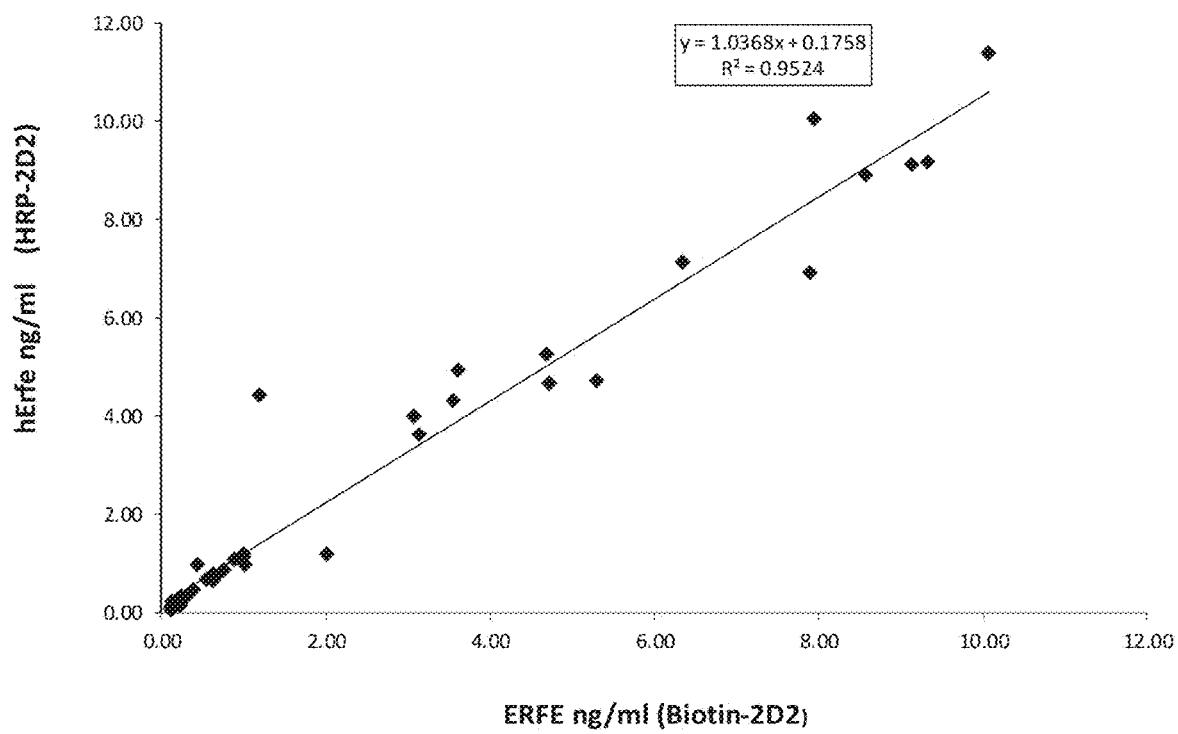
FIG. 9 depicts the relationship between endogenous ERFE measured in human serum samples (n=38) using either HRP-labeled 2D2 or biotinylated 2D2 detection antibody. This indicates that direct labelling of the detection antibody with HRP gives comparable serum ERFE concentrations compared to using a biotinylated detection antibody.

A further assay was conducted with 4C1 capture antibody and 2D2 detection antibody labeled with either biotin or horseradish peroxidase (HRP). The 2D2-biotin wells were further incubated with streptavidin-HRP and then all wells were then reacted with TMB. As shown in FIG. 9, detection antibodies labeled with biotin and HRP were substantially equivalent in their ability to detect ERFE in serum samples.

Example 5. Clinical Assessment of ERFE to Understand Ineffective Erythropoiesis

Figure 6:
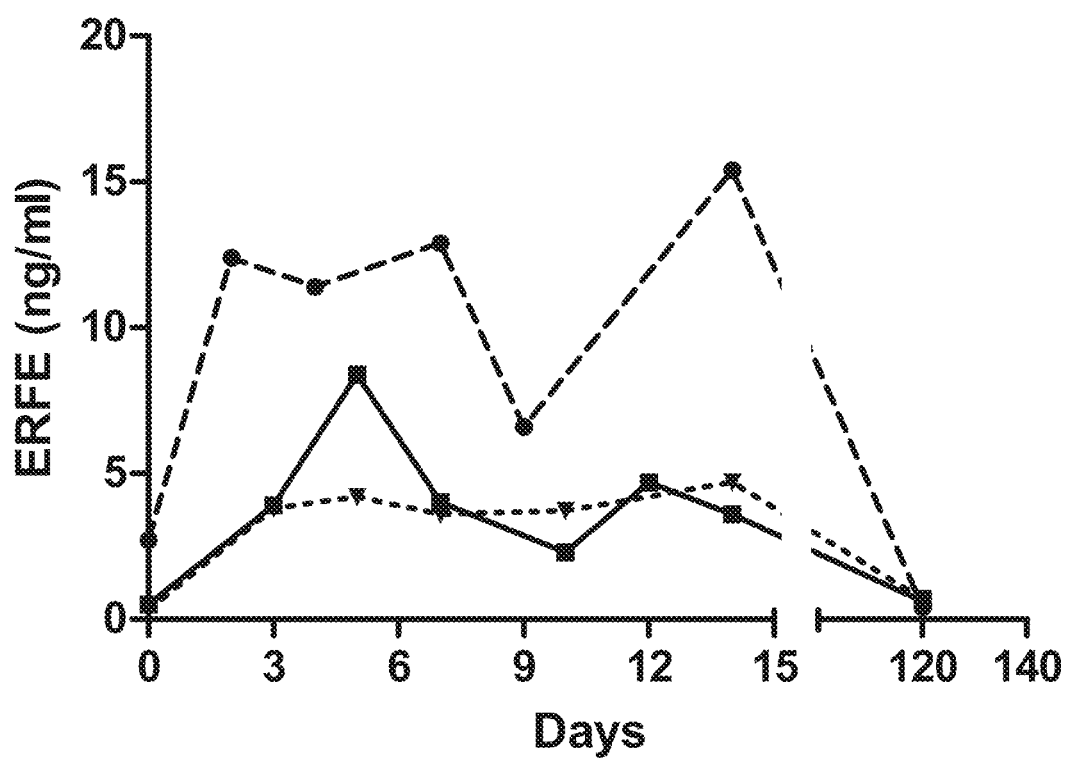
FIG. 6 depicts the effect of plasma- or platelet-apheresis on human serum ERFE expression (n=3 patients; solid, dotted, or dashed line). Serum ERFE was elevated at 2 days and remained above baseline levels for 14 days but all patients returned to baseline ERFE levels by 120 days post-apheresis.

The effect of blood donation on human serum ERFE concentration was determined. Three donors underwent platelet and plasma-apheresis at baseline and sera was obtained at baseline and at day 120 days post-apheresis and at least five times from days 2-14 post-apheresis. It was estimated that each patient lost ~30 ml of erythrocytes during the apheresis procedure. As expected, serum ERFE was elevated in each patient from baseline within the first 2 days post-apheresis and remained elevated through 14 days post-apheresis, but by 120 days following apheresis, serum ERFE returned to baseline levels (FIG. 6).

Figure 7:
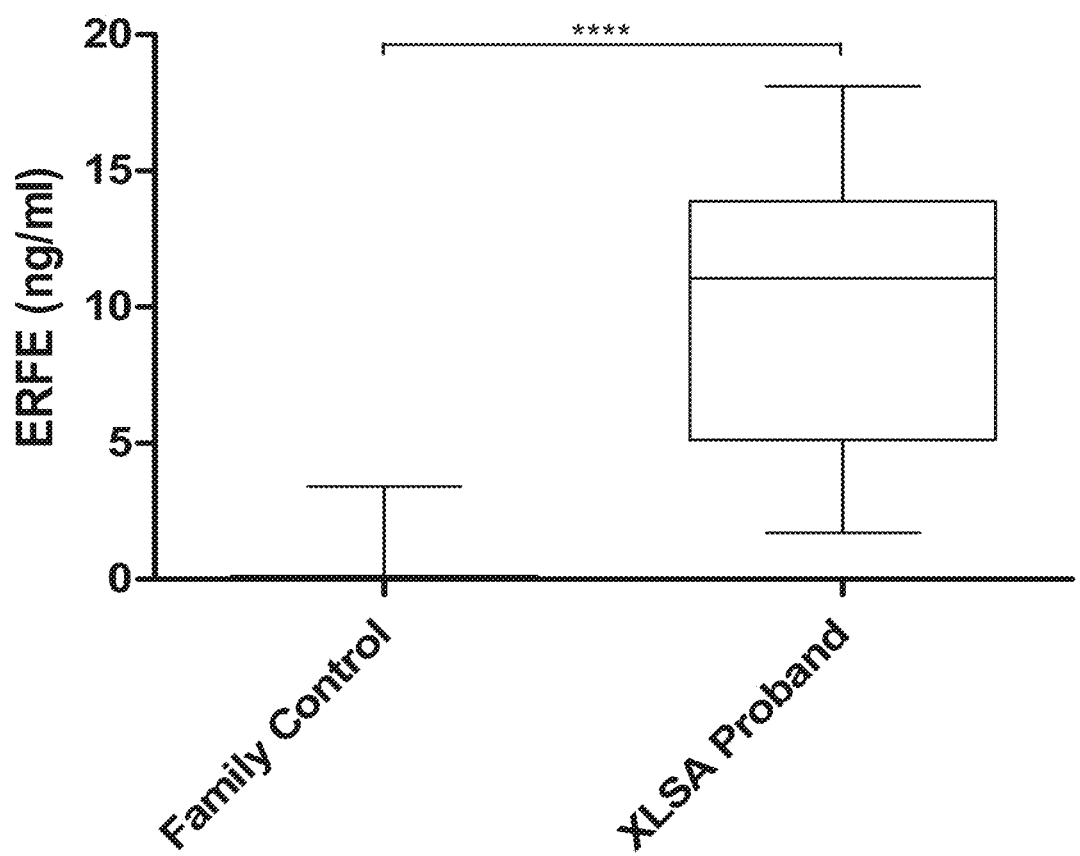
FIG. 7 depicts serum ERFE concentrations in patients with X-linked sideroblastic anemia (n=11, XLSA proband), compared to their family controls (n=15). The median ERFE concentration in the XLSA patients and controls were 10.8 and 0.1 ng/ml, respectively. Legend: **** $p<0.0001$.

Next, the hypothesis that serum ERFE concentrations would be elevated in blood disorders associated with ineffective erythropoiesis was tested. Serum samples were obtained from X-linked sideroblastic anemia patients (XLSA proband) and 15 of their family members (Family Control). Nine of the XLSA proband patients had a point mutation in the ALAS2 gene and two had α-globin duplications. Serum ERFE was measured in the XLSA proband and control groups and it was discovered that ERFE was significantly elevated in the XLSA proband group relative to familial controls (FIG. 7). Interestingly, serum ERFE in the family members (controls) had concentrations similar to first time healthy blood donors.

Figure 8:
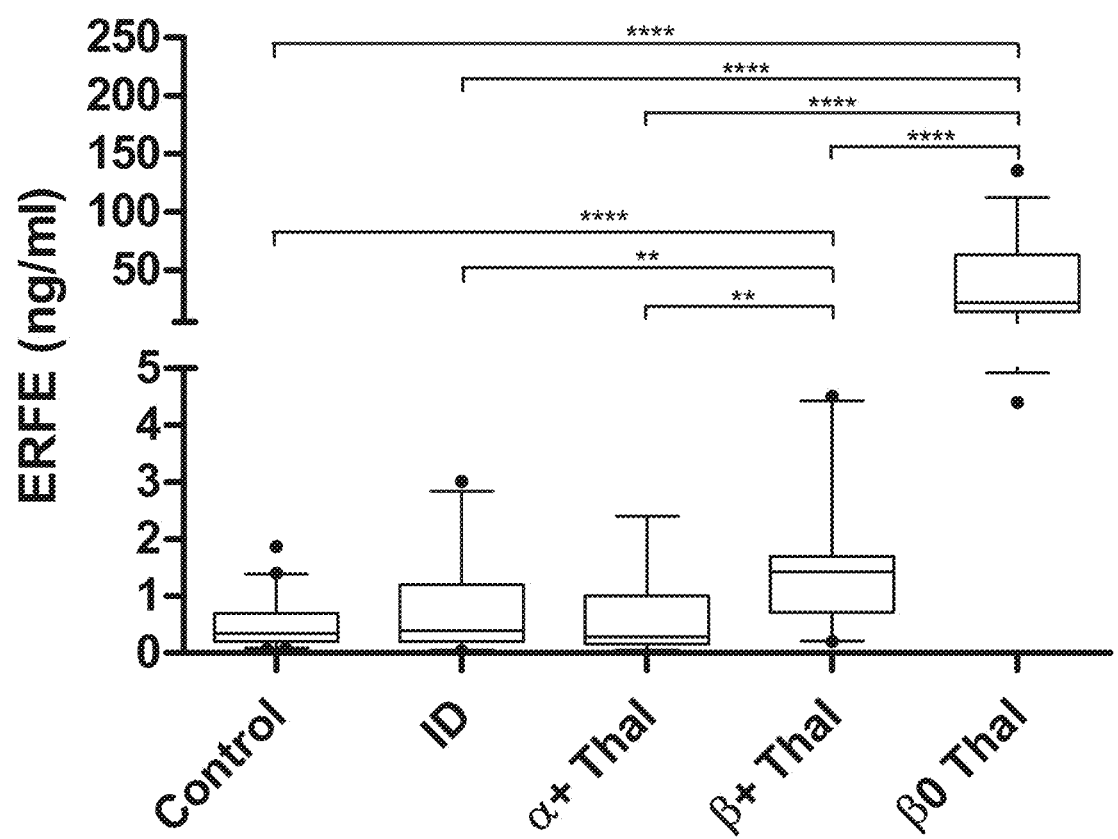
FIG. 8 depicts ERFE in iron-deficient and thalassemic patients. Serum ERFE was measured in control (n=47) and iron deficient (ID, n=22) donors, and α+-thalassemia (n=15), β+-thalassemia (n=20), and β0-thalassemia (n=27) patients. The median ERFE in controls was 0.4 ng/ml while in the ID, α+-thalassemia, β+-thalassemia and β0-thalassemia patients it was 0.7, 0.6, 1.4, and 34.8 ng/ml, respectively. Legend: **$p<0.0001$, $p<0.005$.

An additional study was conducted to quantify serum ERFE concentrations in thalassemia patients known to exhibit ineffective erythropoiesis due to mutations in the α- or β-globulin genes, resulting in hemoglobinopathy and severe iron overload. Sera was obtained from patients with α+-thalassemia and both β+-thalassemia and β0-thalassemia and compared to ERFE levels from sera obtained from a group of iron deficient (ID) and control patients. It was discovered that both β+-thalassemia and β0-thalassemia patients had significantly greater ERFE concentrations than patients from the α+-thalassemia, ID and control groups (FIG. 8). Another significant finding was that β0-thalassemia patients had significantly greater serum ERFE concentrations compared to the β+-thalassemia patients. This finding suggests that serum ERFE measurement may help differentiate patients with the more severe β0-thalassemia trait from patients exhibiting either β+- or α+-thalassemia traits (FIG. 8).

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of assessing erythropoiesis in a subject with a disorder associated with erythroferrone (ERFE) or myonectin, comprising subjecting a sample from the subject to an assay comprising:
  contacting the sample with a first antibody to form a first antibody-ERFE complex;
  and then detecting the presence of and/or measuring the amount of a second antibody bound to the first antibody-ERFE complex, wherein the first antibody and the second antibody are not the same and each are independently an ERFE-binding antibody, or an ERFE-binding fragment thereof, the antibodies selected from:
  (a) an antibody comprising a heavy chain variable region (VH) and a light chain variable region (VL), wherein
    (i) the VH comprises the amino acid sequence of SEQ ID NO:18 and the VL comprises the amino acid sequence of SEQ ID NO:23;
    (ii) the VH comprises the amino acid sequence of SEQ ID NO:28 and the VL comprises the amino acid sequence of SEQ ID NO:33;

(iii) the VH comprises the amino acid sequence of SEQ ID NO:38 and the VL comprises the amino acid sequence of SEQ ID NO:43;
(iv) the VH comprises the amino acid sequence of SEQ ID NO:48 and the VL comprises the amino acid sequence of SEQ ID NO:53; or
(v) the VH comprises the amino acid sequence of SEQ ID N0:58 and the VL comprises the amino acid sequence of SEQ ID NO:63,
or
(b) an antibody comprising:
(i) heavy chain complementarity determining regions (CDRs) having the amino acid sequences of SEQ ID NOs:19-21 and light chain CDRs having the amino acid sequences of SEQ ID NOs:24-26;
(ii) heavy chain CDRs having the amino acid sequences of SEQ ID NOs:29-31 and light chain CDRs having the amino acid sequences of SEQ ID NOs:34-36;
(iii) heavy chain CDRs having the amino acid sequences of SEQ ID NOs:39-41 and light chain CDRs having the amino acid sequences of SEQ ID NOs:44-46;
(iv) heavy chain CDRs having the amino acid sequences of SEQ ID NOs:49-51 and light chain CDRs having the amino acid sequences of SEQ ID NOs:54-56; or
(v) heavy chain CDRs having the amino acid sequences of SEQ ID NOs:59-61 and light chain CDRs having the amino acid sequences of SEQ ID NOs:64-66;
thus determining the presence, and or the amount, of an ERFE protein in the sample.

2. The method of claim 1, wherein the antibody comprises:
(i) heavy chain CDRs 1, 2, and 3 having the amino acid sequences of SEQ ID NOs:19-21, respectively, and light chain CDRs 1, 2, and 3 having the amino acid sequences of SEQ ID NOs:24-26, respectively;
(ii) heavy chain CDRs 1, 2, and 3 having the amino acid sequences of SEQ ID NOs:29-31, respectively, and light chain CDRs 1, 2, and 3 having the amino acid sequences of SEQ ID NOs:34-36, respectively;
(iii) heavy chain CDRs 1, 2, and 3 having the amino acid sequences of SEQ ID NOs:39-41, respectively, and light chain CDRs 1, 2, and 3 having the amino acid sequences of SEQ ID NOs:44-46, respectively;
(iv) heavy chain CDRs 1, 2, and 3 having the amino acid sequences of SEQ ID NOs:49-51, respectively, and light chain CDRs 1, 2, and 3 having the amino acid sequences of SEQ ID NOs:54-56, respectively; or
(v) heavy chain CDRs 1, 2, and 3 having the amino acid sequences of SEQ ID NOs:59-61, respectively, and light chain CDRs 1, 2, and 3having the amino acid sequences of SEQ ID NOs:64-66, respectively.

3. The method of claim 1 wherein the detecting step of the assay comprises contacting the first antibody-ERFE polypeptide complex with the second antibody, wherein the second antibody is labeled.

4. The method of claim 3, wherein the label is biotin.

5. The method of claim 3, wherein the label is horseradish peroxidase.

6. The method of claim 1, wherein the first antibody is a capture antibody and the second antibody is a detection antibody.

7. The method of claim 1, wherein the first antibody is coated on a solid support.

8. The method of claim 1, wherein the first antibody is 4C1 and the second antibody is 2D2.

9. The method of claim 1, wherein the disorder is a thalassemia.

10. The method of claim 1, wherein the disorder is a cardiovascular disorder.

11. A method of assessing erythropoiesis in a subject with a disorder associated with ERFE or myonectin, comprising contacting a sample from a subject with at least one ERFE-binding antibody, or ERFE-binding fragment thereof such that ERFE in the sample is detected and the antibody is selected from:
(a) an antibody comprising a heavy chain variable region (VH) and a light chain variable region (VL), wherein
(i) the VH comprises the amino acid sequence of SEQ ID NO:18 and the VL comprises the amino acid sequence of SEQ ID NO:23;
(ii) the VH comprises the amino acid sequence of SEQ ID NO:28 and the VL comprises the amino acid sequence of SEQ ID NO:33;
(iii) the VH comprises the amino acid sequence of SEQ ID NO:38 and the VL comprises the amino acid sequence of SEQ ID NO:43;
(iv) the VH comprises the amino acid sequence of SEQ ID NO:48 and the VL comprises the amino acid sequence of SEQ ID NO:53; or
(v) the VH comprises the amino acid sequence of SEQ ID N0:58 and the VL comprises the amino acid sequence of SEQ ID NO:63,
or
(b) an antibody comprising:
(i) heavy chain complementarity determining regions (CDRs) having the amino acid sequences of SEQ ID NOs:19-21 and light chain CDRs having the amino acid sequences of SEQ ID NOs:24-26;
(ii) heavy chain CDRs having the amino acid sequences of SEQ ID NOs:29-31 and light chain CDRs having the amino acid sequences of SEQ ID NOs:34-36;
(iii) heavy chain CDRs having the amino acid sequences of SEQ ID NOs:39-41 and light chain CDRs having the amino acid sequences of SEQ ID NOs:44-46;
(iv) heavy chain CDRs having the amino acid sequences of SEQ ID NOs:49-51 and light chain CDRs having the amino acid sequences of SEQ ID NOs:54-56; or
(v) heavy chain CDRs having the amino acid sequences of SEQ ID NOs:59-61 and light chain CDRs having the amino acid sequences of SEQ ID NOs:64-66.

12. The method of claim 11, wherein the at least one antibody comprises:
(i) heavy chain CDRs 1, 2, and 3 having the amino acid sequences of SEQ ID NOs:19-21, respectively, and light chain CDRs 1, 2, and 3 having the amino acid sequences of SEQ ID NOs:24-26, respectively;
(ii) heavy chain CDRs 1, 2, and 3 having the amino acid sequences of SEQ ID NOs:29-31, respectively, and light chain CDRs 1, 2, and 3 having the amino acid sequences of SEQ ID NOs:34-36, respectively;
(iii) heavy chain CDRs 1, 2, and 3 having the amino acid sequences of SEQ ID NOs:39-41, respectively, and light chain CDRs 1, 2, and 3 having the amino acid sequences of SEQ ID NOs:44-46, respectively;
(iv) heavy chain CDRs 1, 2, and 3 having the amino acid sequences of SEQ ID NOs:49-51, respectively, and light chain CDRs 1, 2, and 3 having the amino acid sequences of SEQ ID NOs:54-56, respectively; or
(v) heavy chain CDRs 1, 2, and 3 having the amino acid sequences of SEQ ID NOs:59-61, respectively, and light chain CDRs 1, 2, and 3 having the amino acid sequences of SEQ ID NOs:64-66, respectively.

13. The method of claim 11 wherein the detecting step of the assay comprises contacting an antibody-ERFE polypeptide complex with a second ERFE binding antibody, wherein the second antibody is labeled.

14. The method of claim 13, wherein the first antibody is a capture antibody and the second antibody is a detection antibody.

15. The method of claim 14, wherein the first antibody is coated on a solid support.

16. The method of claim 14, wherein the first antibody is 4C1 and the second antibody is 2D2.

17. The method of claim 13, wherein the label is biotin.

18. The method of claim 13, wherein the label is horseradish peroxidase.

19. The method of claim 11, wherein the disorder is a thalassemia.

20. The method of claim 11, wherein the disorder is a cardiovascular disorder.

\* \* \* \* \*

SEQUENCE LISTING

<160> NUMBER OF SEQ ID NOS: 66

<210> SEQ ID NO 1
<211> LENGTH: 354
<212> TYPE: PRT
<213> ORGANISM: Homo sapiens

<400> SEQUENCE: 1

```
Met Ala Pro Ala Arg Arg Pro Ala Gly Ala Arg Leu Leu Leu Val Tyr
1               5                   10                  15

Ala Gly Leu Leu Ala Ala Ala Ala Gly Leu Gly Ser Pro Glu Pro
            20                  25                  30

Gly Ala Pro Ser Arg Ser Arg Ala Arg Arg Glu Pro Pro Gly Asn
                35                  40                  45

Glu Leu Pro Arg Gly Pro Gly Glu Ser Arg Ala Gly Pro Ala Ala Arg
    50                  55                  60

Pro Pro Glu Pro Thr Ala Glu Arg Ala His Ser Val Asp Pro Arg Asp
65                  70                  75                  80

Ala Trp Met Leu Phe Val Arg Gln Ser Asp Lys Gly Val Asn Gly Lys
                85                  90                  95

Lys Arg Ser Arg Gly Lys Ala Lys Lys Leu Lys Phe Gly Leu Pro Gly
                100                 105                 110

Pro Pro Gly Pro Pro Gly Pro Gln Gly Pro Pro Gly Pro Ile Ile Pro
                115                 120                 125

Pro Glu Ala Leu Leu Lys Glu Phe Gln Leu Leu Leu Lys Gly Ala Val
    130                 135                 140

Arg Gln Arg Glu Arg Ala Glu Pro Glu Pro Cys Thr Cys Gly Pro Ala
145                 150                 155                 160

Gly Pro Val Ala Ala Ser Leu Ala Pro Val Ser Ala Thr Ala Gly Glu
                165                 170                 175

Asp Asp Asp Asp Val Val Gly Asp Val Leu Ala Leu Leu Ala Ala Pro
                180                 185                 190

Leu Ala Pro Gly Pro Arg Ala Pro Arg Val Glu Ala Ala Phe Leu Cys
    195                 200                 205

Arg Leu Arg Arg Asp Ala Leu Val Glu Arg Arg Ala Leu His Glu Leu
210                 215                 220

Gly Val Tyr Tyr Leu Pro Asp Ala Glu Gly Ala Phe Arg Arg Gly Pro
225                 230                 235                 240

Gly Leu Asn Leu Thr Ser Gly Gln Tyr Arg Ala Pro Val Ala Gly Phe
                245                 250                 255

Tyr Ala Leu Ala Ala Thr Leu His Val Ala Leu Gly Glu Pro Pro Arg
                260                 265                 270

Arg Gly Pro Pro Arg Pro Arg Asp His Leu Arg Leu Leu Ile Cys Ile
    275                 280                 285

Gln Ser Arg Cys Gln Arg Asn Ala Ser Leu Glu Ala Ile Met Gly Leu
    290                 295                 300

Glu Ser Ser Ser Glu Leu Phe Thr Ile Ser Val Asn Gly Val Leu Tyr
305                 310                 315                 320

Leu Gln Met Gly Gln Trp Thr Ser Val Phe Leu Asp Asn Ala Ser Gly
                325                 330                 335

Cys Ser Leu Thr Val Arg Ser Gly Ser His Phe Ser Ala Val Leu Leu
                340                 345                 350

Gly Val
```

```
<210> SEQ ID NO 2
<211> LENGTH: 340
<212> TYPE: PRT
<213> ORGANISM: Mus musculus

<400> SEQUENCE: 2

Met Ala Ser Thr Arg Arg Pro Val Gly Ala Arg Thr Leu Leu Ala Cys
1               5                   10                  15

Ala Ser Leu Leu Ala Ala Met Gly Leu Gly Val Pro Glu Ser Ala Glu
            20                  25                  30

Pro Val Gly Thr His Ala Arg Pro Gln Pro Gly Ala Glu Leu Pro
        35                  40                  45

Ala Pro Pro Ala Asn Ser Pro Glu Pro Thr Ile Ala His Ala His
    50                  55                  60

Ser Val Asp Pro Arg Asp Ala Trp Met Leu Phe Val Lys Gln Ser Asp
65                  70                  75                  80

Lys Gly Ile Asn Ser Lys Arg Ser Lys Ala Arg Arg Leu Lys Leu
                85                  90                  95

Gly Leu Pro Gly Pro Gly Pro Pro Gly Pro Gln Gly Pro Pro Gly
            100                 105                 110

Pro Phe Ile Pro Ser Glu Val Leu Leu Lys Glu Phe Gln Leu Leu Leu
        115                 120                 125

Lys Gly Ala Val Arg Gln Arg Glu Ser His Leu Glu His Cys Thr Arg
130                 135                 140

Asp Leu Thr Thr Pro Ala Ser Gly Ser Pro Ser Arg Val Pro Ala Ala
145                 150                 155                 160

Gln Glu Leu Asp Ser Gln Asp Pro Gly Ala Leu Leu Ala Leu Ala
            165                 170                 175

Ala Thr Leu Ala Gln Gly Pro Arg Ala Pro Arg Val Glu Ala Ala Phe
        180                 185                 190

His Cys Arg Leu Arg Arg Asp Val Gln Val Asp Arg Arg Ala Leu His
    195                 200                 205

Glu Leu Gly Ile Tyr Tyr Leu Pro Glu Val Glu Gly Ala Phe His Arg
210                 215                 220

Gly Pro Gly Leu Asn Leu Thr Ser Gly Gln Tyr Thr Ala Pro Val Ala
225                 230                 235                 240

Gly Phe Tyr Ala Leu Ala Ala Thr Leu His Val Ala Leu Thr Glu Gln
                245                 250                 255

Pro Arg Lys Gly Pro Thr Arg Pro Arg Asp Arg Leu Arg Leu Leu Ile
            260                 265                 270

Cys Ile Gln Ser Leu Cys Gln His Asn Ala Ser Leu Glu Thr Val Met
        275                 280                 285

Gly Leu Glu Asn Ser Ser Glu Leu Phe Thr Ile Ser Val Asn Gly Val
    290                 295                 300

Leu Tyr Leu Gln Ala Gly His Tyr Thr Ser Val Phe Leu Asp Asn Ala
305                 310                 315                 320

Ser Gly Ser Ser Leu Thr Val Arg Ser Gly Ser His Phe Ser Ala Ile
                325                 330                 335

Leu Leu Gly Leu
            340

<210> SEQ ID NO 3
<211> LENGTH: 17
<212> TYPE: PRT
<213> ORGANISM: Homo sapiens
```

```
<400> SEQUENCE: 3

Gly Leu Pro Gly Pro Pro Gly Pro Pro Gly Pro Gln Gly Pro Pro Gly
1               5                   10                  15

Pro

<210> SEQ ID NO 4
<211> LENGTH: 14
<212> TYPE: PRT
<213> ORGANISM: Homo sapiens

<400> SEQUENCE: 4

Ala His Ser Val Asp Pro Arg Asp Ala Trp Met Leu Phe Val
1               5                   10

<210> SEQ ID NO 5
<211> LENGTH: 22
<212> TYPE: PRT
<213> ORGANISM: Homo sapiens
<220> FEATURE:
<221> NAME/KEY: misc_feature
<223> OTHER INFORMATION: X = any amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 5

Ala His Ser Val Asp Pro Arg Asp Ala Trp Met Leu Phe Val Xaa Gln
1               5                   10                  15

Ser Asp Lys Gly Xaa Asn
            20

<210> SEQ ID NO 6
<211> LENGTH: 17
<212> TYPE: PRT
<213> ORGANISM: Homo sapiens

<400> SEQUENCE: 6

Leu Leu Lys Glu Phe Gln Leu Leu Leu Lys Gly Ala Val Arg Gln Arg
1               5                   10                  15

Glu

<210> SEQ ID NO 7
<211> LENGTH: 11
<212> TYPE: PRT
<213> ORGANISM: Homo sapiens

<400> SEQUENCE: 7

Gly Pro Arg Ala Pro Arg Val Glu Ala Ala Phe
1               5                   10

<210> SEQ ID NO 8
<211> LENGTH: 16
<212> TYPE: PRT
<213> ORGANISM: Homo sapiens
<220> FEATURE:
<221> NAME/KEY: misc_feature
<223> OTHER INFORMATION: X = any amino acid
<220> FEATURE:
<221> NAME/KEY: misc_feature
<222> LOCATION: (2)..(2)
<223> OTHER INFORMATION: Xaa can be any naturally occurring amino acid
```

```
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 8

Val Xaa Arg Arg Ala Leu His Glu Leu Gly Xaa Tyr Tyr Leu Pro Xaa
1               5                   10                  15

<210> SEQ ID NO 9
<211> LENGTH: 9
<212> TYPE: PRT
<213> ORGANISM: Homo sapiens

<400> SEQUENCE: 9

Gly Leu Asn Leu Thr Ser Gly Gln Tyr
1               5

<210> SEQ ID NO 10
<211> LENGTH: 17
<212> TYPE: PRT
<213> ORGANISM: Homo sapiens

<400> SEQUENCE: 10

Ala Pro Val Ala Gly Phe Tyr Ala Leu Ala Ala Thr Leu His Val Ala
1               5                   10                  15

Leu

<210> SEQ ID NO 11
<211> LENGTH: 22
<212> TYPE: PRT
<213> ORGANISM: Homo sapiens
<220> FEATURE:
<221> NAME/KEY: misc_feature
<223> OTHER INFORMATION: X = any amino acid
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 11

Xaa Met Gly Leu Glu Xaa Ser Ser Glu Leu Phe Thr Ile Ser Val Asn
1               5                   10                  15

Gly Val Leu Tyr Leu Gln
            20

<210> SEQ ID NO 12
<211> LENGTH: 16
<212> TYPE: PRT
<213> ORGANISM: Homo sapiens

<400> SEQUENCE: 12

Ser Ser Glu Leu Phe Thr Ile Ser Val Asn Gly Val Leu Tyr Leu Gln
1               5                   10                  15

<210> SEQ ID NO 13
<211> LENGTH: 10
<212> TYPE: PRT
<213> ORGANISM: Homo sapiens
```

<400> SEQUENCE: 13

Thr Ser Val Phe Leu Asp Asn Ala Ser Gly
1               5                   10

<210> SEQ ID NO 14
<211> LENGTH: 12
<212> TYPE: PRT
<213> ORGANISM: Homo sapiens

<400> SEQUENCE: 14

Ser Leu Thr Val Arg Ser Gly Ser His Phe Ser Ala
1               5                   10

<210> SEQ ID NO 15
<211> LENGTH: 17
<212> TYPE: PRT
<213> ORGANISM: Homo sapiens
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 15

Ser Leu Thr Val Arg Ser Gly Ser His Phe Ser Ala Xaa Leu Leu Gly
1               5                   10                  15

Xaa

<210> SEQ ID NO 16
<211> LENGTH: 220
<212> TYPE: PRT
<213> ORGANISM: Homo sapiens

<400> SEQUENCE: 16

Glu Phe Gln Leu Leu Leu Lys Gly Ala Val Arg Gln Arg Glu Arg Ala
1               5                   10                  15

Glu Pro Glu Pro Cys Thr Cys Gly Pro Ala Gly Pro Val Ala Ala Ser
            20                  25                  30

Leu Ala Pro Val Ser Ala Thr Ala Gly Glu Asp Asp Asp Val Val
        35                  40                  45

Gly Asp Val Leu Ala Leu Leu Ala Ala Pro Leu Ala Pro Gly Pro Arg
    50                  55                  60

Ala Pro Arg Val Glu Ala Phe Leu Cys Arg Leu Arg Arg Asp Ala
65                  70                  75                  80

Leu Val Glu Arg Arg Ala Leu His Glu Leu Gly Val Tyr Tyr Leu Pro
                85                  90                  95

Asp Ala Glu Gly Ala Phe Arg Arg Gly Pro Gly Leu Asn Leu Thr Ser
            100                 105                 110

Gly Gln Tyr Arg Ala Pro Val Ala Gly Phe Tyr Ala Leu Ala Ala Thr
        115                 120                 125

Leu His Val Ala Leu Gly Glu Pro Pro Arg Arg Gly Pro Pro Arg Pro
    130                 135                 140

Arg Asp His Leu Arg Leu Leu Ile Cys Ile Gln Ser Arg Cys Gln Arg
145                 150                 155                 160

Asn Ala Ser Leu Glu Ala Ile Met Gly Leu Glu Ser Ser Ser Glu Leu
                165                 170                 175

```
Phe Thr Ile Ser Val Asn Gly Val Leu Tyr Leu Gln Met Gly Gln Trp
                180                 185                 190

Thr Ser Val Phe Leu Asp Asn Ala Ser Gly Cys Ser Leu Thr Val Arg
            195                 200                 205

Ser Gly Ser His Phe Ser Ala Val Leu Leu Gly Val
        210                 215                 220

<210> SEQ ID NO 17
<211> LENGTH: 472
<212> TYPE: PRT
<213> ORGANISM: Mus musculus

<400> SEQUENCE: 17

Met Glu Trp Ser Trp Ile Phe Leu Phe Leu Leu Ser Gly Thr Ala Gly
1               5                   10                  15

Val Leu Ser Glu Val Gln Leu Gln Gln Phe Gly Pro Glu Leu Val Lys
            20                  25                  30

Pro Gly Gly Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Phe Asn Pro Asn Tyr Asp Ser Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Gly Met Ile Leu Tyr Tyr Gly Asn Ser Gly Ser
        115                 120                 125

Met Asp Tyr Trp Gly Gln Gly Thr Ser Val Thr Val Ser Ser Ala Lys
    130                 135                 140

Thr Thr Ala Pro Ser Val Tyr Pro Leu Ala Pro Val Cys Gly Asp Thr
145                 150                 155                 160

Thr Gly Ser Ser Val Thr Leu Gly Cys Leu Val Lys Gly Tyr Phe Pro
                165                 170                 175

Glu Pro Val Thr Leu Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Thr Ser Ser Thr Trp Pro Ser Gln Ser Ile Thr Cys
    210                 215                 220

Asn Val Ala His Pro Ala Ser Ser Thr Lys Val Asp Lys Lys Ile Glu
225                 230                 235                 240

Pro Arg Gly Pro Thr Ile Lys Pro Cys Pro Pro Cys Lys Cys Pro Ala
                245                 250                 255

Pro Asn Leu Leu Gly Gly Pro Ser Val Phe Ile Phe Pro Pro Lys Ile
            260                 265                 270

Lys Asp Val Leu Met Ile Ser Leu Ser Pro Ile Val Thr Cys Val Val
        275                 280                 285

Val Asp Val Ser Glu Asp Asp Pro Asp Val Gln Ile Ser Trp Phe Val
    290                 295                 300

Asn Asn Val Glu Val His Thr Ala Gln Thr Gln Thr His Arg Glu Asp
305                 310                 315                 320

Tyr Asn Ser Thr Leu Arg Val Val Ser Ala Leu Pro Ile Gln His Gln
                325                 330                 335
```

```
Asp Trp Met Ser Gly Lys Glu Phe Lys Cys Lys Val Asn Asn Lys Asp
            340                 345                 350

Leu Pro Ala Pro Ile Glu Arg Thr Ile Ser Lys Pro Lys Gly Ser Val
            355                 360                 365

Arg Ala Pro Gln Val Tyr Val Leu Pro Pro Glu Glu Met Thr
            370                 375                 380

Lys Lys Gln Val Thr Leu Thr Cys Met Val Thr Asp Phe Met Pro Glu
385                 390                 395                 400

Asp Ile Tyr Val Glu Trp Thr Asn Asn Gly Lys Thr Glu Leu Asn Tyr
            405                 410                 415

Lys Asn Thr Glu Pro Val Leu Asp Ser Asp Gly Ser Tyr Phe Met Tyr
            420                 425                 430

Ser Lys Leu Arg Val Glu Lys Lys Asn Trp Val Glu Arg Asn Ser Tyr
            435                 440                 445

Ser Cys Ser Val Val His Glu Gly Leu His Asn His Thr Thr Lys
            450                 455                 460

Ser Phe Ser Arg Thr Pro Gly Lys
465                 470

<210> SEQ ID NO 18
<211> LENGTH: 123
<212> TYPE: PRT
<213> ORGANISM: Mus musculus

<400> SEQUENCE: 18

Glu Val Gln Leu Gln Gln Phe Gly Pro Glu Leu Val Lys Pro Gly Gly
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
            35                  40                  45

Gly Asp Phe Asn Pro Asn Tyr Asp Ser Ser Thr Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Met Ile Leu Tyr Tyr Gly Asn Ser Gly Ser Met Asp Tyr
            100                 105                 110

Trp Gly Gln Gly Thr Ser Val Thr Val Ser Ser
            115                 120

<210> SEQ ID NO 19
<211> LENGTH: 5
<212> TYPE: PRT
<213> ORGANISM: Mus musculus

<400> SEQUENCE: 19

Asp Tyr Asn Met Asp
1               5

<210> SEQ ID NO 20
<211> LENGTH: 17
<212> TYPE: PRT
<213> ORGANISM: Mus musculus

<400> SEQUENCE: 20
```

Asp Phe Asn Pro Asn Tyr Asp Ser Ser Thr Tyr Asn Gln Lys Phe Lys
1               5                   10                  15

Gly

<210> SEQ ID NO 21
<211> LENGTH: 14
<212> TYPE: PRT
<213> ORGANISM: Mus musculus

<400> SEQUENCE: 21

Gly Met Ile Leu Tyr Tyr Gly Asn Ser Gly Ser Met Asp Tyr
1               5                   10

<210> SEQ ID NO 22
<211> LENGTH: 234
<212> TYPE: PRT
<213> ORGANISM: Mus musculus

<400> SEQUENCE: 22

Met Lys Phe Pro Ser Gln Leu Leu Phe Leu Leu Phe Arg Ile Thr
1               5                   10                  15

Gly Ile Met Cys Asp Ile Gln Met Thr Gln Ser Ser Ser Tyr Leu Ser
            20                  25                  30

Val Ser Leu Gly Gly Arg Val Thr Ile Thr Cys Lys Ala Ser Asp His
        35                  40                  45

Ile Asn Asn Trp Leu Ala Trp Tyr Gln Gln Lys Pro Gly Asn Ala Pro
    50                  55                  60

Arg Leu Leu Ile Ser Gly Ala Thr Ser Leu Glu Thr Gly Val Pro Ser
65                  70                  75                  80

Arg Phe Ser Gly Ser Gly Ser Gly Lys Asp Tyr Thr Leu Thr Ile Ile
                85                  90                  95

Ser Leu Gln Thr Glu Asp Val Ala Thr Tyr Tyr Cys Gln Gln Tyr Trp
            100                 105                 110

Asn Thr Pro Arg Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 23
<211> LENGTH: 127
<212> TYPE: PRT
<213> ORGANISM: Mus musculus

<400> SEQUENCE: 23

Met Lys Phe Pro Ser Gln Leu Leu Leu Phe Leu Leu Phe Arg Ile Thr
1               5                   10                  15

-continued

```
Gly Ile Met Cys Asp Ile Gln Met Thr Gln Ser Ser Ser Tyr Leu Ser
            20                  25                  30

Val Ser Leu Gly Gly Arg Val Thr Ile Thr Cys Lys Ala Ser Asp His
        35                  40                  45

Ile Asn Asn Trp Leu Ala Trp Tyr Gln Gln Lys Pro Gly Asn Ala Pro
    50                  55                  60

Arg Leu Leu Ile Ser Gly Ala Thr Ser Leu Glu Thr Gly Val Pro Ser
65                  70                  75                  80

Arg Phe Ser Gly Ser Gly Ser Gly Lys Asp Tyr Thr Leu Thr Ile Ile
                85                  90                  95

Ser Leu Gln Thr Glu Asp Val Ala Thr Tyr Tyr Cys Gln Gln Tyr Trp
            100                 105                 110

Asn Thr Pro Arg Thr Phe Gly Gly Thr Lys Leu Glu Ile Lys
        115                 120                 125

<210> SEQ ID NO 24
<211> LENGTH: 11
<212> TYPE: PRT
<213> ORGANISM: Mus musculus

<400> SEQUENCE: 24

Lys Ala Ser Asp His Ile Asn Asn Trp Leu Ala
1               5                   10

<210> SEQ ID NO 25
<211> LENGTH: 7
<212> TYPE: PRT
<213> ORGANISM: Mus musculus

<400> SEQUENCE: 25

Gly Ala Thr Ser Leu Glu Thr
1               5

<210> SEQ ID NO 26
<211> LENGTH: 9
<212> TYPE: PRT
<213> ORGANISM: Mus musculus

<400> SEQUENCE: 26

Gln Gln Tyr Trp Asn Thr Pro Arg Thr
1               5

<210> SEQ ID NO 27
<211> LENGTH: 466
<212> TYPE: PRT
<213> ORGANISM: Mus musculus

<400> SEQUENCE: 27

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Thr Tyr Ser Ile His Trp Val Arg Gln Ser Pro Gly Lys Gly Leu
    50                  55                  60

Glu Trp Leu Gly Val Ile Trp Ser Gly Gly Ser Ile Asp Tyr Asn Ala
65                  70                  75                  80

Ala Phe Ile Ser Arg Leu Thr Ile Thr Lys Asp Asn Ser Lys Ser Gln
```

```
                    85                  90                  95
Val Phe Phe Lys Met Asn Ser Leu Gln Val Asn Asp Thr Ala Ile Tyr
                100                 105                 110

Tyr Cys Ala Arg Asn Val Leu Thr Tyr Tyr Arg Tyr Asp Val Glu Ala
                115                 120                 125

Met Asp Tyr Trp Gly Gln Gly Thr Ser Val Thr Val Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
                180                 185                 190

His Thr Phe Pro Ala Val Leu Gln Ser Asp Leu Tyr Thr Leu Ser Ser
                195                 200                 205

Ser Val Thr Val Pro Ser Ser Thr Trp Pro Ser Glu Thr Val Thr Cys
                210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
                260                 265                 270

Thr Leu Thr Pro Lys Val Thr Cys Val Val Asp Ile Ser Lys Asp
                275                 280                 285

Asp Pro Glu Val Gln Phe Ser Trp Phe Val Asp Val Glu Val His
290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
                340                 345                 350

Lys Thr Ile Ser Lys Thr Lys Gly Arg Pro Lys Ala Pro Gln Val Tyr
                355                 360                 365

Thr Ile Pro Pro Pro Lys Glu Gln Met Ala Lys Asp Lys Val Ser Leu
                370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Val Tyr Ser Lys Leu Asn Val Gln
                420                 425                 430

Lys Ser Asn Trp Glu Ala Gly Asn Thr Phe Thr Cys Ser Val Leu His
                435                 440                 445

Glu Gly Leu His Asn His His Thr Glu Lys Ser Leu Ser His Ser Pro
                450                 455                 460

Gly Lys
465

<210> SEQ ID NO 28
<211> LENGTH: 123
<212> TYPE: PRT
<213> ORGANISM: Mus musculus
```

<400> SEQUENCE: 28

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Ser Ile His Trp Val Arg Gln Ser Pro Gly Lys Gly Leu Glu Trp Leu
        35                  40                  45

Gly Val Ile Trp Ser Gly Gly Ser Ile Asp Tyr Asn Ala Ala Phe Ile
    50                  55                  60

Ser Arg Leu Thr Ile Thr Lys Asp Asn Ser Lys Ser Gln Val Phe Phe
65                  70                  75                  80

Lys Met Asn Ser Leu Gln Val Asn Asp Thr Ala Ile Tyr Tyr Cys Ala
                85                  90                  95

Arg Asn Val Leu Thr Tyr Tyr Arg Tyr Asp Val Glu Ala Met Asp Tyr
            100                 105                 110

Trp Gly Gln Gly Thr Ser Val Thr Val Ser Ser
        115                 120

<210> SEQ ID NO 29
<211> LENGTH: 5
<212> TYPE: PRT
<213> ORGANISM: Mus musculus

<400> SEQUENCE: 29

Thr Tyr Ser Ile His
1               5

<210> SEQ ID NO 30
<211> LENGTH: 16
<212> TYPE: PRT
<213> ORGANISM: Mus musculus

<400> SEQUENCE: 30

Val Ile Trp Ser Gly Gly Ser Ile Asp Tyr Asn Ala Ala Phe Ile Ser
1               5                   10                  15

<210> SEQ ID NO 31
<211> LENGTH: 15
<212> TYPE: PRT
<213> ORGANISM: Mus musculus

<400> SEQUENCE: 31

Asn Val Leu Thr Tyr Tyr Arg Tyr Asp Val Glu Ala Met Asp Tyr
1               5                   10                  15

<210> SEQ ID NO 32
<211> LENGTH: 234
<212> TYPE: PRT
<213> ORGANISM: Mus musculus

<400> SEQUENCE: 32

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Ser Ala Ser Gln Gly
        35                  40                  45

Ile Ser Asn Phe Leu Asn Trp Tyr Gln Gln Lys Pro Asp Gly Thr Val
    50                  55                  60

Lys Leu Leu Ile Tyr Tyr Thr Ser Asn Leu His Ser Gly Val Pro Ser
65                  70                  75                  80

Arg Phe Ser Gly Ser Gly Ser Gly Thr Asp Tyr Ser Leu Thr Val Ser
                85                  90                  95

Asn Leu Glu Pro Glu Asp Ile Ala Thr Tyr Tyr Cys Gln Gln Tyr Ser
            100                 105                 110

Glu Leu Pro Phe Thr Phe Gly Ser Gly Thr Lys Leu Val Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 33
<211> LENGTH: 114
<212> TYPE: PRT
<213> ORGANISM: Mus musculus

<400> SEQUENCE: 33

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Phe
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Ser Leu Thr Val Ser Asn Leu Glu Pro
65                  70                  75                  80

Glu Asp Ile Ala Thr Tyr Tyr Cys Gln Gln Tyr Ser Glu Leu Pro Phe
                85                  90                  95

Thr Phe Gly Ser Gly Thr Lys Leu Val Ile Lys Arg Ala Asp Ala Ala
            100                 105                 110

Pro Thr

<210> SEQ ID NO 34
<211> LENGTH: 11
<212> TYPE: PRT
<213> ORGANISM: Mus musculus

<400> SEQUENCE: 34

Ser Ala Ser Gln Gly Ile Ser Asn Phe Leu Asn
1               5                   10

<210> SEQ ID NO 35
<211> LENGTH: 7

<212> TYPE: PRT
<213> ORGANISM: Mus musculus

<400> SEQUENCE: 35

Tyr Thr Ser Asn Leu His Ser
1               5

<210> SEQ ID NO 36
<211> LENGTH: 9
<212> TYPE: PRT
<213> ORGANISM: Mus musculus

<400> SEQUENCE: 36

Gln Gln Tyr Ser Glu Leu Pro Phe Thr
1               5

<210> SEQ ID NO 37
<211> LENGTH: 465
<212> TYPE: PRT
<213> ORGANISM: Mus musculus

<400> SEQUENCE: 37

Met Glu Cys Asn Trp Ile Leu Pro Phe Ile Leu Ser Val Thr Ser Gly
1               5                   10                  15

Val Tyr Ser Glu Val Gln Leu Gln Gln Ser Gly Thr Val Val Ala Arg
            20                  25                  30

Pro Gly Ala Ser Val Lys Met Ser Cys Lys Ala Ser Gly Tyr Thr Phe
        35                  40                  45

Thr Thr Tyr Trp Met His Trp Val Lys Gln Trp Pro Gly Gln Gly Leu
    50                  55                  60

Glu Trp Ile Gly Ala Ile Tyr Pro Gly Asn Ser Asp Thr Thr Tyr Asn
65                  70                  75                  80

Gln Lys Phe Lys Gly Lys Ala Lys Leu Thr Ala Val Thr Ser Thr Ser
                85                  90                  95

Thr Ala Tyr Met Glu Leu Ser Ser Leu Thr Asn Glu Asp Ser Ala Val
            100                 105                 110

Tyr Tyr Cys Thr Arg Glu Asp Phe Tyr Asn Gly Tyr Asp Ala Glu Phe
        115                 120                 125

Ala Tyr Trp Gly Gln Gly Thr Leu Val Thr Val Ser Ala Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Glu Thr Val Thr Cys Asn
    210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Asp Ile Ser Lys Asp Asp

```
            275                 280                 285
Pro Glu Val Gln Phe Ser Trp Phe Val Asp Val Glu Val His Thr
290                 295                 300

Ala Gln Thr Gln Pro Arg Glu Glu Gln Phe Asn Ser Thr Phe Arg Ser
305                 310                 315                 320

Val Ser Glu Leu Pro Ile Met His Gln Asp Trp Leu Asn Gly Lys Glu
            325                 330                 335

Phe Lys Cys Arg Val Asn Ser Ala Ala Phe Pro Ala Pro Ile Glu Lys
            340                 345                 350

Thr Ile Ser Lys Thr Lys Gly Arg Pro Lys Ala Pro Gln Val Tyr Thr
            355                 360                 365

Ile Pro Pro Pro Lys Glu Gln Met Ala Lys Asp Lys Val Ser Leu Thr
            370                 375                 380

Cys Met Ile Thr Asp Phe Phe Pro Glu Asp Ile Thr Val Glu Trp Gln
385                 390                 395                 400

Trp Asn Gly Gln Pro Ala Glu Asn Tyr Lys Asn Thr Gln Pro Ile Met
            405                 410                 415

Asp Thr Asp Gly Ser Tyr Phe Val Tyr Ser Lys Leu Asn Val Gln Lys
            420                 425                 430

Ser Asn Trp Glu Ala Gly Asn Thr Phe Thr Cys Ser Val Leu His Glu
            435                 440                 445

Gly Leu His Asn His His Thr Glu Lys Ser Leu Ser His Ser Pro Gly
            450                 455                 460

Lys
465

<210> SEQ ID NO 38
<211> LENGTH: 122
<212> TYPE: PRT
<213> ORGANISM: Mus musculus

<400> SEQUENCE: 38

Glu Val Gln Leu Gln Gln Ser Gly Thr Val Val Ala Arg Pro Gly Ala
1               5                   10                  15

Ser Val Lys Met Ser Cys Lys Ala Ser Gly Tyr Thr Phe Thr Thr Tyr
            20                  25                  30

Trp Met His Trp Val Lys Gln Trp Pro Gly Gln Gly Leu Glu Trp Ile
        35                  40                  45

Gly Ala Ile Tyr Pro Gly Asn Ser Asp Thr Thr Tyr Asn Gln Lys Phe
    50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Glu Asp Phe Tyr Asn Gly Tyr Asp Ala Glu Phe Ala Tyr Trp
            100                 105                 110

Gly Gln Gly Thr Leu Val Thr Val Ser Ala
        115                 120

<210> SEQ ID NO 39
<211> LENGTH: 5
<212> TYPE: PRT
<213> ORGANISM: Mus musculus

<400> SEQUENCE: 39

Thr Tyr Trp Met His
```

<210> SEQ ID NO 40
<211> LENGTH: 19
<212> TYPE: PRT
<213> ORGANISM: Mus musculus

<400> SEQUENCE: 40

Ala Ile Tyr Pro Gly Asn Ser Asp Thr Thr Tyr Asn Gln Lys Phe Lys
1               5                   10                  15

Gly Lys Ala

<210> SEQ ID NO 41
<211> LENGTH: 13
<212> TYPE: PRT
<213> ORGANISM: Mus musculus

<400> SEQUENCE: 41

Glu Asp Phe Tyr Asn Gly Tyr Asp Ala Glu Phe Ala Tyr
1               5                   10

<210> SEQ ID NO 42
<211> LENGTH: 234
<212> TYPE: PRT
<213> ORGANISM: Mus musculus

<400> SEQUENCE: 42

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
            35                  40                  45

Ile Ser Asn Tyr Leu Ser Trp Tyr Gln Gln Lys Pro Asp Gly Thr Val
        50                  55                  60

Lys Leu Leu Ile Tyr Ser Thr Ser Lys Leu His Pro Gly Val Pro Pro
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Ser
            100                 105                 110

Thr Leu Leu Arg Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 43
<211> LENGTH: 114
<212> TYPE: PRT
<213> ORGANISM: Mus musculus

<400> SEQUENCE: 43

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Gln Lys Pro Asp Gly Thr Val Lys Leu Leu Ile
        35                  40                  45

Tyr Ser Thr Ser Lys Leu His Pro Gly Val Pro Pro Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Leu Arg
                85                  90                  95

Thr Phe Gly Gly Gly Thr Lys Leu Glu Ile Lys Arg Ala Asp Ala Ala
            100                 105                 110

Pro Thr

<210> SEQ ID NO 44
<211> LENGTH: 11
<212> TYPE: PRT
<213> ORGANISM: Mus musculus

<400> SEQUENCE: 44

Arg Ala Ser Gln Asp Ile Ser Asn Tyr Leu Ser
1               5                   10

<210> SEQ ID NO 45
<211> LENGTH: 7
<212> TYPE: PRT
<213> ORGANISM: Mus musculus

<400> SEQUENCE: 45

Ser Thr Ser Lys Leu His Pro
1               5

<210> SEQ ID NO 46
<211> LENGTH: 9
<212> TYPE: PRT
<213> ORGANISM: Mus musculus

<400> SEQUENCE: 46

Gln Gln Gly Ser Thr Leu Leu Arg Thr
1               5

<210> SEQ ID NO 47
<211> LENGTH: 462
<212> TYPE: PRT
<213> ORGANISM: Mus musculus

<400> SEQUENCE: 47

Met Gly Trp Ser Arg Ile Phe Leu Phe Leu Leu Ser Ile Ile Ala Gly
1               5                   10                  15

Val His Cys Gln Val Gln Leu Gln Gln Ser Gly Pro Glu Leu Val Lys
            20                  25                  30

Pro Gly Ala Ser Val Arg Ile Ser Cys Lys Ala Ser Gly Tyr Thr Phe

```
              35                  40                  45
Thr Ser Tyr Tyr Ile His Trp Val Lys Gln Arg Pro Gly Gln Gly Leu
 50                  55                  60

Glu Trp Ile Ala Trp Ile Tyr Pro Gly Asn Val Asn Thr Glu Tyr Asn
 65                  70                  75                  80

Glu Lys Phe Lys Gly Lys Ala Thr Leu Thr Ala Asp Glu Ser Ser Ser
                 85                  90                  95

Thr Ala Tyr Met Gln Leu Ser Ser Leu Thr Ser Glu Asp Ser Ala Val
                100                 105                 110

Phe Phe Cys Ala Arg Glu Gly Ile Thr Thr Asn Ala Leu Asp Tyr Trp
                115                 120                 125

Gly Gln Gly Thr Ser Val Thr Val Ser Ser Ala Lys Thr Thr Pro Pro
            130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
                180                 185                 190

Ala Val Leu Gln Ser Asp Leu Tyr Thr Leu Ser Ser Ser Val Thr Val
            195                 200                 205

Pro Ser Ser Thr Trp Pro Ser Glu Thr Val Thr Cys Asn Val Ala His
210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
                260                 265                 270

Lys Val Thr Cys Val Val Val Asp Ile Ser Lys Asp Asp Pro Glu Val
            275                 280                 285

Gln Phe Ser Trp Phe Val Asp Asp Val Glu Val His Thr Ala Gln Thr
290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
                340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
                420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys
450                 455                 460
```

<210> SEQ ID NO 48
<211> LENGTH: 115
<212> TYPE: PRT
<213> ORGANISM: Mus musculus

<400> SEQUENCE: 48

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Ala Trp Ile Tyr Pro Gly Asn Val Asn Thr Glu Tyr Asn Glu Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Thr Ser Glu Asp Ser Ala Val Phe Phe Cys
                85                  90                  95

Ala Arg Glu Gly Ile Thr Thr Asn Ala Leu Asp Tyr Trp Gly Gln Gly
            100                 105                 110

Thr Ser Val
        115

<210> SEQ ID NO 49
<211> LENGTH: 5
<212> TYPE: PRT
<213> ORGANISM: Mus musculus

<400> SEQUENCE: 49

Ser Tyr Tyr Ile His
1               5

<210> SEQ ID NO 50
<211> LENGTH: 17
<212> TYPE: PRT
<213> ORGANISM: Mus musculus

<400> SEQUENCE: 50

Trp Ile Tyr Pro Gly Asn Val Asn Thr Glu Tyr Asn Glu Lys Phe Lys
1               5                   10                  15

Gly

<210> SEQ ID NO 51
<211> LENGTH: 10
<212> TYPE: PRT
<213> ORGANISM: Mus musculus

<400> SEQUENCE: 51

Glu Gly Ile Thr Thr Asn Ala Leu Asp Tyr
1               5                   10

<210> SEQ ID NO 52
<211> LENGTH: 233
<212> TYPE: PRT
<213> ORGANISM: Mus musculus

<400> SEQUENCE: 52

Met Met Ser Ser Ala Gln Phe Leu Gly Leu Leu Leu Phe Cys Phe Gln
1               5                   10                  15

Gly Thr Arg Cys Asp Ile Gln Met Thr Gln Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu Tyr Ser Gly Val Pro Ser
65                  70                  75                  80

Arg Phe Ser Gly Asn Gly Ser Gly Ser Asp Tyr Ser Leu Thr Ile Ser
                85                  90                  95

Asn Leu Glu Gln Glu Asp Ile Ala Thr Tyr Phe Cys Gln Gln Gly His
            100                 105                 110

Thr Leu Trp Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
210                 215                 220

Val Lys Ser Phe Asn Arg Asn Glu Cys
225                 230

<210> SEQ ID NO 53
<211> LENGTH: 106
<212> TYPE: PRT
<213> ORGANISM: Mus musculus

<400> SEQUENCE: 53

Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Tyr Ser Gly Val Pro Ser Arg Phe Ser Gly
    50                  55                  60

Asn Gly Ser Gly Ser Asp Tyr Ser Leu Thr Ile Ser Asn Leu Glu Gln
65                  70                  75                  80

Glu Asp Ile Ala Thr Tyr Phe Cys Gln Gln Gly His Thr Leu Trp Thr
                85                  90                  95

Phe Gly Gly Gly Thr Lys Leu Glu Ile Lys
            100                 105

<210> SEQ ID NO 54
<211> LENGTH: 11
<212> TYPE: PRT
<213> ORGANISM: Mus musculus

<400> SEQUENCE: 54

Arg Ala Ser Gln Asp Ile Ser Asn Tyr Leu Asn
1               5                   10

<210> SEQ ID NO 55
<211> LENGTH: 7
<212> TYPE: PRT
<213> ORGANISM: Mus musculus

<400> SEQUENCE: 55

Tyr Thr Ser Arg Leu Tyr Ser
1               5

<210> SEQ ID NO 56
<211> LENGTH: 8
<212> TYPE: PRT
<213> ORGANISM: Mus musculus

<400> SEQUENCE: 56

Gln Gln Gly His Thr Leu Trp Thr
1               5

<210> SEQ ID NO 57
<211> LENGTH: 462
<212> TYPE: PRT
<213> ORGANISM: Mus musculus

<400> SEQUENCE: 57

Met Gly Trp Ser Ser Ile Ile Leu Phe Leu Val Ala Thr Ala Thr Gly
1               5                   10                  15

Val His Ser Gln Val Gln Leu Gln Gln Pro Gly Ser Val Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Met His Trp Ala Lys Gln Arg Pro Gly Gln Gly Leu
    50                  55                  60

Glu Trp Ile Gly Glu Ile His Pro Lys Ser Gly Asp Thr Asn His Asn
65                  70                  75                  80

Glu Lys Phe Lys Gly Lys Ala Thr Leu Thr Val Asp Thr Ser Ser Asn
                85                  90                  95

Thr Ala Tyr Val Asp Leu Ser Ser Leu Thr Ser Glu Asp Ser Ala Val
            100                 105                 110

Tyr Tyr Cys Ala Arg Glu Gly Ile Thr Thr Val Gly Phe Asp Leu Trp
        115                 120                 125

Gly Ala Gly Thr Thr Val Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe

```
            245                 250                 255
Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
            275                 280                 285

Gln Phe Ser Trp Phe Val Asp Asp Val Glu Val His Thr Ala Gln Thr
            290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
            325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
            370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                    405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys
            450                 455                 460

<210> SEQ ID NO 58
<211> LENGTH: 119
<212> TYPE: PRT
<213> ORGANISM: Mus musculus

<400> SEQUENCE: 58

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Ala Lys Gln Arg Pro Gly Gln Gly Leu Glu Trp Ile
        35                  40                  45

Gly Glu Ile His Pro Lys Ser Gly Asp Thr Asn His Asn Glu Lys Phe
    50                  55                  60

Lys Gly Lys Ala Thr Leu Thr Val Asp Thr Ser Ser Asn Thr Ala Tyr
65                  70                  75                  80

Val Asp Leu Ser Ser Leu Thr Ser Glu Asp Ser Ala Val Tyr Tyr Cys
                85                  90                  95

Ala Arg Glu Gly Ile Thr Thr Val Gly Phe Asp Leu Trp Gly Ala Gly
            100                 105                 110

Thr Thr Val Thr Val Ser Ser
        115

<210> SEQ ID NO 59
<211> LENGTH: 5
<212> TYPE: PRT
<213> ORGANISM: Mus musculus
```

```
<400> SEQUENCE: 59

Ser Tyr Trp Met His
1               5

<210> SEQ ID NO 60
<211> LENGTH: 17
<212> TYPE: PRT
<213> ORGANISM: Mus musculus

<400> SEQUENCE: 60

Glu Ile His Pro Lys Ser Gly Asp Thr Asn His Asn Glu Lys Phe Lys
1               5                   10                  15

Gly

<210> SEQ ID NO 61
<211> LENGTH: 10
<212> TYPE: PRT
<213> ORGANISM: Mus musculus

<400> SEQUENCE: 61

Glu Gly Ile Thr Thr Val Gly Phe Asp Leu
1               5                   10

<210> SEQ ID NO 62
<211> LENGTH: 235
<212> TYPE: PRT
<213> ORGANISM: Mus musculus

<400> SEQUENCE: 62

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
                20                  25                  30

Met Ser Ala Ser Pro Gly Gln Lys Val Thr Leu Thr Cys Ser Ala Ser
            35                  40                  45

Ser Ser Val Ser Tyr Met Asn Trp Val Gln Gln Lys Ser Gly Thr Ser
        50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Val Glu Ala Glu Asp Ala Ala Thr Tyr Tyr Cys Gln Gln Trp
                100                 105                 110

Ser Ser His Pro Tyr Thr Phe Gly Gly Gly Thr Lys Leu Glu Ile Lys
            115                 120                 125

Arg Ala Asp Ala Ala Pro Thr Val Ser Ile Phe Pro Pro Ser Ser Glu
        130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220
```

```
Pro Ile Val Lys Ser Phe Asn Arg Asn Glu Cys
225                 230                 235

<210> SEQ ID NO 63
<211> LENGTH: 106
<212> TYPE: PRT
<213> ORGANISM: Mus musculus

<400> SEQUENCE: 63

Gln Ile Val Leu Thr Gln Ser Pro Ala Ile Met Ser Ala Ser Pro Gly
1               5                   10                  15

Gln Lys Val Thr Leu Thr Cys Ser Ala Ser Ser Val Ser Tyr Met
                20                  25                  30

Asn Trp Val Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Trp Ser Ser His Pro Tyr Thr
                85                  90                  95

Phe Gly Gly Gly Thr Lys Leu Glu Ile Lys
            100                 105

<210> SEQ ID NO 64
<211> LENGTH: 10
<212> TYPE: PRT
<213> ORGANISM: Mus musculus

<400> SEQUENCE: 64

Ser Ala Ser Ser Ser Val Ser Tyr Met Asn
1               5                   10

<210> SEQ ID NO 65
<211> LENGTH: 7
<212> TYPE: PRT
<213> ORGANISM: Mus musculus

<400> SEQUENCE: 65

Asp Thr Ser Lys Leu Ala Ser
1               5

<210> SEQ ID NO 66
<211> LENGTH: 9
<212> TYPE: PRT
<213> ORGANISM: Mus musculus

<400> SEQUENCE: 66

Gln Gln Trp Ser Ser His Pro Tyr Thr
1               5
```